(12) United States Patent
Hayama et al.

(10) Patent No.: US 10,217,954 B2
(45) Date of Patent: Feb. 26, 2019

(54) COMPOUND, MATERIAL FOR ORGANIC ELECTROLUMINESCENT ELEMENT, ORGANIC ELECTROLUMINESCENT ELEMENT, AND ELECTRONIC DEVICE

(71) Applicant: Idemitsu Kosan Co., Ltd., Tokyo (JP)

(72) Inventors: Tomoharu Hayama, Sodegaura (JP); Masahiro Kawamura, Sodegaura (JP); Yumiko Mizuki, Sodegaura (JP); Hirokatsu Ito, Sodegaura (JP); Tasuku Haketa, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 163 days.

(21) Appl. No.: 14/909,538

(22) PCT Filed: Nov. 13, 2014

(86) PCT No.: PCT/JP2014/080086
§ 371 (c)(1),
(2) Date: Feb. 2, 2016

(87) PCT Pub. No.: WO2015/072520
PCT Pub. Date: May 21, 2015

(65) Prior Publication Data
US 2016/0181564 A1   Jun. 23, 2016

(30) Foreign Application Priority Data

Nov. 13, 2013   (JP) .................................. 2013-235300

(51) Int. Cl.
*H01L 51/50* (2006.01)
*C07D 401/14* (2006.01)
(Continued)

(52) U.S. Cl.
CPC ........ *H01L 51/5092* (2013.01); *C07D 401/14* (2013.01); *C07D 403/14* (2013.01);
(Continued)

(58) Field of Classification Search
CPC ............. H01L 51/5092; H01L 51/5072; H01L 51/0067; H01L 51/0071–51/0073;
(Continued)

(56) References Cited

U.S. PATENT DOCUMENTS

| | | | |
|---|---|---|---|
| 2004/0086745 A1 | 5/2004 | Iwakuma et al. | |
| 2005/0158578 A1 | 7/2005 | Iwakuma et al. | |

(Continued)

FOREIGN PATENT DOCUMENTS

| | | | |
|---|---|---|---|
| CN | 102471679 A | 5/2012 | |
| CN | 102503938 A | 6/2012 | |

(Continued)

OTHER PUBLICATIONS

English translation of International Preliminary Report on Patentability issued in corresponding application No. PCT/JP2014/080086 dated May 17, 2016.
(Continued)

*Primary Examiner* — Ruiyun Zhang
(74) *Attorney, Agent, or Firm* — Foley & Lardner LLP

(57) ABSTRACT

A compound of the invention is represented by a formula (1) below. In the formula (1), Cz is represented by a formula (1a) below and Az is represented by a formula (11) below.

(Continued)

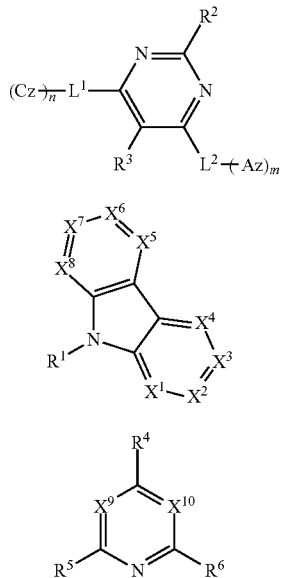

51 Claims, 1 Drawing Sheet

(51) Int. Cl.
  *H01L 51/00* (2006.01)
  *C07D 403/14* (2006.01)
  *C07D 405/14* (2006.01)
  *C07D 409/14* (2006.01)
  *C07D 471/04* (2006.01)
  *C07D 471/14* (2006.01)
  *C07D 471/16* (2006.01)
  *C07D 487/14* (2006.01)
  *C07D 491/048* (2006.01)
  *C07D 495/04* (2006.01)

(52) U.S. Cl.
  CPC ......... *C07D 405/14* (2013.01); *C07D 409/14* (2013.01); *C07D 471/04* (2013.01); *C07D 471/14* (2013.01); *C07D 471/16* (2013.01); *C07D 487/14* (2013.01); *C07D 491/048* (2013.01); *C07D 495/04* (2013.01); *H01L 51/0052* (2013.01); *H01L 51/0054* (2013.01); *H01L 51/0067* (2013.01); *H01L 51/0071* (2013.01); *H01L 51/0072* (2013.01); *H01L 51/0073* (2013.01); *H01L 51/0074* (2013.01); *H01L 51/5012* (2013.01); *H01L 51/5076* (2013.01); *H01L 51/006* (2013.01); *H01L 51/0051* (2013.01); *H01L 51/0058* (2013.01); *H01L 51/0059* (2013.01); *H01L 51/0061* (2013.01); *H01L 51/5072* (2013.01); *H01L 51/5088* (2013.01)

(58) Field of Classification Search
  CPC .. C07D 401/14; C07D 403/14; C07D 405/14; C07D 409/14; C07D 471/04; C07D 471/14; C07D 487/14
  USPC ...... 428/690, 917; 257/40, E51.035, E51.05; 546/100, 18, 79, 81
  See application file for complete search history.

(56) References Cited

U.S. PATENT DOCUMENTS

| | | |
|---|---|---|
| 2006/0041126 A1 | 2/2006 | Schafer et al. |
| 2006/0141284 A1 | 6/2006 | Tomita et al. |
| 2006/0180806 A1 | 8/2006 | Arakane et al. |
| 2007/0051944 A1 | 3/2007 | Vestweber et al. |
| 2007/0069638 A1 | 3/2007 | Matsuura et al. |
| 2007/0159083 A1 | 7/2007 | Matsuura et al. |
| 2007/0190355 A1 | 8/2007 | Ikeda et al. |
| 2007/0224448 A1 | 9/2007 | Ikeda et al. |
| 2008/0145699 A1 | 6/2008 | Yabe et al. |
| 2009/0236973 A1 | 9/2009 | Yabe et al. |
| 2009/0243473 A1 | 10/2009 | Iwakuma et al. |
| 2010/0039026 A1 | 2/2010 | Yang et al. |
| 2010/0327738 A1 | 12/2010 | Toba et al. |
| 2011/0156014 A1 | 6/2011 | Kim et al. |
| 2011/0248257 A1 | 10/2011 | Kim et al. |
| 2011/0291081 A1 | 12/2011 | Inoue et al. |
| 2012/0104941 A1 | 5/2012 | Jung et al. |
| 2012/0119197 A1 | 5/2012 | Nishimura et al. |
| 2012/0126221 A1 | 5/2012 | Kitamura et al. |
| 2012/0126690 A1 | 5/2012 | Ise et al. |
| 2012/0126691 A1 | 5/2012 | Ise et al. |
| 2012/0126692 A1 | 5/2012 | Ise et al. |
| 2012/0138915 A1* | 6/2012 | Nishimura ............. C09K 11/06 257/40 |
| 2012/0211735 A1 | 8/2012 | Imada et al. |
| 2012/0238105 A1 | 9/2012 | Anémian et al. |
| 2012/0273771 A1 | 11/2012 | Jung et al. |
| 2013/0099214 A1 | 4/2013 | Kim et al. |
| 2013/0200357 A1 | 8/2013 | Ludemann et al. |
| 2013/0200360 A1 | 8/2013 | Oikawa |
| 2013/0207540 A1 | 8/2013 | Itai et al. |
| 2013/0256646 A1 | 10/2013 | Fennimore et al. |
| 2013/0306962 A1 | 11/2013 | Yamamoto et al. |
| 2014/0001456 A1 | 1/2014 | Mizutani et al. |
| 2014/0159023 A1 | 6/2014 | Matsumoto et al. |
| 2014/0272398 A1 | 9/2014 | Hakii et al. |
| 2014/0299865 A1 | 10/2014 | Nishimura et al. |
| 2014/0312338 A1 | 10/2014 | Mizutani et al. |
| 2014/0367656 A1 | 12/2014 | Kim et al. |

FOREIGN PATENT DOCUMENTS

| | | |
|---|---|---|
| CN | 104871332 A | 8/2015 |
| JP | 2003-045662 A | 2/2003 |
| JP | 2005-213188 A | 8/2005 |
| JP | 3695714 B2 | 9/2005 |
| JP | 2005-276801 A | 10/2005 |
| JP | 2008-205488 A | 9/2008 |
| JP | 2008-252094 A | 10/2008 |
| JP | 2009-114370 A | 5/2009 |
| JP | 2009-126793 A | 6/2009 |
| JP | 2010-114180 A | 5/2010 |
| JP | 2010-141353 A | 6/2010 |
| JP | 2010-185047 A | 8/2010 |
| JP | 4741028 B1 | 8/2011 |
| JP | 2012-501319 A | 1/2012 |
| JP | 2012-028634 A | 2/2012 |
| JP | 2012-097006 A | 5/2012 |
| JP | 2012-142613 A | 7/2012 |
| JP | 2014-017389 A | 1/2014 |
| JP | 2014-044972 A | 3/2014 |
| JP | 2004-171808 A | 6/2014 |
| JP | 2014-123687 A | 7/2014 |
| KR | 10-2009-008737 A | 1/2009 |
| KR | 10-20110005666 A | 1/2011 |
| KR | 10-20120057611 A | 6/2012 |
| KR | 10-2012-0072787 A | 7/2012 |
| KR | 10-2014-094408 A | 7/2014 |
| KR | 10-2014-0125061 A | 10/2014 |
| KR | 10-2014-0129435 A | 11/2014 |
| KR | 10-2015-0002072 A | 1/2015 |
| KR | 10-2015-0004099 A | 1/2015 |
| TW | 201412730 A | 4/2013 |
| WO | WO-2005/076669 A1 | 8/2005 |

(56) References Cited

FOREIGN PATENT DOCUMENTS

| WO | WO-2006/013739 A1 | 2/2006 |
| WO | WO-2009/069442 A1 | 6/2009 |
| WO | WO-2010/024572 A2 | 3/2010 |
| WO | WO-2010/134350 A1 | 11/2010 |
| WO | WO-2010/134352 A1 | 11/2010 |
| WO | WO-2011/005060 A2 | 1/2011 |
| WO | WO-2011/108707 A1 | 9/2011 |
| WO | WO-2011/132683 A1 | 10/2011 |
| WO | WO-2013/077362 A1 | 5/2013 |
| WO | WO-2013/100538 A1 | 7/2013 |
| WO | WO-2013/100540 A1 | 7/2013 |
| WO | WO-2013/175746 A1 | 11/2013 |
| WO | WO-2013/175747 A1 | 11/2013 |
| WO | WO-2014/097711 A1 | 6/2014 |
| WO | WO-2014/122933 A1 | 8/2014 |
| WO | WO-2014/123369 A1 | 8/2014 |
| WO | WO-2014/166584 A1 | 10/2014 |
| WO | WO-2014/166585 A1 | 10/2014 |
| WO | WO-2014/166586 A1 | 10/2014 |
| WO | WO-2014/208775 A1 | 12/2014 |
| WO | WO-2014/208829 A1 | 12/2014 |
| WO | WO-2015/000548 A1 | 1/2015 |
| WO | WO-2015/008940 A1 | 1/2015 |
| WO | WO-2015/020217 A1 | 2/2015 |
| WO | WO-2015/033894 A1 | 3/2015 |
| WO | WO-2015/036080 A1 | 3/2015 |

OTHER PUBLICATIONS

International Search Report issued in corresponding application No. PCT/JP2014/080086 dated Jan. 27, 2015 with English translation.
Chinese Office Action dated Feb. 27, 2018 in corresponding application No. 2014800443741.
Korean Office Action dated Jan. 16, 2018 in corresponding application No. 2016-7003153.

* cited by examiner

COMPOUND, MATERIAL FOR ORGANIC ELECTROLUMINESCENT ELEMENT, ORGANIC ELECTROLUMINESCENT ELEMENT, AND ELECTRONIC DEVICE

TECHNICAL FIELD

The present invention relates to a compound, a material for an organic electroluminescence device, an organic electroluminescence device, and an electronic device.

BACKGROUND ART

An organic electroluminescence device (hereinafter, occasionally abbreviated as organic EL device) using an organic substance is highly expected to be used as an inexpensive solid-emitting full-color display device having a large area and has been variously developed. A typical organic EL device includes an emitting layer and a pair of opposing electrodes between which the emitting layer is interposed. When an electric field is applied on both electrodes, electrons are injected from the cathode while holes are injected from the anode. Further, the electrons are recombined with the holes in the emitting layer to generate an excited state. When the excited state is returned to a ground state, energy is emitted as light.

A typical organic EL device exhibits a higher drive voltage and lower luminescence intensity and lower luminous efficiency than those of an inorganic light-emitting diode. Although the organic EL device has been gradually improved in recent years, further lower voltage and higher luminous efficiency have been demanded.

For instance, Patent Literature 1 discloses an organic EL device using a compound having a pyrimidine ring as an electron transporting material. Patent Literature 2 discloses that a compound having a pyridine ring and a pyrimidine or triazine ring as the electron transporting material or a host material for an emitting layer. Patent Literature 3 discloses a phosphorescent organic EL device using a compound having a plurality of pyridine rings as the electron transporting material. Patent Literature 4 discloses an organic EL device using a compound having a biscarbazole skeleton and a nitrogen-containing heterocyclic ring (e.g., a pyridine ring) as the host material for the emitting layer. In Patent Literatures 1 to 4, lower voltage and higher luminous efficiency of the organic EL device have been attempted by using the compound having the nitrogen-containing heterocyclic ring in the emitting layer or an electron transporting layer.

CITATION LIST

Patent Literature(s)

Patent Literature 1: International Publication No. WO2010/024572
Patent Literature 2: International Publication No. WO2011/005060
Patent Literature 3: JP-A-2009-126793
Patent Literature 4: International Publication No. WO2011/132683

SUMMARY OF THE INVENTION

Problems to be Solved by the Invention

However, further improvement in performance of the organic EL device has been demanded for application of the organic EL device to an illumination unit, a display unit and the like.

An object of the invention is to provide a compound capable of improving performance of an organic electroluminescence device, an organic-electroluminescence-device material containing the compound, an organic electroluminescence device containing the compound, and an electronic device including the organic electroluminescence device.

Means for Solving the Problems

According to an aspect of the invention, a compound is represented by a formula (1) below.

[Formula 1]

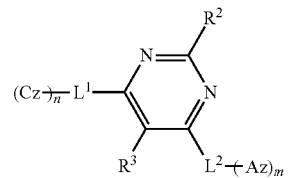

In the formula (1), $R^3$ each independently represents a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, a substituted or unsubstituted arylthio group having 6 to 30 ring carbon atoms, a substituted or unsubstituted aromatic hydrocarbon group having 6 to 30 ring carbon atoms, or a substituted or unsubstituted heterocyclic group having 5 to 30 ring atoms.

$R^2$ is a substituted or unsubstituted aromatic hydrocarbon group having 6 to 30 ring carbon atoms.

When $R^2$ has a substituent, the substituent is a halogen atom, a hydroxyl group, a cyano group, a nitro group, a carboxy group, a substituted or unsubstituted alkyl group having 2 to 30 carbon atoms, a substituted or unsubstituted alkenyl group having 2 to 30 carbon atoms, a substituted or unsubstituted alkynyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted oxygen-containing heterocyclic group having 5 to 30 ring carbon atoms, a substituted or unsubstituted sulfur-containing heterocyclic group having 5 to 30 ring carbon atoms, or a substituted or unsubstituted aromatic hydrocarbon group having 6 to 30 ring carbon atoms.

When the aryloxy group and the arylthio group respectively have substituents, adjacent ones of the substituents are bonded to form a ring or are not bonded.

$L^1$ is a single bond or a linking group and the linking group in $L^1$ is an alkenylene group, an alkynylene group, a substituted or unsubstituted aromatic hydrocarbon group having 6 to 30 ring carbon atoms, a substituted or unsubstituted heterocyclic group having 5 to 30 ring atoms, a multiple linking group provided by bonding two to four groups selected from the above aromatic hydrocarbon group, a multiple linking group provided by bonding two to four groups selected from the above heterocyclic group, or a multiple linking group provided by bonding two to four groups selected from the above aromatic hydrocarbon group and the above heterocyclic group.

The above aromatic hydrocarbon group and the heterocyclic group forming the multiple linking group are mutually the same or different and adjacent ones thereof are bonded to further form a ring or are not bonded.

$L^2$ is a linking group and the linking group represents the same as the linking group in $L^1$.

n and m are each independently an integer of 1 to 5.

When n is an integer of 2 to 5, a plurality of Cz are mutually the same or different.

When m is an integer of 2 to 5, a plurality of Az are mutually the same or different.

Cz is represented by a formula (1a) below.

Az is represented by a formula (11) below.

[Formula 2]

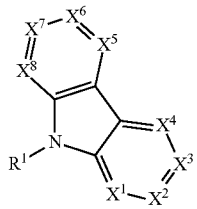

(1a)

In the formula (1a), $X^1$ to $X^8$ are each independently CR or a nitrogen atom.

R and $R^1$ each independently represent a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, a substituted or unsubstituted arylthio group having 6 to 30 ring carbon atoms, a substituted or unsubstituted aromatic hydrocarbon group having 6 to 30 ring carbon atoms, or a substituted or unsubstituted heterocyclic group having 5 to 30 ring atoms.

Adjacent ones of R are mutually bonded to form a ring or are not bonded.

When a plurality of R are present, the plurality of R are the same or different.

However, one of R and $R^1$ is a single bond to be bonded to $L^1$ in the formula (1).

Moreover, $R^1$ and adjacent R are mutually bonded to form a ring or are not bonded.

[formula 3]

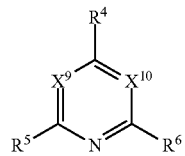

(11)

In the formula (11), $X^9$ is $CR^9$ or a nitrogen atom. $X^{10}$ is $CR^{10}$ or a nitrogen atom.

$R^4$ to $R^6$, $R^9$ and $R^{10}$ each independently represent a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms.

Adjacent groups of $R^4$ to $R^6$, $R^9$ and $R^{10}$ are mutually bonded to further form a ring, or are not bonded.

However, one of $R^4$ to $R^6$, $R^9$ and $R^{10}$ is a single bond to be bonded to $L^2$.

According to the above aspect of the invention, a compound capable of improving performance of an organic electroluminescence device, an organic-electroluminescence-device material containing the compound, an organic electroluminescence device containing the compound, and an electronic device including the organic electroluminescence device can be provided.

DESCRIPTION OF EMBODIMENT(S)

Compound

Figure 1:
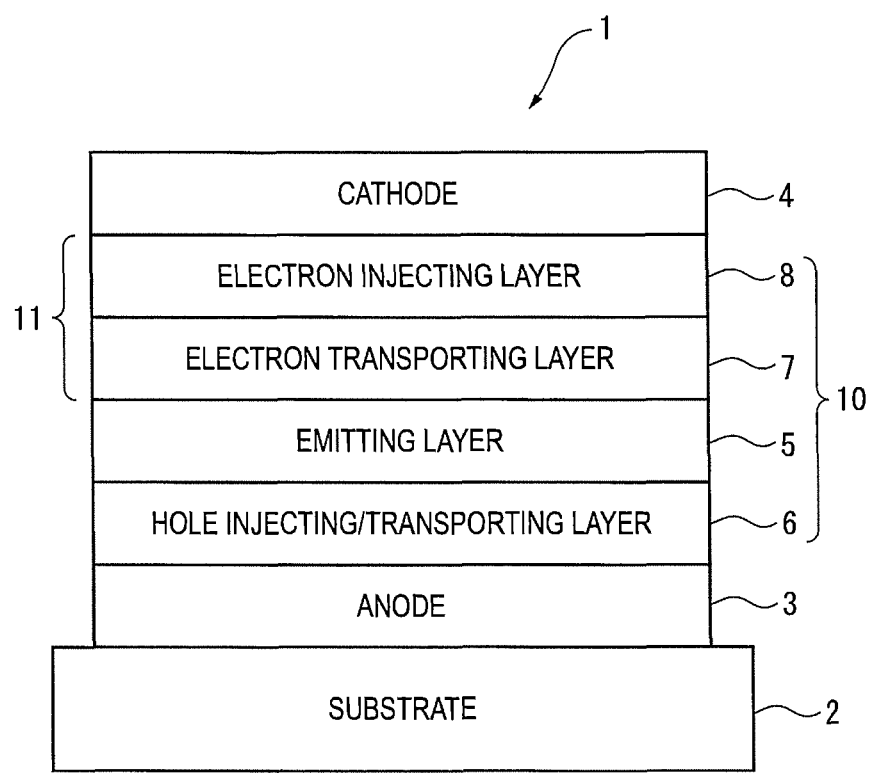
FIG. 1 schematically shows an exemplary arrangement of an organic EL device according to an exemplary embodiment of the invention.

According to an exemplary embodiment of the invention, a compound is represented by a formula (1) below.

[Formula 4]

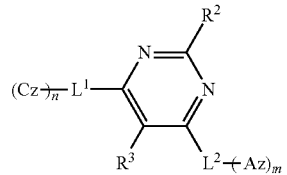

(1)

In the formula (1), $R^3$ each independently represents a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, a substituted or unsubstituted arylthio group having 6 to 30 ring carbon atoms, a substituted or unsubstituted aromatic hydrocarbon group having 6 to 30 ring carbon atoms, or a substituted or unsubstituted heterocyclic group having 5 to 30 ring atoms.

$R^2$ is a substituted or unsubstituted aromatic hydrocarbon group having 6 to 30 ring carbon atoms.

When $R^2$ has a substituent, the substituent is a halogen atom, a hydroxyl group, a cyano group, a nitro group, a carboxy group, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted oxygen-containing heterocyclic group having 5 to 30 ring carbon atoms, a substituted or unsubstituted sulfur-containing heterocyclic group having 5 to 30 ring carbon atoms, or a substituted or unsubstituted aromatic hydrocarbon group having 6 to 30 ring carbon atoms.

When the aryloxy group and the arylthio group respectively have substituents, adjacent ones of the substituents are bonded to form a ring or are not bonded.

$L^1$ is a single bond or a linking group. The linking group in $L^1$ is an alkenylene group, an alkynylene group, a substituted or unsubstituted aromatic hydrocarbon group having 6 to 30 ring carbon atoms, a substituted or unsubstituted heterocyclic group having 5 to 30 ring atoms, a multiple linking group provided by bonding two to four groups selected from the above aromatic hydrocarbon group, a multiple linking group provided by bonding two to four groups selected from the above heterocyclic group, or a multiple linking group provided by bonding two to four groups selected from the above aromatic hydrocarbon group and the above heterocyclic group.

It should be noted that the above aromatic hydrocarbon group and the heterocyclic group forming the multiple linking group are mutually the same or different and adjacent ones thereof are bonded to further form a ring or are not bonded.

$L^2$ is a linking group and the linking group represents the same as the linking group in $L^1$.

n and m are each independently an integer of 1 to 5.

When n is an integer of 2 to 5, a plurality of Cz are mutually the same or different.

When m is an integer of 2 to 5, a plurality of Az are mutually the same or different.

Cz is represented by a formula (1a) below.

Az is represented by a formula (11) below.

[Formula 5]

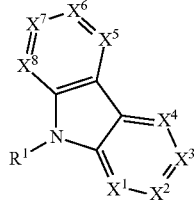

(1a)

In the formula (1a), $X^1$ to $X^8$ are each independently CR or a nitrogen atom.

R and $R^1$ are each independently a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, a substituted or unsubstituted arylthio group having 6 to 30 ring carbon atoms, a substituted or unsubstituted aromatic hydrocarbon group having 6 to 30 ring carbon atoms, or a substituted or unsubstituted heterocyclic group having 5 to 30 ring atoms.

Adjacent ones of R are mutually bonded to form a ring or are not bonded.

When a plurality of R are present, the plurality of R are the same or different.

However, one of R and $R^1$ is a single bond to be bonded to $L^1$ in the formula (1).

Moreover, $R^1$ and adjacent R are mutually bonded to form a ring or are not bonded.

[Formula 6]

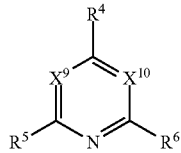

(11)

In the formula (11), $X^9$ is $CR^9$ or a nitrogen atom. $X^{10}$ is $CR^{10}$ or a nitrogen atom.

$R^4$ to $R^6$, $R^9$ and $R^{10}$ each independently represent a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms.

Adjacent groups of $R^4$ to $R^6$, $R^9$ and $R^{10}$ are mutually bonded to further form a ring, or are not bonded.

However, one of $R^4$ to $R^6$, $R^9$ and $R^{10}$ is a single bond to be bonded to $L^2$.

Preferably, the formula (1) is represented by a formula (1A) or (1B).

[Formula 7]

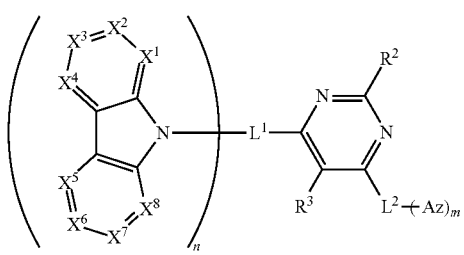

(1A)

In the formula (1A), $L^1$, $L^2$, $R^2$, $R^3$, Az, n and m respectively represent the same as $L^1$, $L^2$, $R^2$, $R^3$, Az, n and m in the formula (1). $X^1$ to $X^8$ respectively represent the same as $X^1$ to $X^8$ in the formula (1a).

[Formula 8]

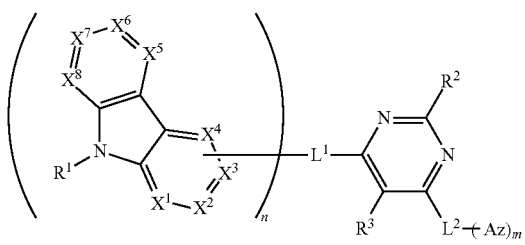

(1B)

In the formula (1B), $L^1$, $L^2$, $R^2$, $R^3$, Az, n and m respectively represent the same as $L^1$, $L^2$, $R^2$, $R^3$, Az, n and m in the formula (1). $R^1$ and $X^1$ to $X^8$ respectively represent the same as $R^1$ and $X^1$ to $X^8$ in the formula (1a).

However, one of $X^1$ to $X^8$ of the formula (1B) is a carbon atom to be bonded to $L^1$.

In the formulae (1), (1A) and (1B), when adjacent groups of $R^4$ to $R^6$, $R^9$ and $R^{10}$ of the formula (11) are mutually bonded to further form a ring, one of $R^4$ to $R^6$, $R^9$ and $R^{10}$ being not bonded is a single bond to be bonded to $L^2$. Moreover, one of $R^4$ to $R^6$, $R^9$ and $R^{10}$ forming a ring is a single bond bonded to $L^2$. In other words, one of the ring(s) formed by $R^4$ to $R^6$, $R^9$ and $R^{10}$ is bonded to $L^2$. For instance, when $R^4$ and $R^9$ form a ring in the formula (11), $R^5$ or $R^6$ not forming a ring is a single bond bonded to $L^2$, or alternatively, the ring formed by $R^4$ and $R^9$ is bonded by a single bond to $L^2$ as shown in a formula (11A). $R^5$, $R^6$ and $X^{10}$ in the formula (11A) represent the same as $R^5$, $R^6$ and $X^{10}$ in the formula (11).

[Formula 9]

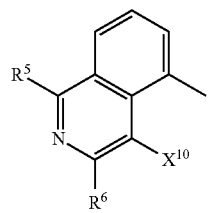

(11A)

In the formula (1), (1A) or (1B), $X^1$ to $X^8$ are preferably each independently CR.

In the formula (1), (1A) or (1B), Az represented by the formula (11) is preferably selected from a substituted or unsubstituted pyridine ring, substituted or unsubstituted pyrimidine ring, substituted or unsubstituted triazine ring, substituted or unsubstituted quinoline ring, substituted or unsubstituted isoquinoline ring, substituted or unsubstituted quinazoline ring, and substituted or unsubstituted phenanthroline ring.

Among the above, Az is more preferably selected from an unsubstituted pyridine ring, unsubstituted pyrimidine ring, unsubstituted triazine ring, unsubstituted quinoline ring, unsubstituted isoquinoline ring, unsubstituted quinazoline ring, and unsubstituted phenanthroline ring.

Further, Az is preferably a group represented by one of formulae (11-a) to (11-x), among which a group having a monocyclic structure without a fused ring is more preferable and a group represented by one of the formulae (11-a) to (11-g) is further preferable.

The group represented by one of the formulae (11-a) to (11-x) may further have a substituent. The substituent is exemplified by substituents meant by "substituted or unsubstituted" described later.

[Formula 10]

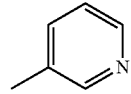

(11-a)

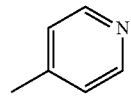

(11-b)

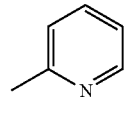

(11-c)

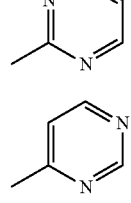

(11-d)

(11-e)

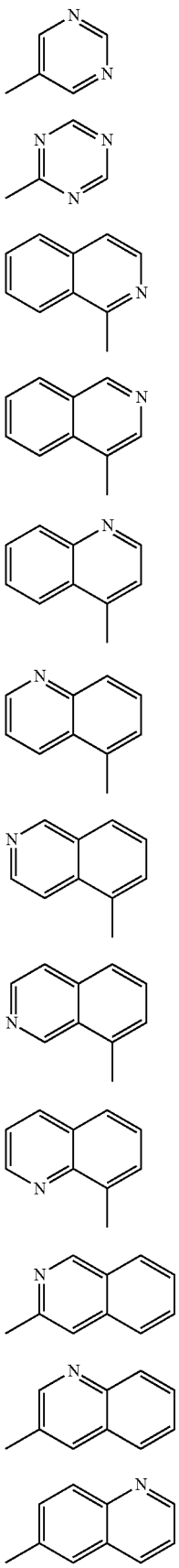
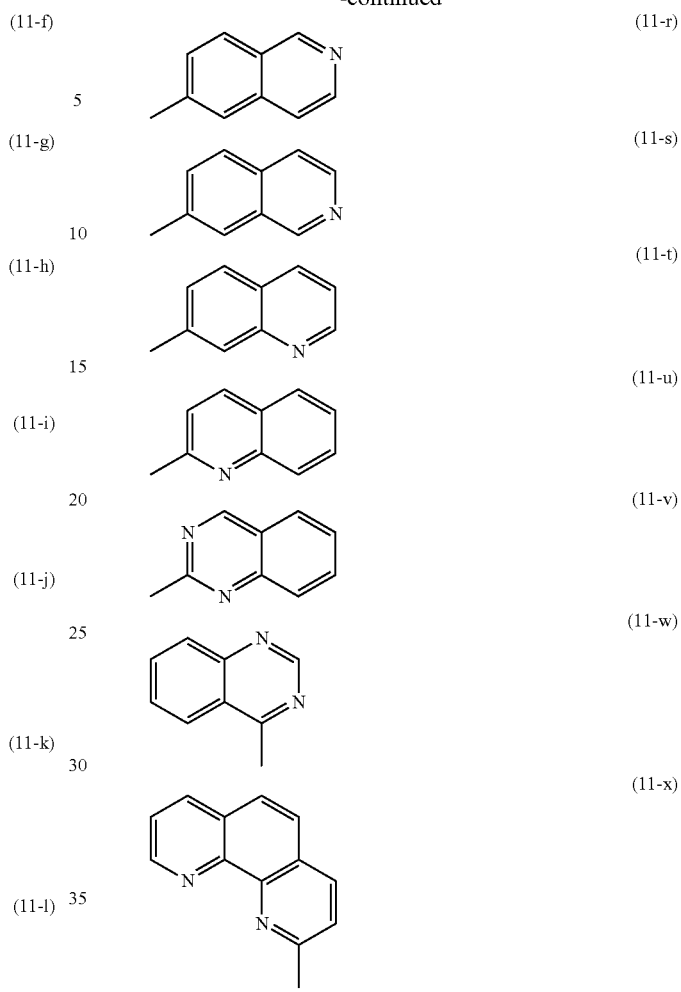

In the formulae (11-a) to (11-x), a single bond is bonded to $L^2$ of the formula (1), (1A) or (1B).

In the formula (11), it is preferable that $X^9$ is $CR^9$ and $X^{10}$ is $CR^{10}$. Specifically, Az is preferably a substituted or unsubstituted pyridine ring in the formulae (1), (1A) and (1B). Az is more preferably an unsubstituted pyridine ring represented by one of the formulae (11-a) to (11-c).

In the formulae (1), (1A) and (1B), it is preferable that n is 1 or 2 and m is 1.

The formula (1A) is preferably represented by a formula (12A-1) or (12A-2). The formula (1B) is preferably represented by a formula (12B-1) or (12B-2).

[Formula 11]

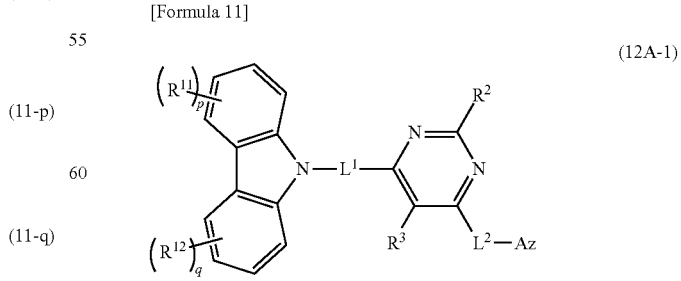

In the formula (12A-1), $L^1$, $L^2$, $R^2$, $R^3$ and Az respectively represent the same as $L^1$, $L^2$, $R^2$, $R^3$ and Az in the formula (1). Each of $R^{11}$ and $R^{12}$ is bonded to any carbon atom of a carbazolyl group. $R^{11}$ and $R^{12}$ represent the same as $R^3$ of the formula (1). p and q are 4. A plurality of $R^{11}$ and $R^{12}$ are mutually the same or different.

[Formula 12]

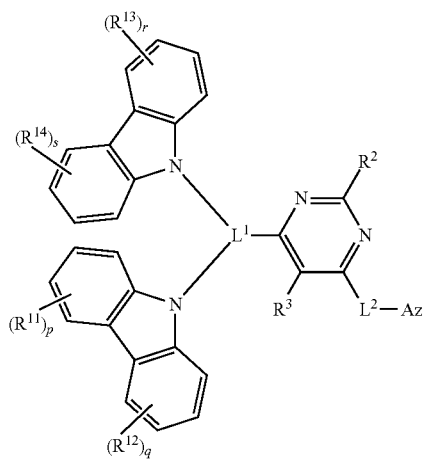

(12A-2)

In the formula (12A-2), $L^1$, $L^2$, $R^2$, $R^3$ and Az respectively represent the same as $L^1$, $L^2$, $R^2$, $R^3$ and Az in the formula (1). Each of $R^{11}$, $R^{12}$, $R^{13}$ and $R^{14}$ is bonded to any carbon atom of a carbazolyl group. $R^{11}$, $R^{12}$, $R^{13}$ and $R^{14}$ represent the same as $R^3$ of the formula (1). p, q, r and s are 4. A plurality of $R^{11}$, $R^{12}$, $R^{13}$ and $R^{14}$ are mutually the same or different.

[Formula 13]

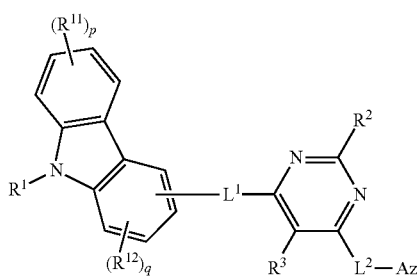

(12B-1)

In the formula (12B-1), $L^1$, $L^2$, $R^2$, $R^3$ and Az respectively represent the same as $L^1$, $L^2$, $R^2$, $R^3$ and Az in the formula (1). $L^1$ is bonded to any carbon atom of a carbazolyl group. $R^1$ represents the same as $R^3$ of the formula (1). Each of $R^{11}$ and $R^{12}$ is bonded to any carbon atom of a carbazolyl group. $R^{11}$ and $R^{12}$ represent the same as $R^3$ of the formula (1). p is 4. q is 3. A plurality of $R^{11}$ and $R^{12}$ are mutually the same or different.

[Formula 14]

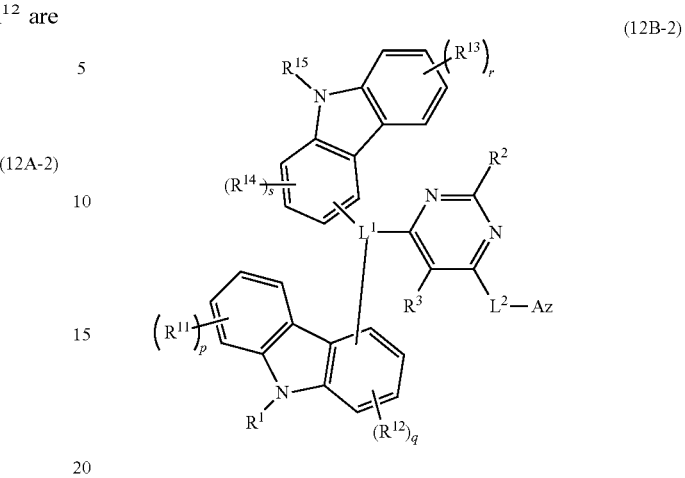

(12B-2)

In the formula (12B-2), $L^1$, $L^2$, $R^2$, $R^3$ and Az respectively represent the same as $L^1$, $L^2$, $R^2$, $R^3$ and Az in the formula (1). $L^1$ is bonded to any carbon atom of a carbazolyl group. $R^1$ and $R^{15}$ each independently represent the same as $R^3$ of the formula (1). Each of $R^{11}$, $R^{12}$, $R^{13}$ and $R^{14}$ is bonded to any carbon atom of a carbazolyl group. $R^{11}$, $R^{12}$, $R^{13}$ and $R^{14}$ represent the same as $R^3$ of the formula (1). p and r are 4. q and s are 3. A plurality of $R^{11}$, $R^{12}$, $R^{13}$ and $R^{14}$ are mutually the same or different.

In the exemplary embodiment, the compound represented by the formula (1) is preferably represented by the formula (1A), more preferably represented by one of the formulae (11A), (12A-1) and (12A-2).

$L^1$ is preferably a substituted or unsubstituted aromatic hydrocarbon group having 6 to 30 ring carbon atoms, more preferably represented by one of formulae (L-1a) to (L-1f).

The group represented by one of the formulae (L-1a) to (L-1f) may further have a substituent. The substituent is exemplified by the substituents meant by "substituted or unsubstituted" described later.

[Formula 15]

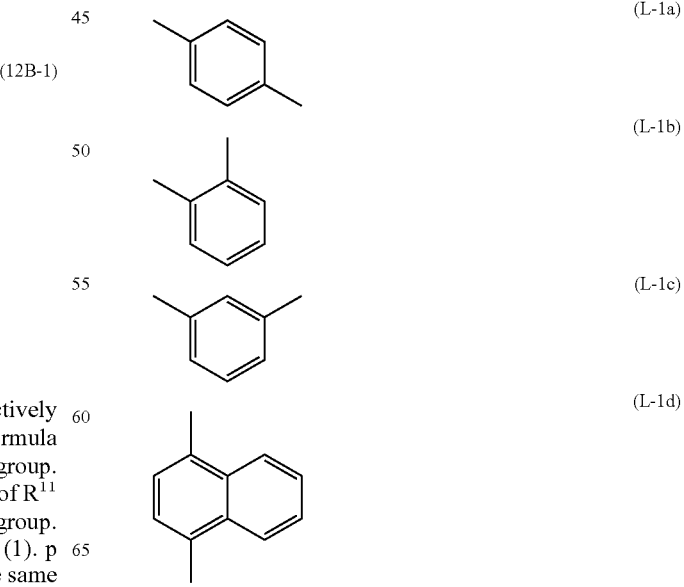

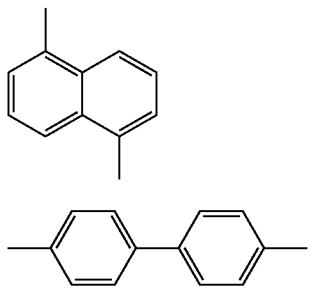
(L-1e)

(L-1f)

$L^1$ is preferably a substituted or unsubstituted benzene ring, more preferably represented by the formula (L-1a).

The formula (1) is preferably represented by a formula (13A) below.

[Formula 16]

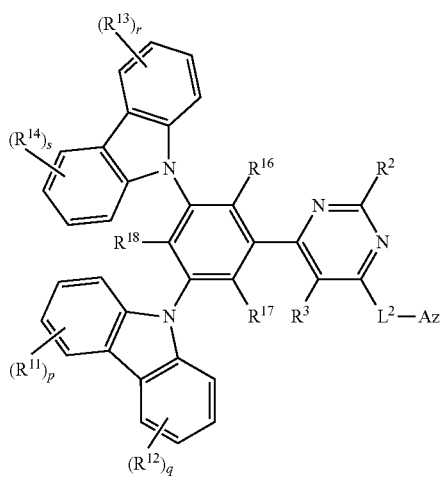
(13A)

In the formula (13A), $L^2$, $R^2$, $R^3$ and Az respectively represent the same as $L^2$, $R^2$, $R^3$ and Az in the formula (1). Each of $R^{11}$, $R^{12}$, $R^{13}$ and $R^{14}$ is bonded to any carbon atom of a carbazolyl group. $R^1$, $R^{12}$, $R^{13}$, $R^{14}$, $R^{16}$, $R^{17}$ and $R^{18}$ represent the same as $R^3$ of the formula (1). p, q, r and s are 4. A plurality of $R^{11}$, $R^{12}$, $R^{13}$ and $R^{14}$ are mutually the same or different.

The formula (1A) is also preferably represented by a formula (15A) below.

[Formula 17]

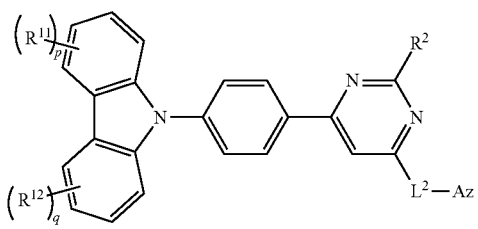
(15A)

In the formula (15A), $R^2$, $L^2$ and Az respectively represent the same as $R^2$, $L^2$ and Az in the formula (1). $R^{11}$ and $R^{12}$ each represent the same as $R^3$ of the formula (1). A plurality of $R^{11}$ are mutually the same or different. A plurality of $R^{12}$ are mutually the same or different. p and q are 4.

$L^2$ is preferably a substituted or unsubstituted aromatic hydrocarbon group having 6 to 30 ring carbon atoms or a substituted or unsubstituted heterocyclic group having 5 to 30 ring atoms. When $L^2$ is a substituted or unsubstituted heterocyclic group having 5 to 30 ring atoms, $L^2$ is preferably a dibenzofuran ring or a dibenzothiophene ring. $L^2$ is preferably a substituted or unsubstituted aromatic hydrocarbon group having 6 to 30 ring carbon atoms. The substituted or unsubstituted aromatic hydrocarbon group having 6 to 30 ring carbon atoms is preferably a substituted or unsubstituted benzene ring, a substituted or unsubstituted naphthalene ring or a substituted or unsubstituted biphenylene ring. $L^2$ is further preferably a group represented by one of formulae (L-2a) to (L-2f).

The group represented by one of the formulae (L-2a) to (L-2f) may further have a substituent. The substituent is exemplified by the substituents meant by "substituted or unsubstituted" described later.

[Formula 18]

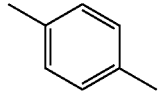
(L-2a)

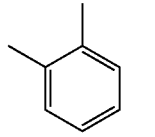
(L-2b)

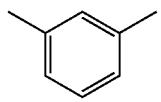
(L-2c)

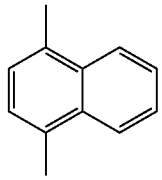
(L-2d)

(L-2e)

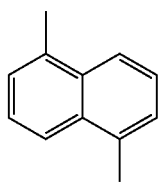
(L-2f)

$L^2$ is preferably a substituted or unsubstituted benzene ring. $L^2$ is more preferably represented by one of the formulae (L-2a) to (L-2c), further preferably represented by the formula (L-2a).

$R^2$ is preferably a substituted or unsubstituted aromatic hydrocarbon group having 6 to 30 ring carbon atoms, more preferably represented by one of formulae (R-2a) to (R-2e).

The group represented by one of the formulae (R-2a) to (R-2e) may further have a substituent. The substituent is exemplified by the substituents meant by "substituted or unsubstituted" described later.

[Formula 19]

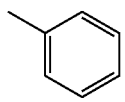
(R-2a)

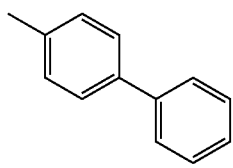
(R-2b)

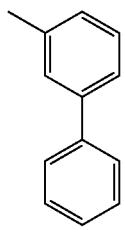
(R-2c)

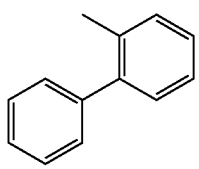
(R-2d)

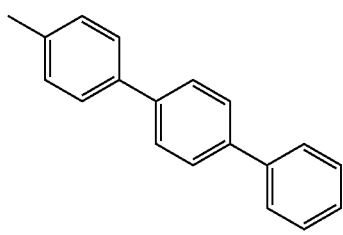
(R-2e)

$R^2$ is preferably a substituted or unsubstituted phenyl group, more preferably represented by the formula (R-2a).

The formula (15A) is preferably represented by a formula (16A) below.

[Formula 20]

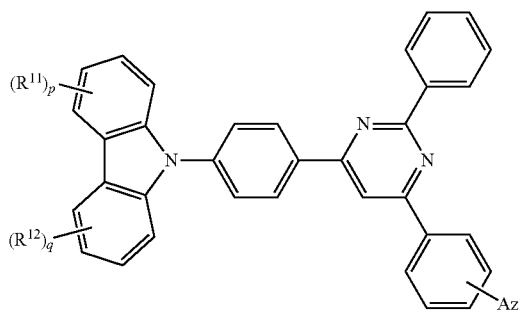
(16A)

In the formula (16A), Az represents the same as Az of the formula (1). $R^{11}$ and $R^{12}$ represent the same as $R^3$ of the formula (1). A plurality of $R^{11}$ are mutually the same or different. A plurality of $R^{12}$ are mutually the same or different. p and q are 4.

Next, each of the substituents described in the formulae (1), (1a), (1A), (1B), (13A), (15A) to (16A), (12A-1) to (12A-2) and (12B-1) to (12B-2) will be described.

Examples of the aromatic hydrocarbon group having 6 to 30 ring carbon atoms (occasionally referred to as an aryl group) in the exemplary embodiment are a phenyl group, biphenyl group, terphenyl group, naphthyl group, anthryl group, phenanthryl group, fluorenyl group, pyrenyl group, chrysenyl group, fluoranthenyl group, benz[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

The aromatic hydrocarbon group in the exemplary embodiment preferably has 6 to 20 ring carbon atoms, more preferably 6 to 12 ring carbon atoms. Among the aromatic hydrocarbon group, a phenyl group, biphenyl group, naphthyl group, phenanthryl group, terphenyl group, and fluorenyl group are further preferable. A carbon atom at a position 9 of each of 1-fluorenyl group, 2-fluorenyl group, 3-fluorenyl group and 4-fluorenyl group is preferably substituted by a substituted or unsubstituted alkyl group having 1 to 30 carbon atoms or a substituted or unsubstituted aryl group having 6 to 18 ring carbon atoms later described in the exemplary embodiment.

As the aromatic hydrocarbon group having 6 to 24 ring carbon atoms in a first cyclic structure of the exemplary embodiment, an aromatic hydrocarbon group having 6 to 24 ring carbon atoms among the above aromatic hydrocarbon group is usable.

In the exemplary embodiment, the heterocyclic group (occasionally referred to as heteroaryl group, heteroaromatic ring group or aromatic heterocyclic group) having 5 to 30 ring atoms preferably contains at least one atom selected from the group consisting of nitrogen, sulfur, oxygen, silicon, selenium atom and germanium atom, and more preferably contains at least one atom selected from the group consisting of nitrogen, sulfur and oxygen.

Examples of the heterocyclic group having 5 to 30 ring atoms in the exemplary embodiment are a pyridyl group, pyrimidinyl group, pyrazinyl group, pyridazynyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, and phenoxazinyl group.

The heterocyclic group in the exemplary embodiment preferably has 5 to 20 ring atoms, more preferably 5 to 14 ring atoms. Among the above heterocyclic group, a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-carbazolyl group, 2-carbazolyl group, 3-carbazolyl group, 4-carbazolyl group, and 9-carbazolyl group are further preferable. In the 1-carbazolyl group, 2-carbazolyl group, 3-carbazolyl group, and 4-carbazolyl group, a nitrogen atom at a position 9 is preferably substituted by a substituted or unsubstituted aromatic hydrocarbon group having 6 to 30 ring carbon atoms or a substituted or unsubstituted heterocyclic group having 5 to 30 ring atoms in the exemplary embodiment.

As the heterocyclic group having 6 to 24 ring atoms in the first cyclic structure of the exemplary embodiment, a heterocyclic group having 6 to 24 ring atoms among the above heterocyclic group is usable.

In the exemplary embodiment, the heterocyclic group may be a group derived from any one of partial structures represented by formulae (XY-1) to (XY-18).

[Formula 21]

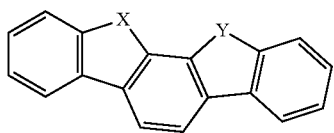
(XY-1)

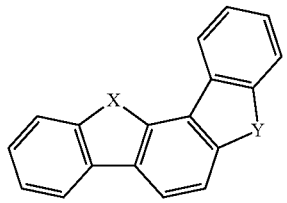
(XY-2)

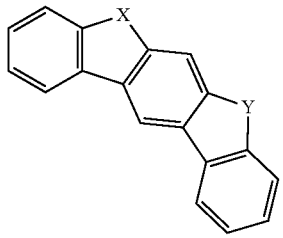
(XY-3)

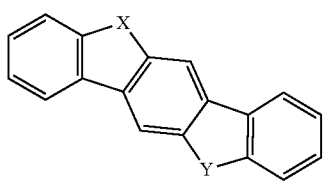
(XY-4)

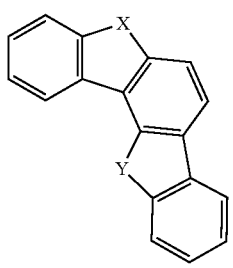
(XY-5)

[Formula 22]

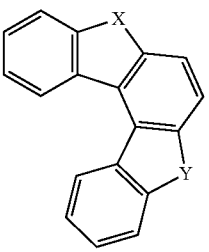
(XY-6)

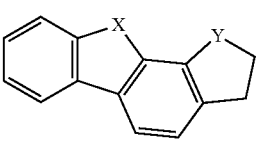
(XY-7)

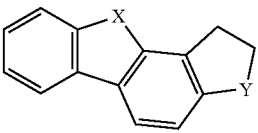
(XY-8)

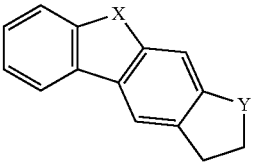
(XY-9)

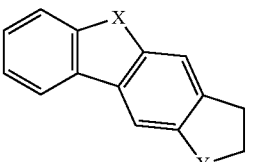
(XY-10)

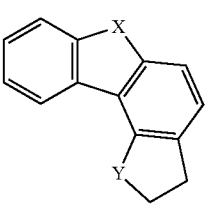
(XY-11)

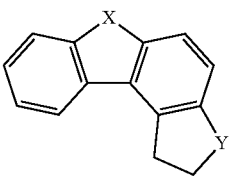
(XY-12)

[Formula 23]

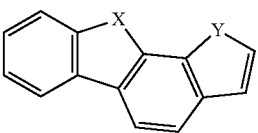
(XY-13)

(XY-14)

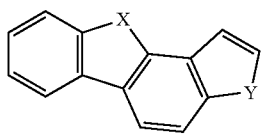

(XY-15)

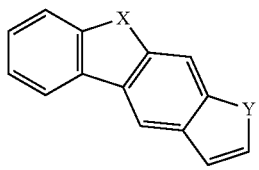

(XY-16)

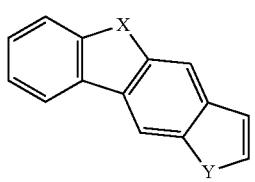

(XY-17)

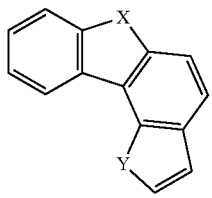

(XY-18)

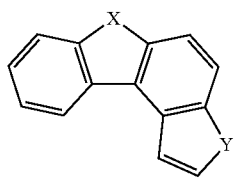

In the formulae (XY-1) to (XY-18), X and Y are each independently a hetero atom, and are preferably an oxygen atom, sulfur atom, selenium atom, silicon atom or germanium atom. The partial structures represented by the formulae (XY-1) to (XY-18) may each be bonded in any position to be a heterocyclic group, which may be substituted.

In the exemplary embodiment, examples of the substituted or unsubstituted carbazolyl group may include a group in which a carbazole ring is further fused with a ring(s) as shown in the following formulae. Such a group may be substituted. The group may be bonded in any position as desired.

[Formula 24]

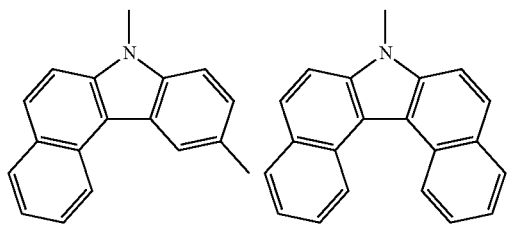

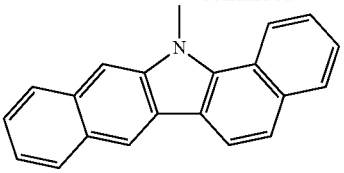

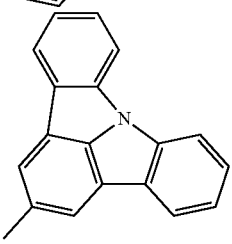

The alkyl group having 1 to 30 carbon atoms in the exemplary embodiment may be linear, branched or cyclic. Examples of the linear or branched alkyl group include: a methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, amyl group, isoamyl group, 1-methylpentyl group, 2-methylpentyl group, 1-pentylhexyl group, 1-butylpentyl group, 1-heptyloctyl group, and 3-methylpentyl group.

The linear or branched alkyl group in the exemplary embodiment preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group, n-hexyl group, amyl group, isoamyl group and neopentyl group are further preferable.

Examples of the cycloalkyl group in the exemplary embodiment are a cyclopropyl group, cyclobutyl group, cyclopentyl group, cyclohexyl group, 4-metylcyclohexyl group, adamantyl group and norbornyl group. The cycloalkyl group preferably has 3 to 10 ring carbon atoms, more preferably 5 to 8 ring carbon atoms. Among the cycloalkyl group, a cyclopentyl group and a cyclohexyl group are further preferable.

A halogenated alkyl group provided by substituting an alkyl group with a halogen atom is exemplified by one provided by substituting an alkyl group having 1 to 30 carbon atoms with one or more halogen groups. Specific examples of the above halogenated alkyl group are a fluoromethyl group, difluoromethyl group, trifluoromethyl group, fluoroethyl group, trifluoromethylmethyl group, trifluoroethyl group and pentafluoroethyl group.

The alkenyl group having 2 to 30 carbon atoms in the exemplary embodiment may be linear, branched or cyclic. Examples of the alkenyl group are a vinyl group, propenyl group, butenyl group, oleyl group, eicosapentaenyl group, docosahexaenyl group, styryl group, 2,2-diphenylvinyl group, 1,2,2-triphenylvinyl group, 2-phenyl-2-propenyl group, cyclopentadienyl group, cyclopentenyl group, cyclohexenyl group and cyclohexadienyl group.

The alkynyl group having 2 to 30 carbon atoms may be linear, branched or cyclic. Examples of the alkynyl group having 2 to 30 carbon atoms are an ethynyl group, a propynyl group and a 2-phenylethynyl group.

The alkylsilyl group having 3 to 30 carbon atoms in the exemplary embodiment is exemplified by a trialkylsilyl group having the above examples of the alkyl group having 1 to 30 carbon atoms. Specific examples of the alkylsilyl group are a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups in the trialkylsilyl group may be the same or different.

Examples of the arylsilyl group having 6 to 60 ring carbon atoms in the exemplary embodiment are a dialkylarylsilyl group, alkyldiarylsilyl group and triarylsilyl group.

The dialkylarylsilyl group is exemplified by a dialkylarylsilyl group having two of the examples of the alkyl group having 1 to 30 carbon atoms and one of the examples of the aromatic hydrocarbon group having 6 to 30 ring carbon atoms. The dialkylarylsilyl group preferably has 8 to 30 carbon atoms.

The alkyldiarylsilyl group is exemplified by a alkyldiarylsilyl group having one of the examples of the alkyl group having 1 to 30 carbon atoms and two of the examples of the aromatic hydrocarbon group having 6 to 30 ring carbon atoms. The alkyldiarylsilyl group preferably has 13 to 30 carbon atoms.

The triarylsilyl group is exemplified by a triarylsilyl group having three of the examples of the aromatic hydrocarbon group having 6 to 30 ring carbon atoms. The triarylsilyl group preferably has 18 to 30 carbon atoms.

The alkoxy group having 1 to 30 carbon atoms in the exemplary embodiment is represented by $-OZ_1$. $Z_1$ is exemplified by the above alkyl group having 1 to 30 carbon atoms. Examples of the alkoxy group are a methoxy group, ethoxy group, propoxy group, butoxy group, pentyloxy group and hexyloxy group.

A halogenated alkoxy group provided by substituting an alkoxy group with a halogen atom is exemplified by a group provided by substituting the alkoxy group having 1 to 30 carbon atoms with one or more halogen groups.

The aryloxy group having 6 to 30 ring carbon atoms in the exemplary embodiment is represented by $-OZ_2$. $Z_2$ is exemplified by the above aromatic hydrocarbon group having 6 to 30 ring carbon atoms or a later-described monocyclic group and fused ring group. The aryloxy group is exemplified by a phenoxy group.

The alkylamino group having 2 to 30 carbon atoms in the exemplary embodiment is represented by $-NHR_V$ or $-N(R_V)_2$. $R_V$ is exemplified by the alkyl group having 1 to 30 carbon atoms.

The arylamino group having 6 to 60 ring carbon atoms in the exemplary embodiment is represented by $-NHR_W$ or $-N(R_W)_2$. $R_W$ is exemplified by the above aromatic hydrocarbon group having 6 to 30 ring carbon atoms.

The alkylthio group having 1 to 30 carbon atoms in the exemplary embodiment is represented by $-SR_V$. $R_V$ is exemplified by the alkyl group having 1 to 30 carbon atoms.

The arylthio group having 6 to 30 ring carbon atoms is represented by $-SR_W$. $R_W$ is exemplified by the above aromatic hydrocarbon group having 6 to 30 ring carbon atoms.

Examples of the halogen atom in the exemplary embodiment include a fluorine atom, chlorine atom, bromine tom and iodine atom, among which a fluorine atom is preferable.

In the exemplary embodiment, examples of the multiple linking group including bonded 2 to 4 groups selected from the above aromatic hydrocarbon groups, the multiple linking group including bonded 2 to 4 groups selected from the above heterocyclic groups, or the multiple linking group including bonded 2 to 4 groups selected from the above aromatic hydrocarbon groups and heterocyclic groups include a divalent group including bonded 2 to 4 groups selected from the above aromatic hydrocarbon groups and heterocyclic groups. Examples of the multiple linking group including 2 to 4 groups selected from the above aromatic hydrocarbon groups and heterocyclic groups include a heterocyclic group-aromatic hydrocarbon group, aromatic hydrocarbon group-heterocyclic group, aromatic hydrocarbon group-heterocyclic group-aromatic hydrocarbon group, heterocyclic group-aromatic hydrocarbon group-heterocyclic group, aromatic hydrocarbon group-heterocyclic group-aromatic hydrocarbon group-heterocyclic group, and heterocyclic group-aromatic hydrocarbon group-heterocyclic group-aromatic hydrocarbon group. Among the above, divalent groups including one of the above aromatic hydrocarbon groups and one of the above heterocyclic groups, i.e., heterocyclic group-aromatic hydrocarbon group and aromatic hydrocarbon group-heterocyclic group, are preferable. It should be noted that specific examples of the aromatic hydrocarbon group and the heterocyclic group in the multiple linking group include the above groups described as the aromatic hydrocarbon group and the heterocyclic group.

In the exemplary embodiment, the number of carbon atoms forming a ring (also referred to as ring carbon atoms) means the number of carbon atoms included in atoms forming the ring itself of a compound in which the atoms are bonded to form the ring (e.g., a monocyclic compound, a fused ring compound, a cross-linked compound, a carbocyclic compound, and a heterocyclic compound). When the ring is substituted by a substituent, carbon atom(s) included in the substituent is not counted as the ring carbon atoms. The same applies to the "ring carbon atoms" described below, unless particularly noted. For instance, a benzene ring has 6 ring carbon atoms, a naphthalene ring has 10 ring carbon atoms, a pyridinyl group has 5 ring carbon atoms, and a furanyl group has 4 ring carbon atoms. When a benzene ring or a naphthalene ring is substituted, for instance, by an alkyl group, the carbon atoms of the alkyl group are not counted as the ring carbon atoms. For instance, when a fluorene ring (inclusive of a spirofluorene ring) is bonded as a substituent to a fluorene ring, the carbon atoms of the fluorene ring as a substituent are not counted as the ring carbon atoms.

In the exemplary embodiment, the number of atoms forming a ring (also referred to as ring atoms) means the number of atoms forming the ring itself of a compound in which the atoms are bonded to form the ring (e.g., a monocyclic compound, a fused ring compound, a cross-linked compound, a carbocyclic compound, and a heterocyclic compound). Atom(s) not forming the ring (e.g., hydrogen atom(s) for saturating the valence of the atom which forms the ring) and atom(s) in a substituent by which the ring is substituted are not counted as the ring atoms. The same applies to the "ring atoms" described below, unless particularly noted. For instance, a pyridine ring has 6 ring atoms, a quinazoline ring has 10 ring atoms, and a furan ring has 5 ring atoms. Hydrogen atoms respectively bonded to carbon atoms of the pyridine ring or the quinazoline ring and atoms forming a substituent are not counted as the ring atoms. For instance, when a fluorene ring (inclusive of a spirofluorene ring) is bonded as a substituent to a fluorene ring, the atoms of the fluorene ring as a substituent are not included in the ring atoms.

Herein, a hydrogen atom includes isotope having different numbers of neutrons, specifically, protium, deuterium and tritium.

Moreover, herein, examples of a substituent in "substituted or unsubstituted" are the above-described aromatic hydrocarbon group, heterocyclic group, alkyl group (linear or branched alkyl group, cycloalkyl group, haloalkyl group), alkoxy group, aryloxy group, aralkyl group, haloalkoxy group, alkylsilyl group, dialkylarylsilyl group, alkyldiarylsilyl group, triarylsilyl group, halogen atom, cyano group, hydroxyl group, nitro group and carboxy group. In addition, the alkenyl group and alkynyl group are also usable.

Among the above substituents, the aromatic hydrocarbon group, heterocyclic group, alkyl group, halogen atom, alkylsilyl group, arylsilyl group and cyano group are preferable and the specific preferable substituents described in each of the substituents are further preferable.

"Unsubstituted" in "substituted or unsubstituted" means that a group is not substituted by the above-described substituents but bonded with a hydrogen atom.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of a substituted ZZ group. "YY" is larger than "XX" and each of "XX" and "YY" represents an integer of 1 or more.

In the exemplary embodiment, "XX to YY atoms" in the description of "substituted or unsubstituted ZZ group having XX to YY atoms" represent atoms of an unsubstituted ZZ group and does not include atoms of a substituent(s) of a substituted ZZ group. "YY" is larger than "XX" and each of "XX" and "YY" represents an integer of 1 or more.

The same description as the above applies to "substituted or unsubstituted" in the following compound or a partial structure thereof.

In the formula (1), (1A), (1B), (12A-1), (12A-2), (12B-1), (12B-2), (13A), and (15A), when $R^2$ has a substituent, specifically, the substituent being a substituted XX group is a halogen atom, hydroxyl group, cyano group, nitro group, carboxy group, substituted or unsubstituted alkyl group having 1 to 30 carbon atoms, substituted or unsubstituted alkenyl group having 1 to 30 carbon atoms, substituted or unsubstituted alkynyl group having 1 to 30 carbon atoms, substituted or unsubstituted alkylsilyl group having 3 to 30 carbon atoms, substituted or unsubstituted arylsilyl group having 6 to 60 ring carbon atoms, substituted or unsubstituted alkoxy group having 1 to 30 carbon atoms, substituted or unsubstituted aryloxy group having 6 to 30 ring carbon atoms, substituted or unsubstituted arylthio group having 6 to 30 ring carbon atoms, substituted or unsubstituted oxygen-containing heterocyclic group having 5 to 30 ring carbon atoms, substituted or unsubstituted sulfur-containing heterocyclic group having 5 to 30 ring carbon atoms, or substituted or unsubstituted aromatic hydrocarbon group having 6 to 30 ring carbon atoms. When the aryloxy group and the arylthio group have substituents, adjacent ones of the substituents are bonded to form a ring or are not bonded.

Specific examples of the compound represented by the formula (1) are shown below, but the invention is not limited thereto.

[Formula 25]

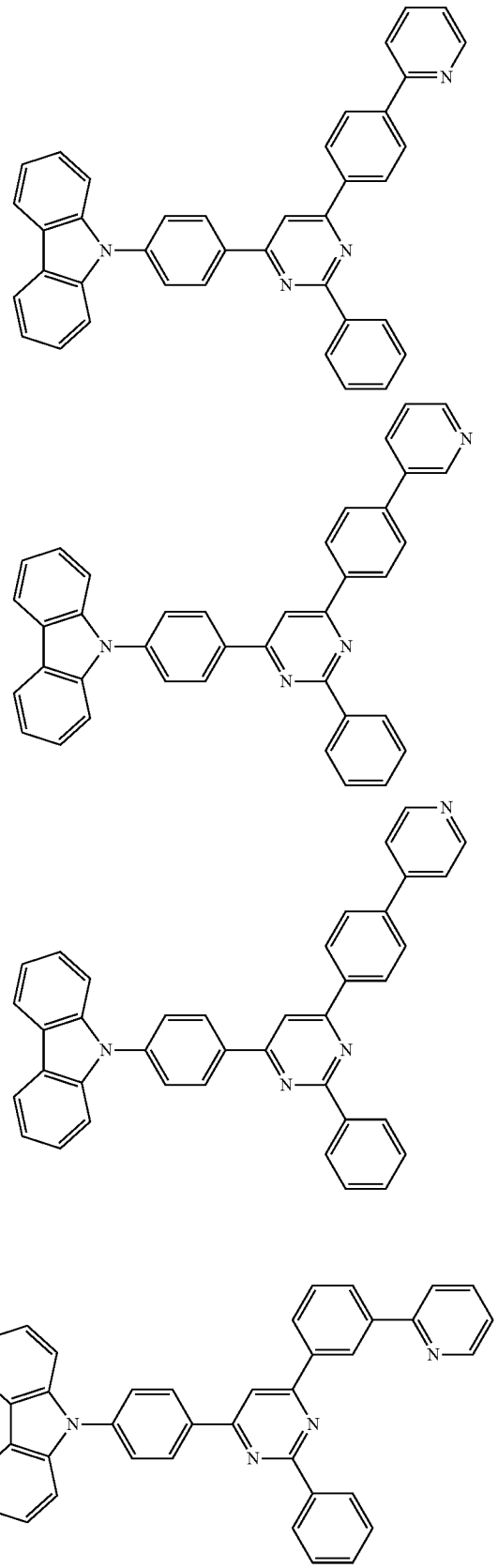

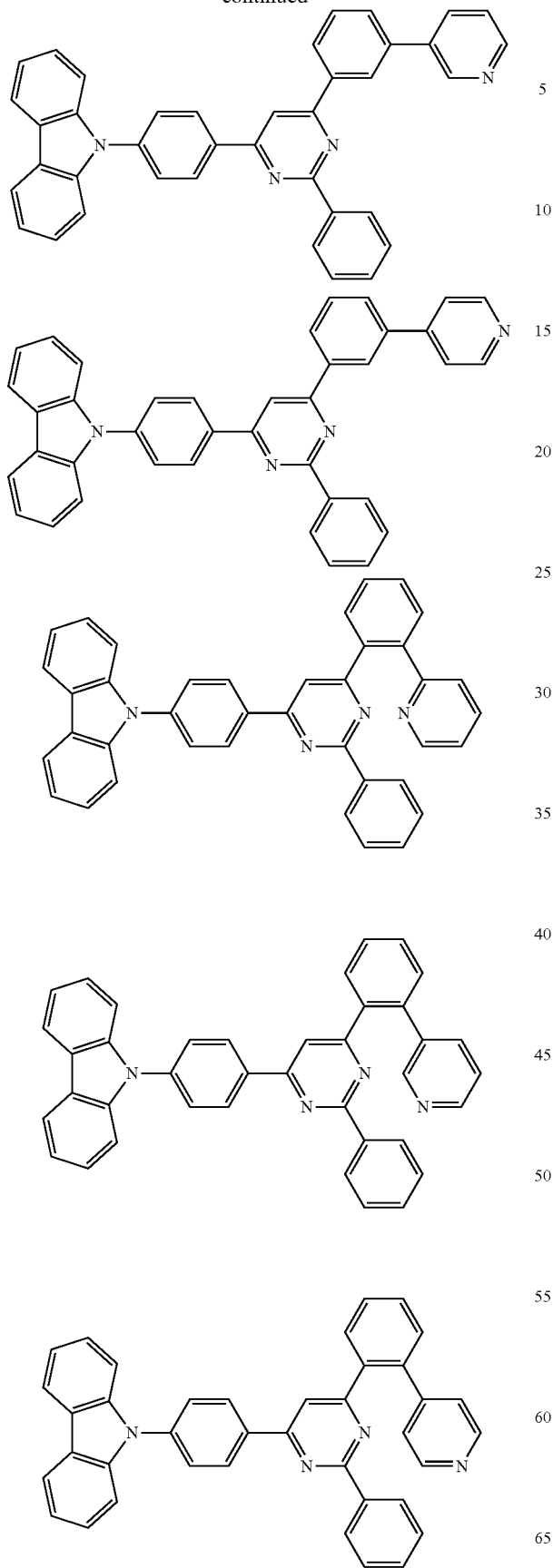
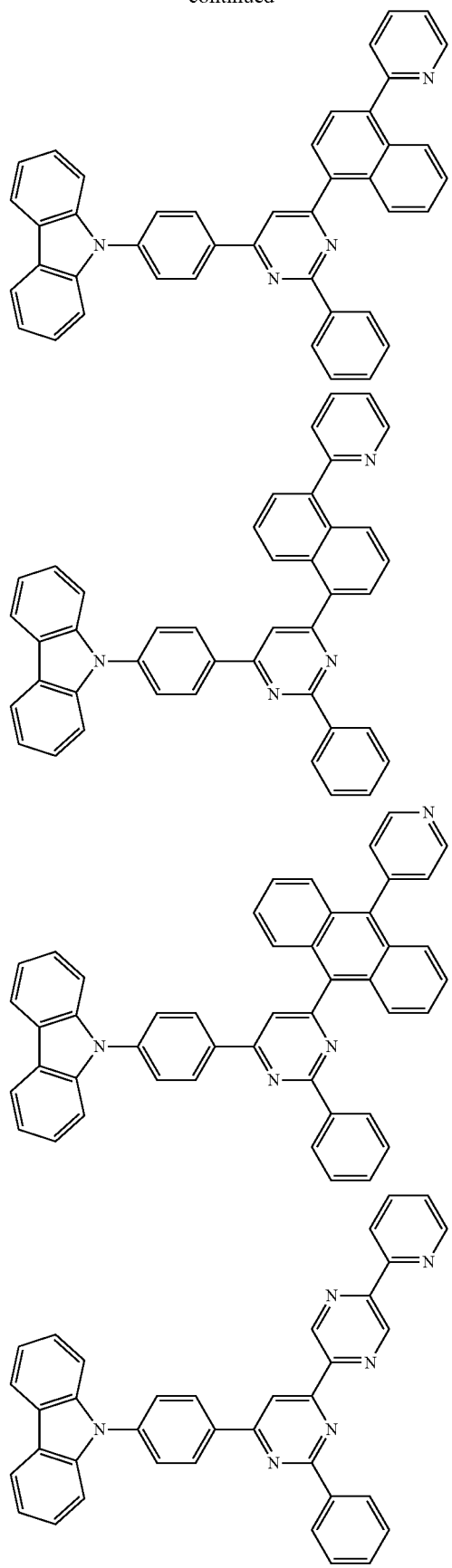

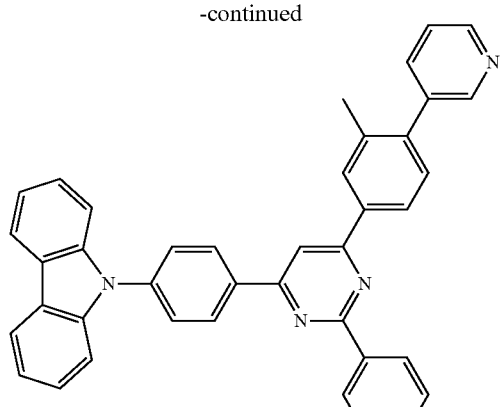
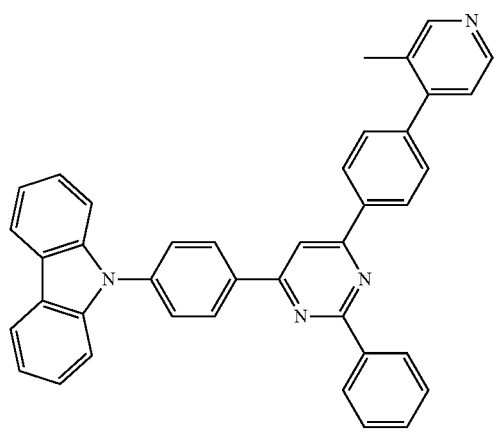
[Formula 26]
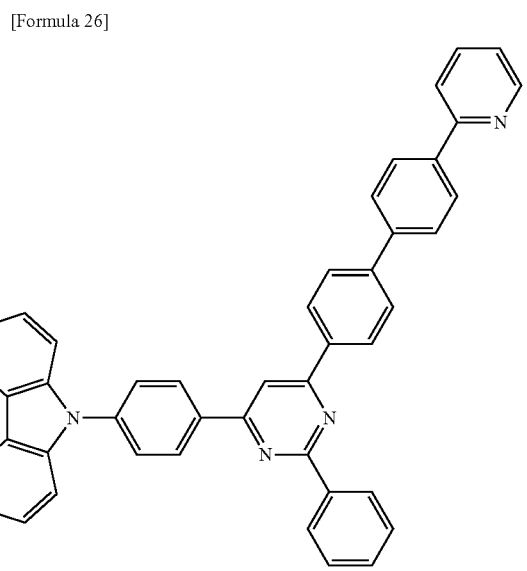
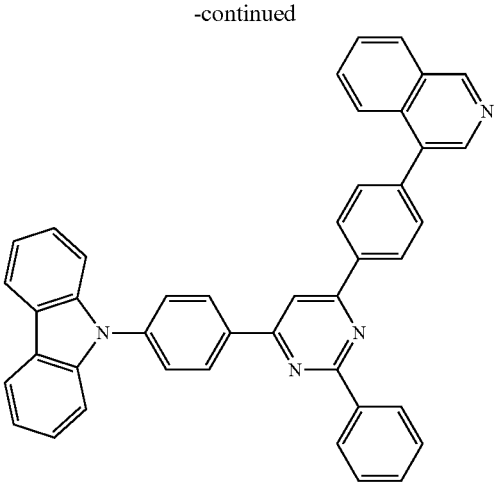
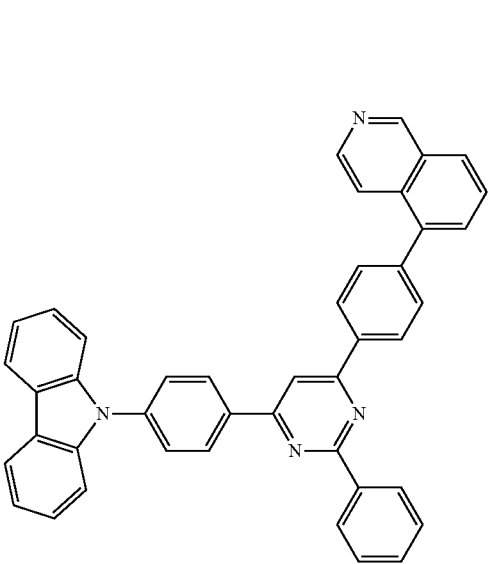

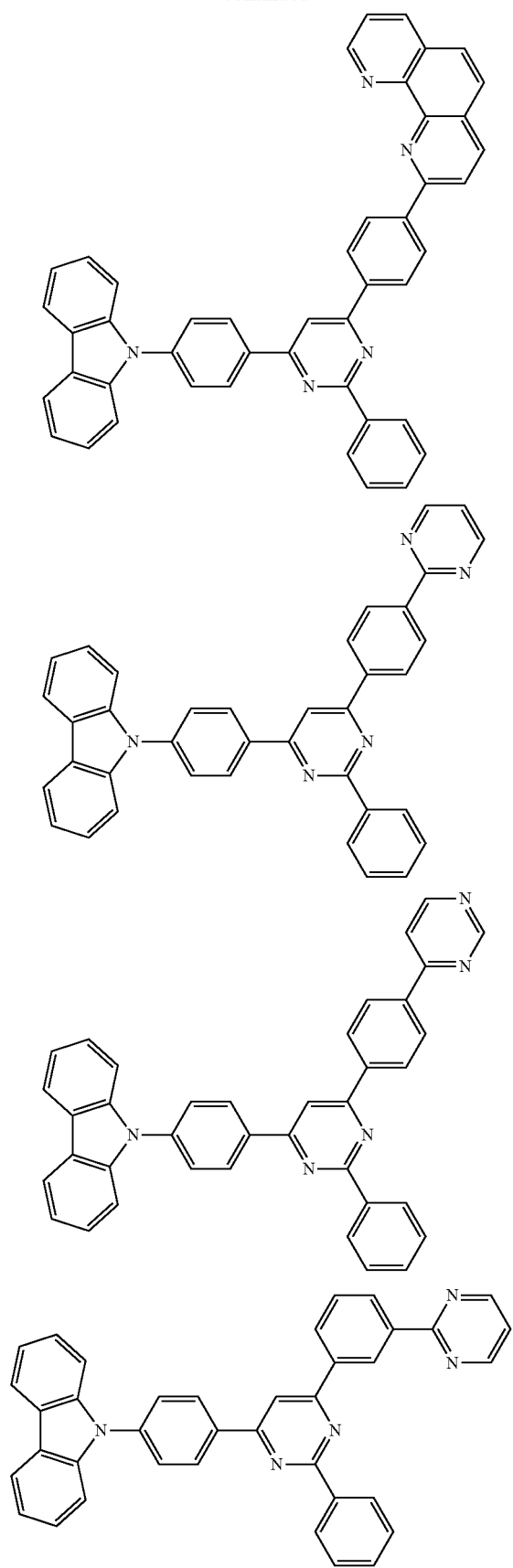
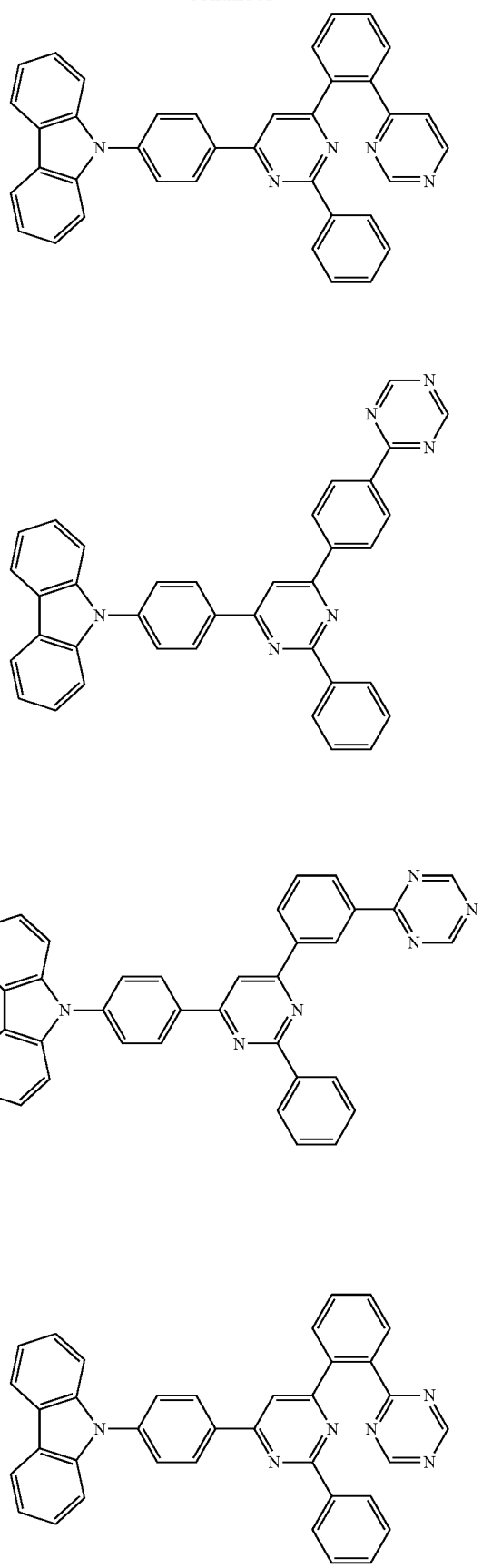

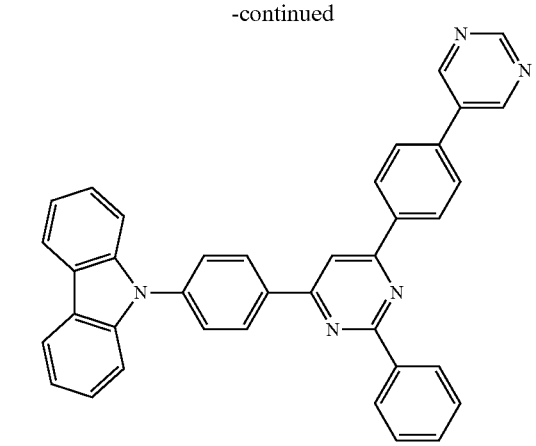
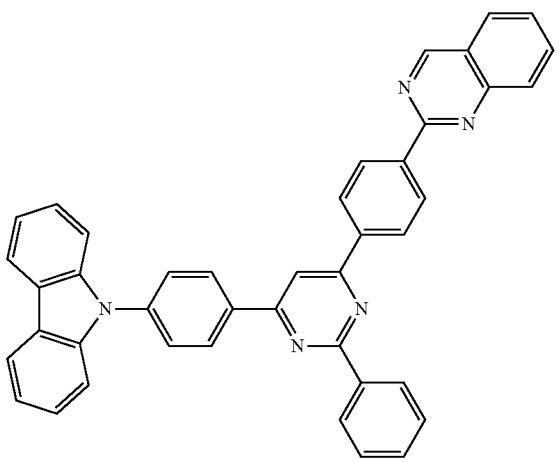
[Formula 27]
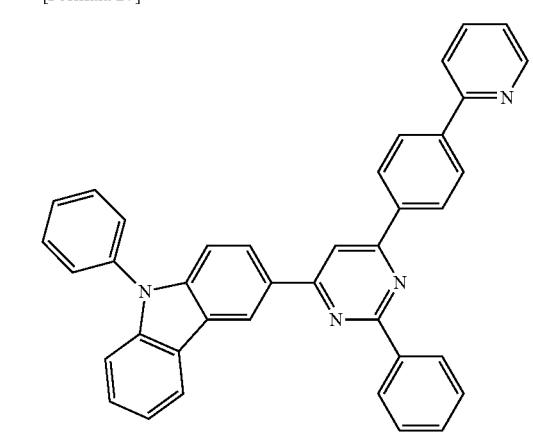
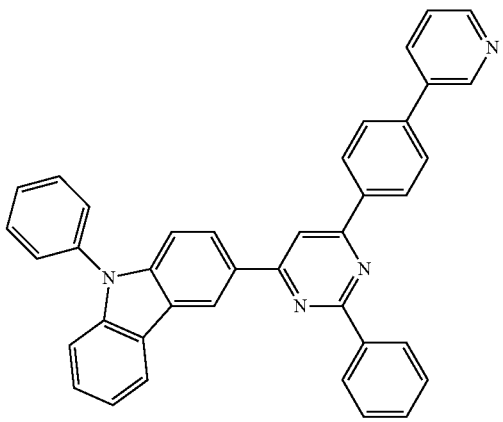
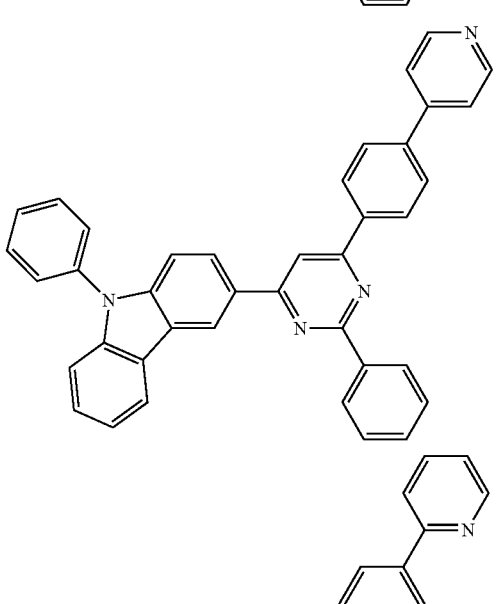
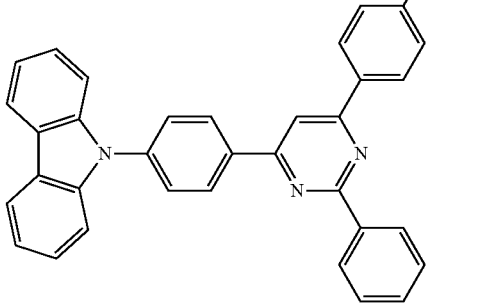
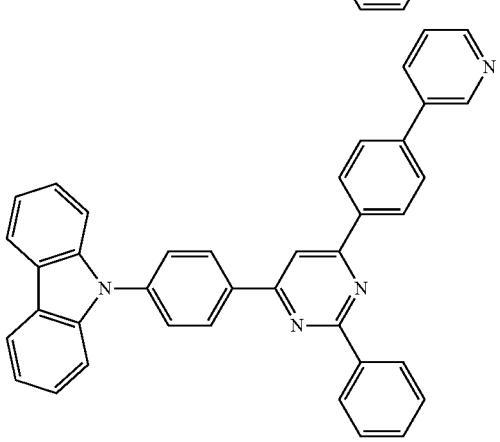

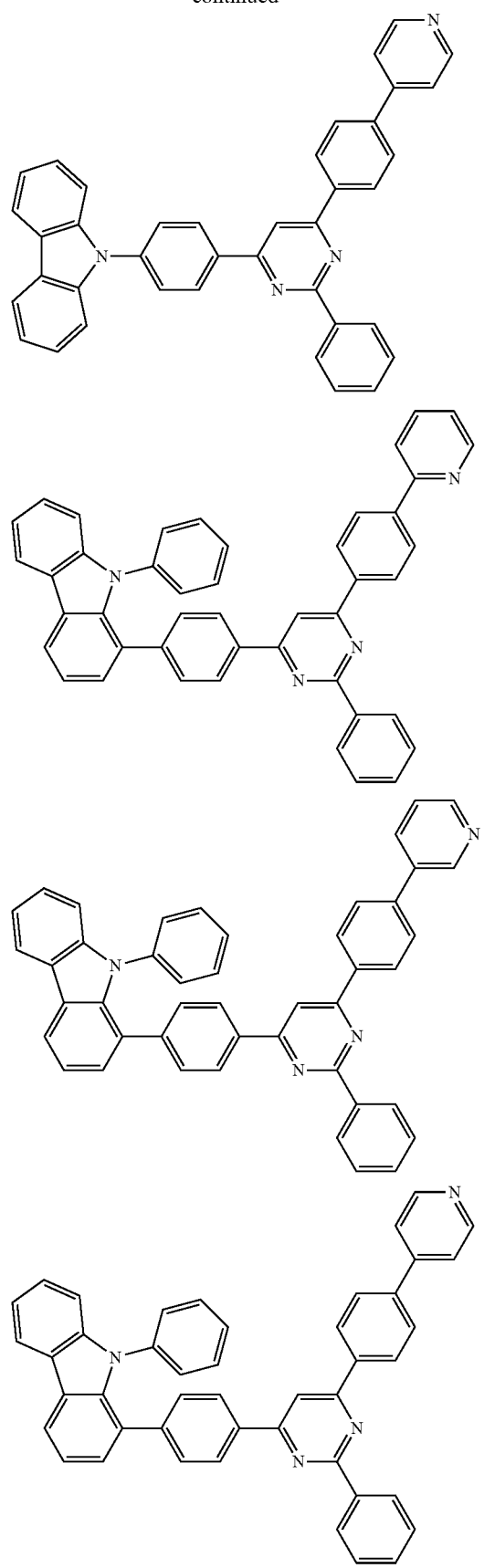
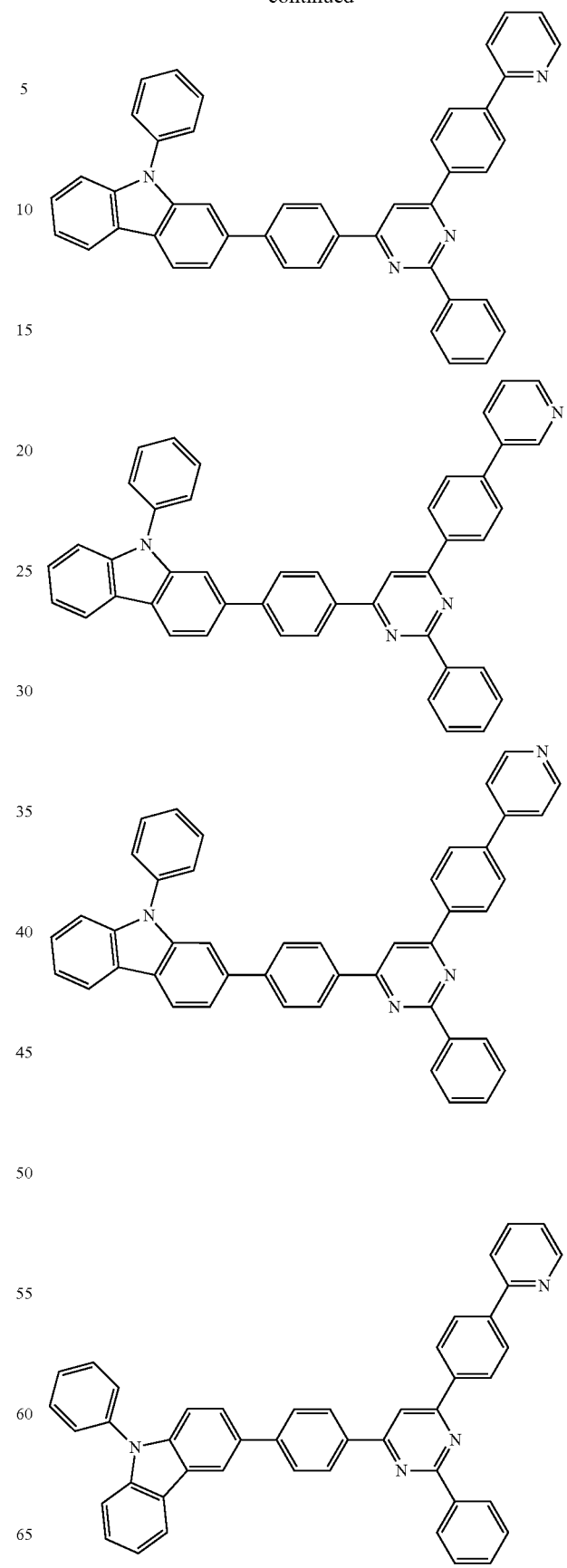

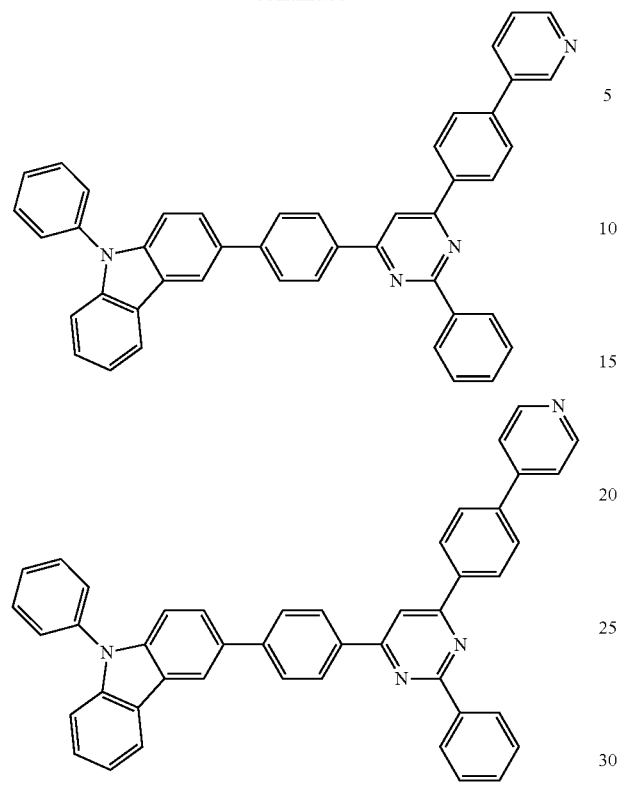
[Formula 28]
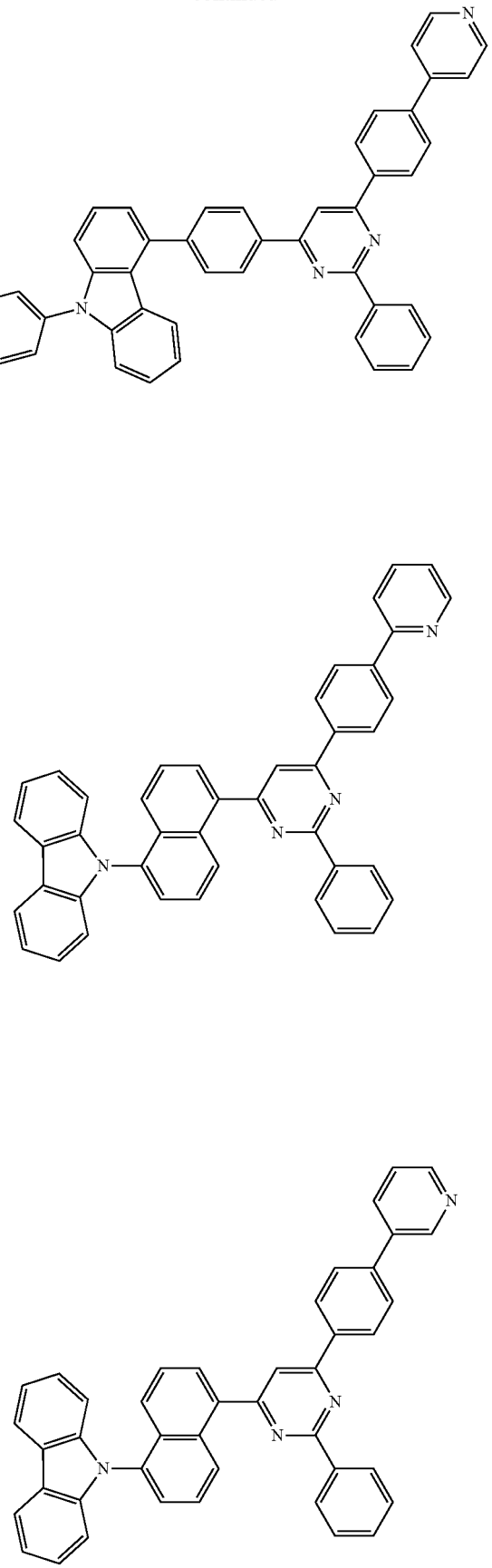

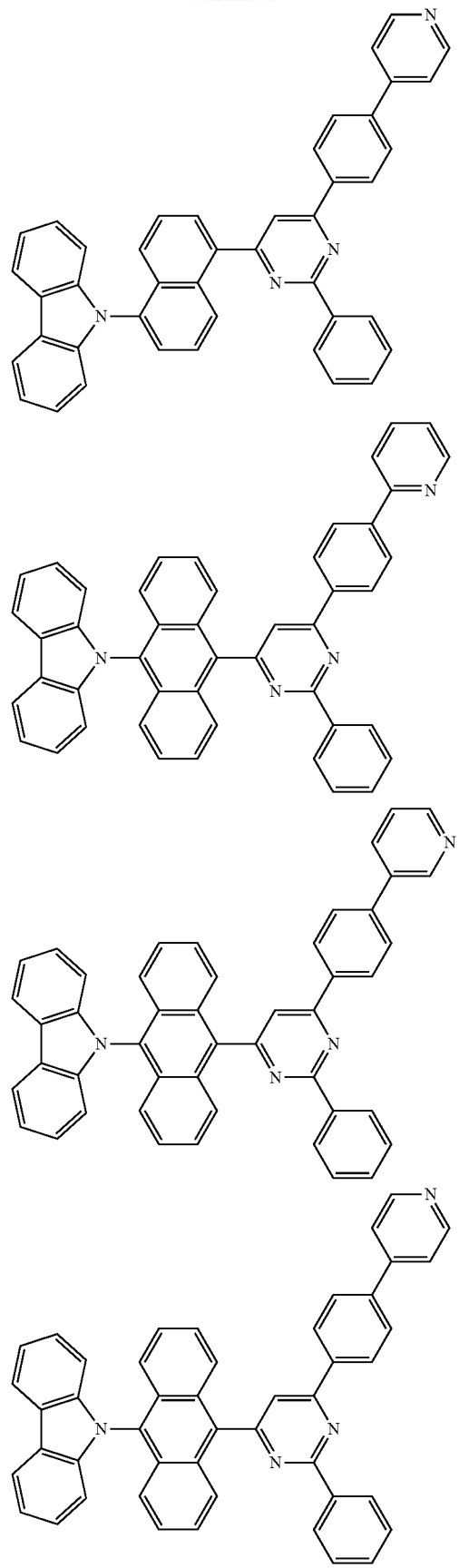
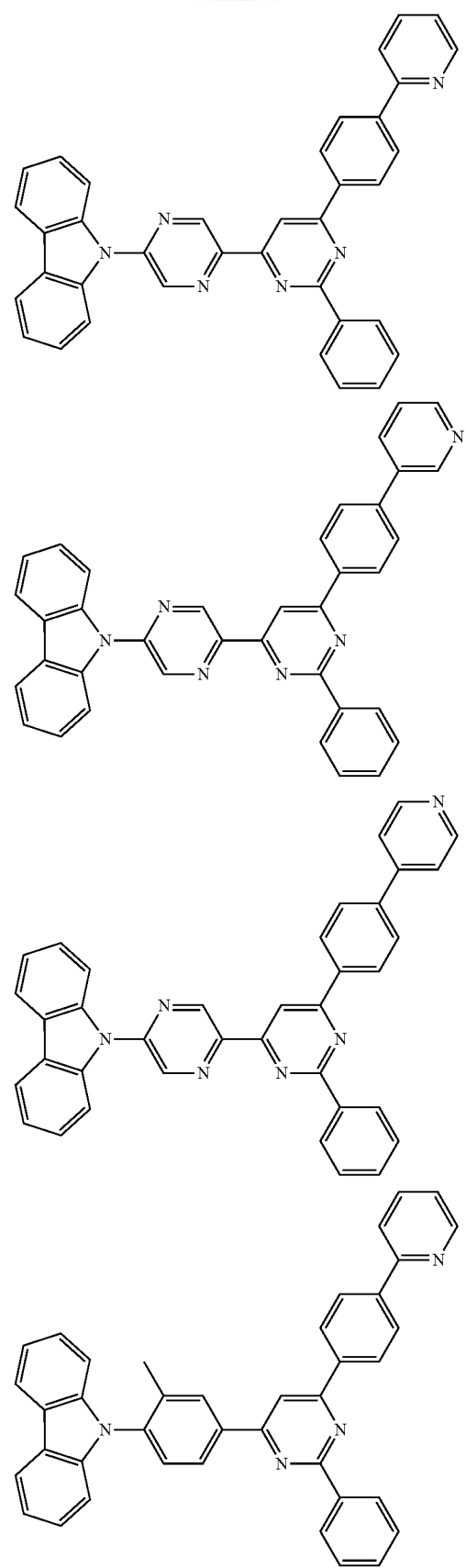

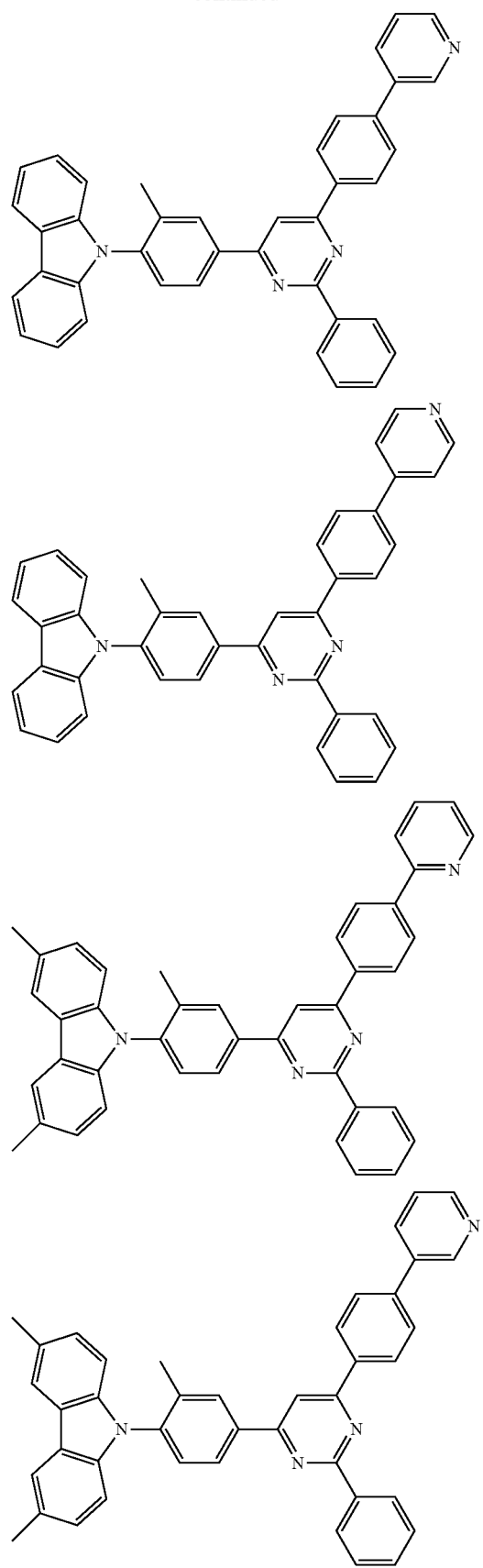
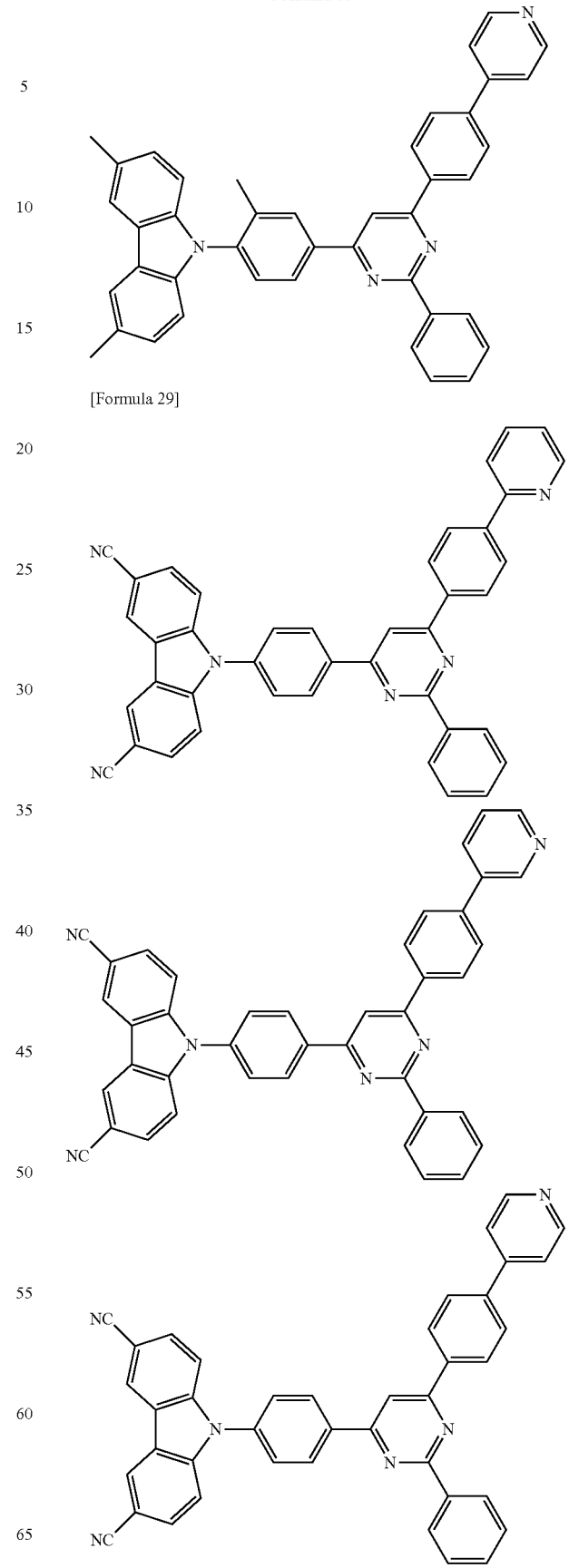
[Formula 29]

41
-continued
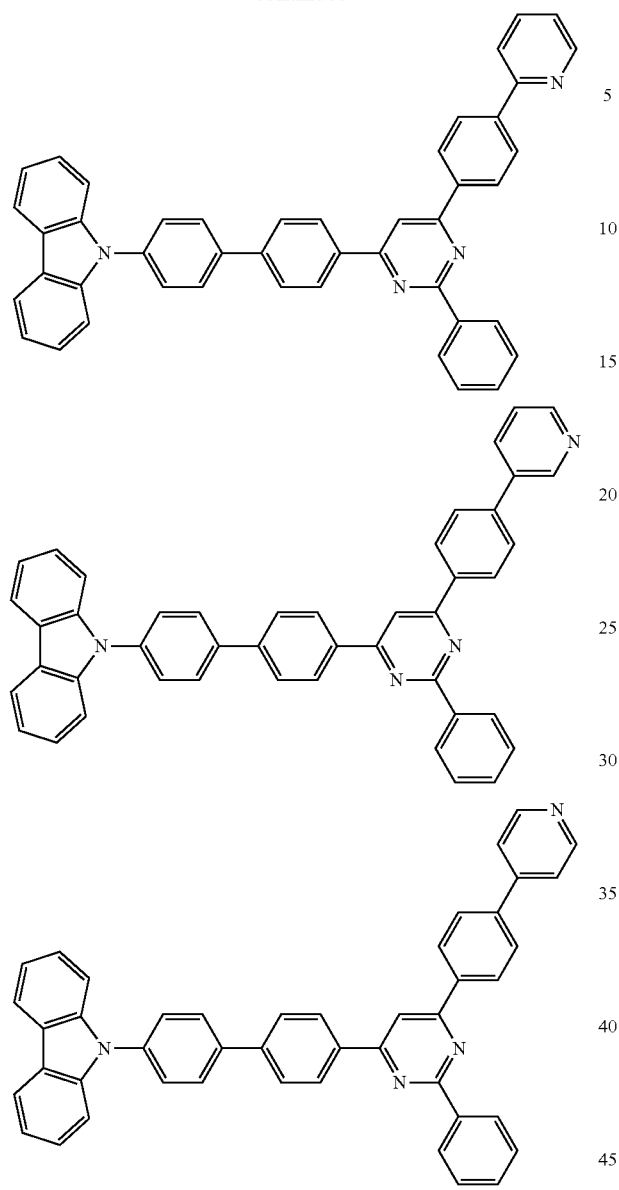
42
-continued
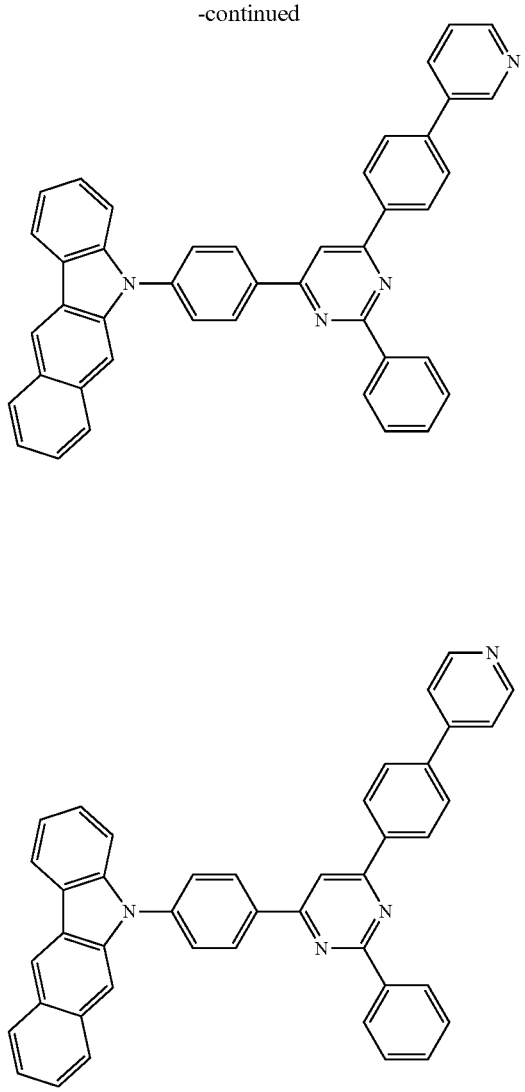
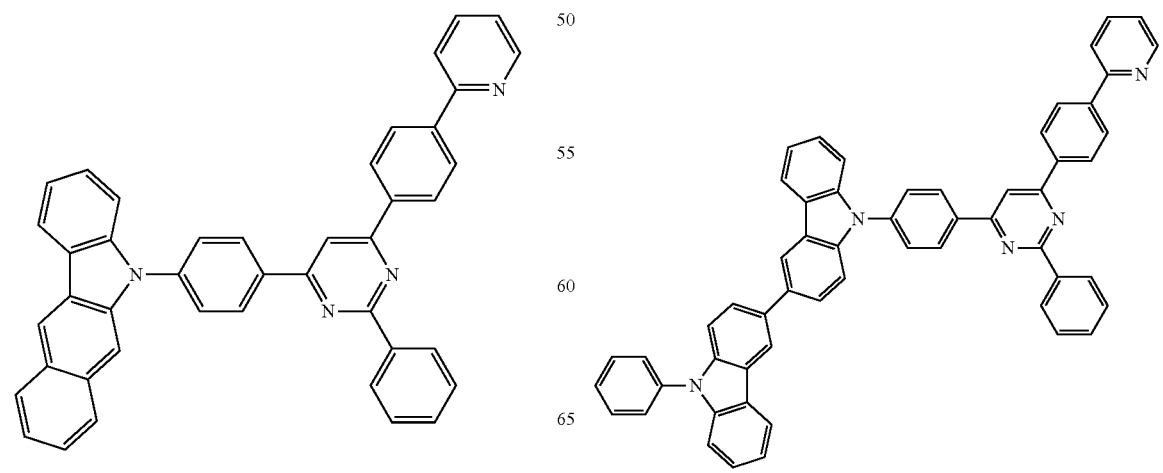

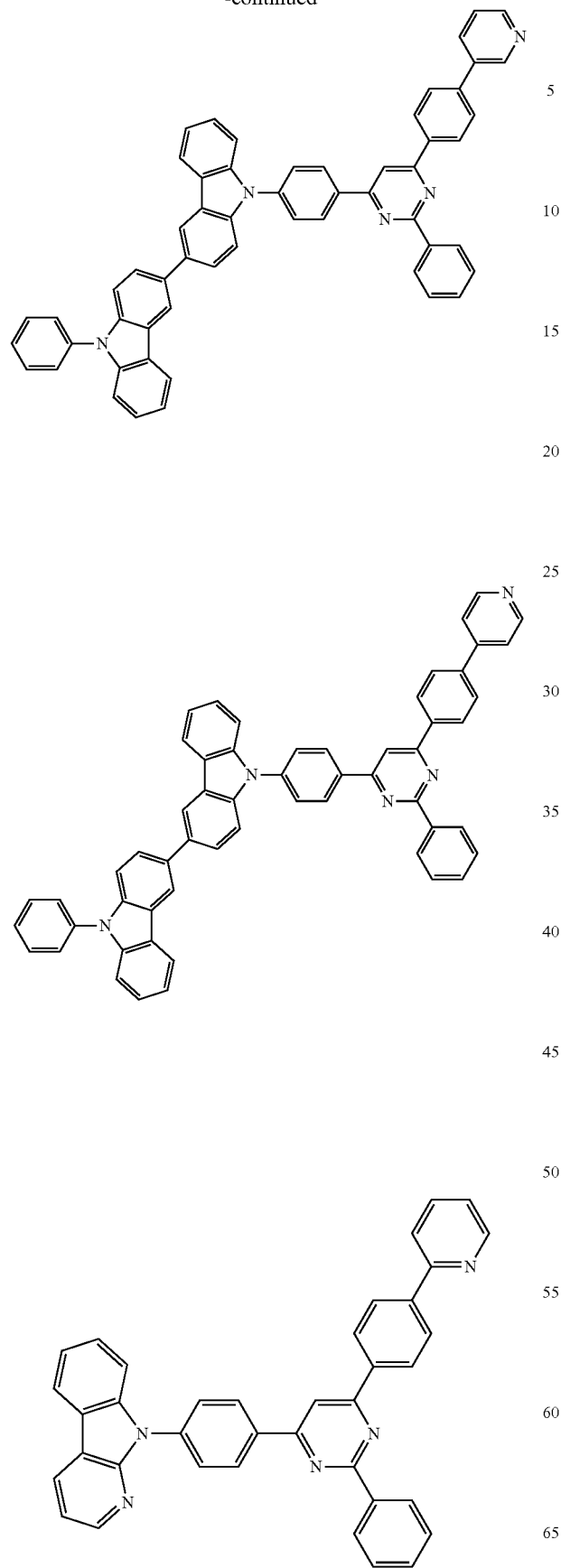
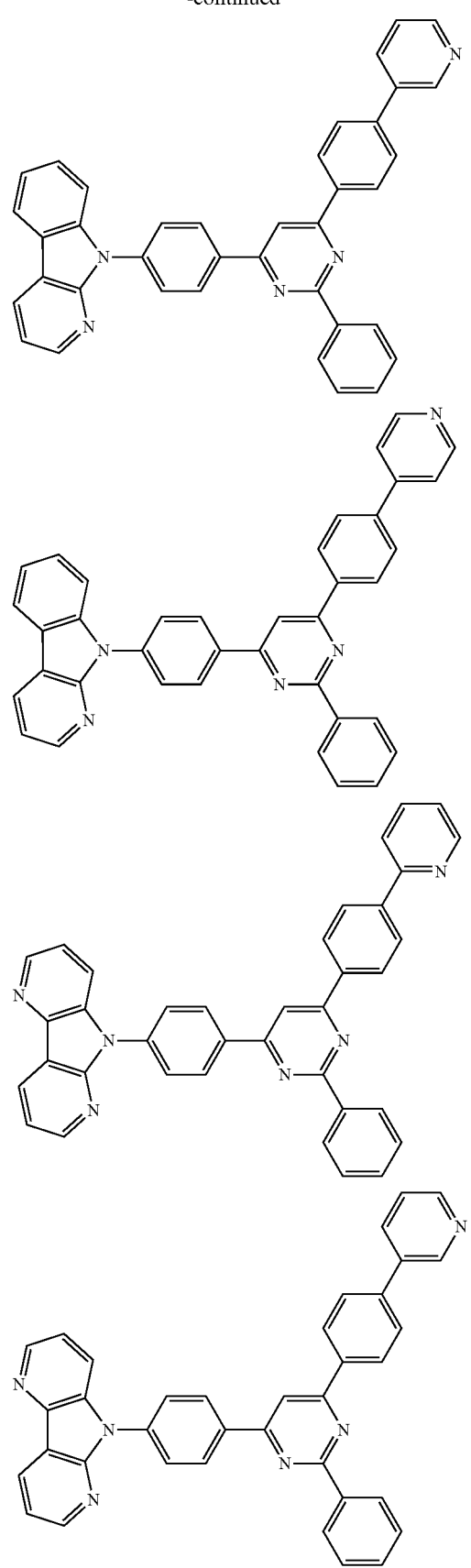

[Formula 30]
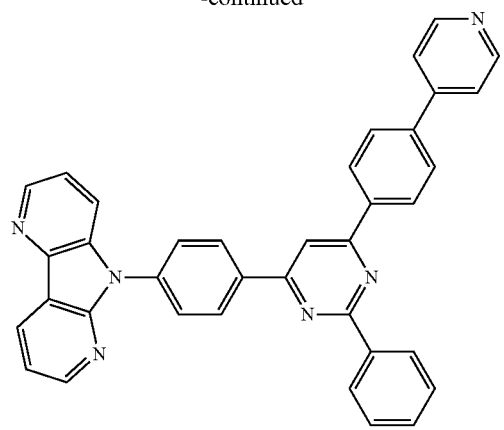
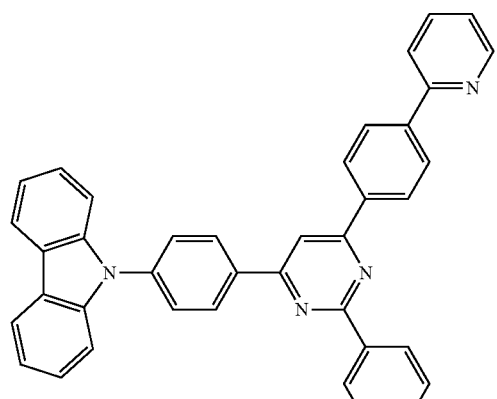
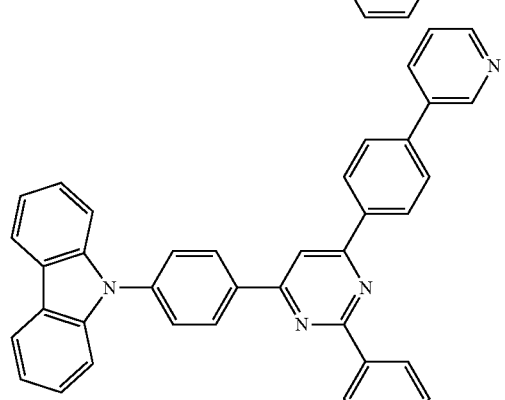
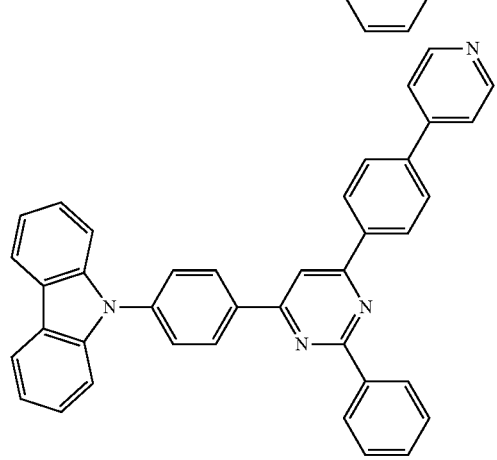
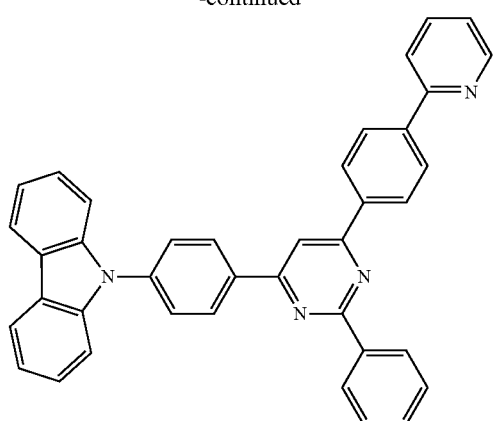
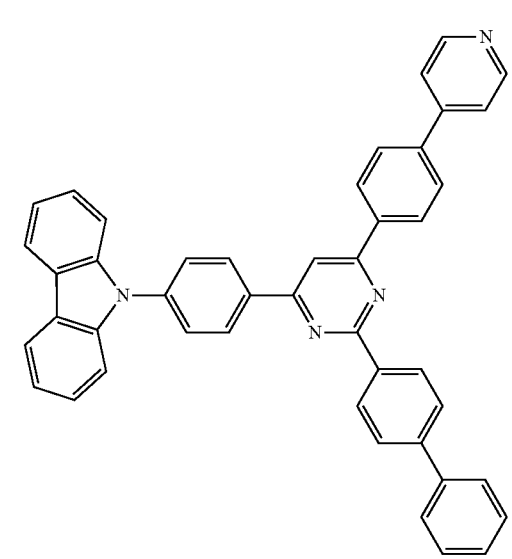
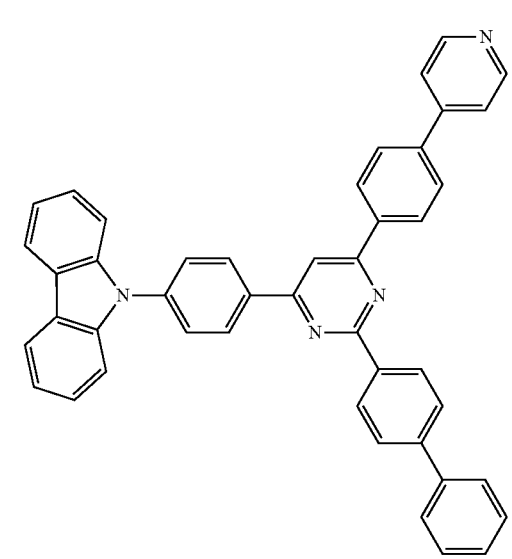
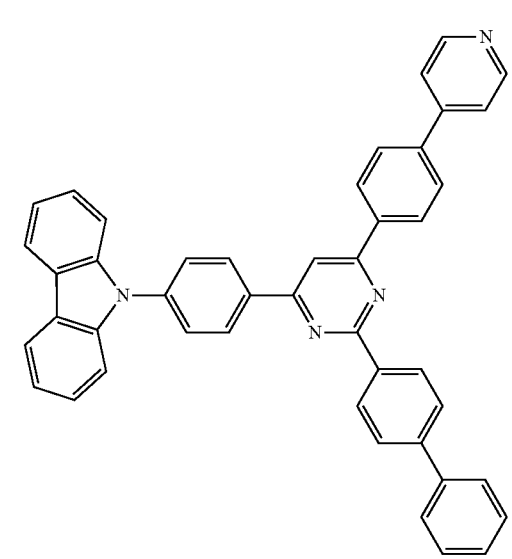

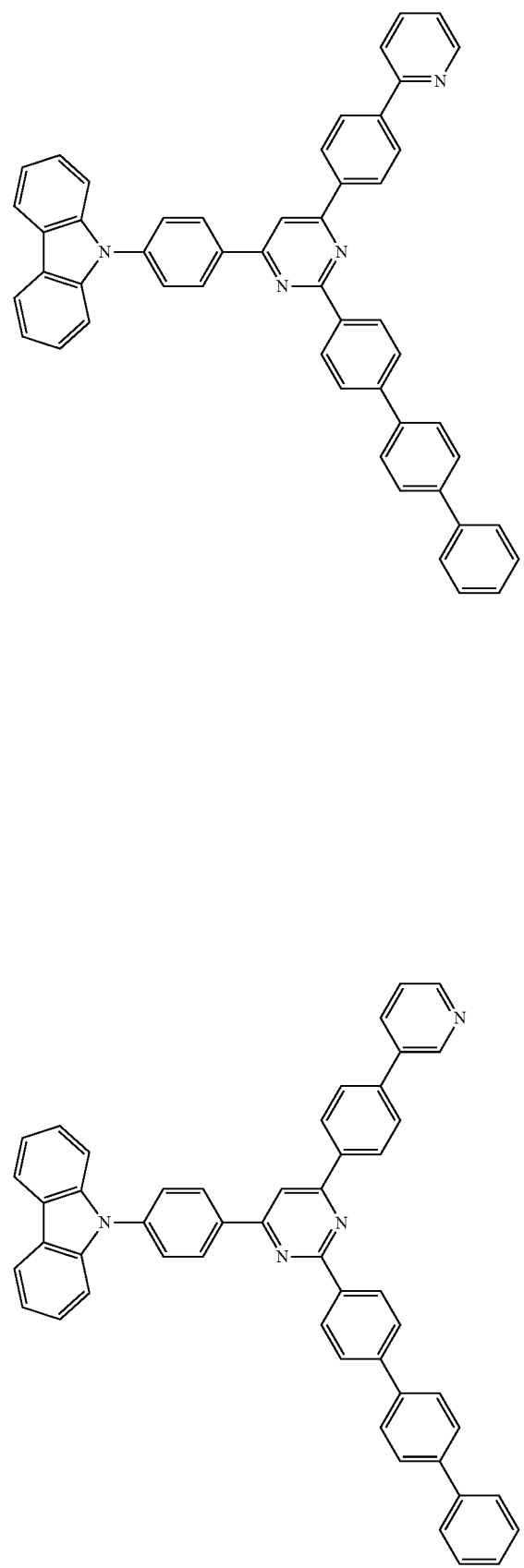
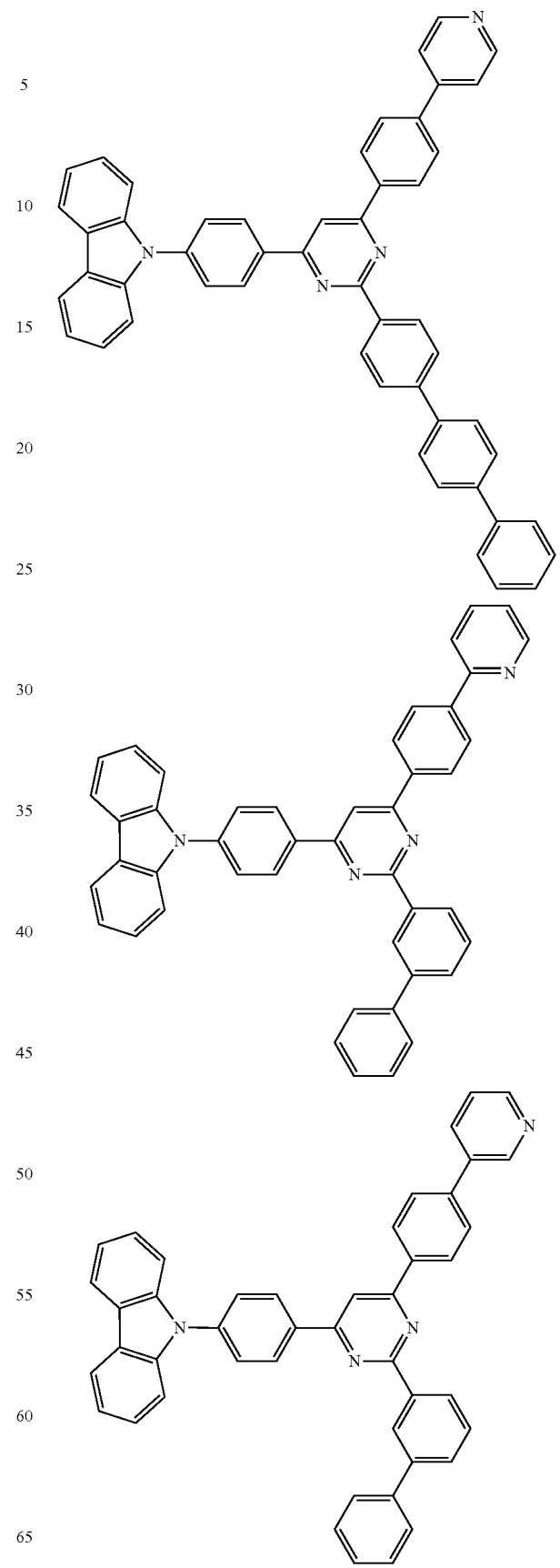

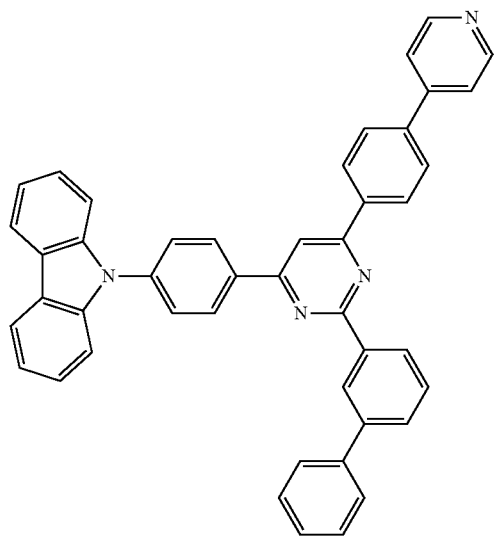
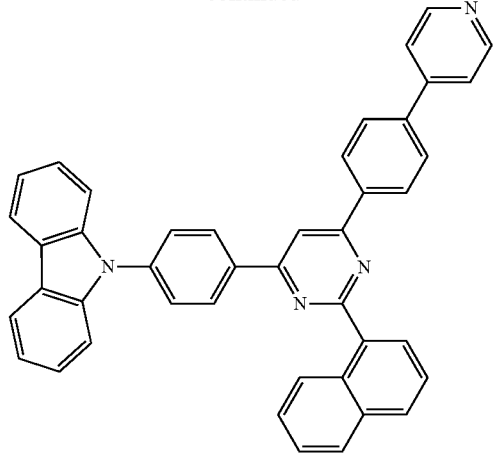
[Formula 31]
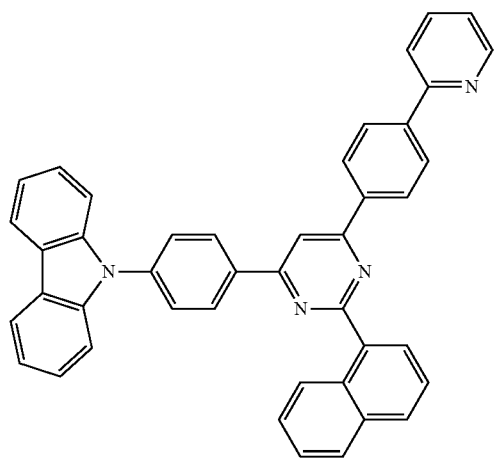
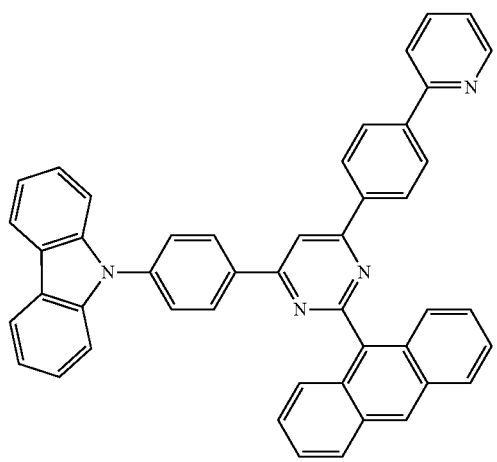
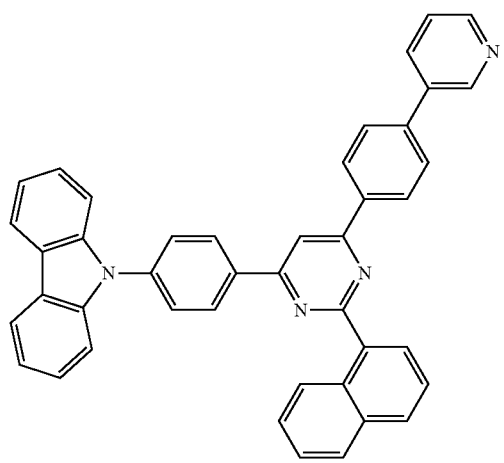
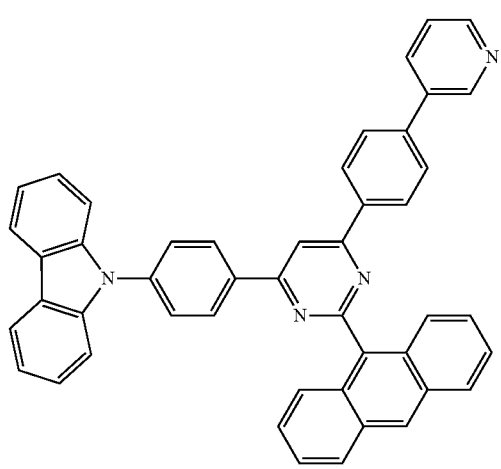

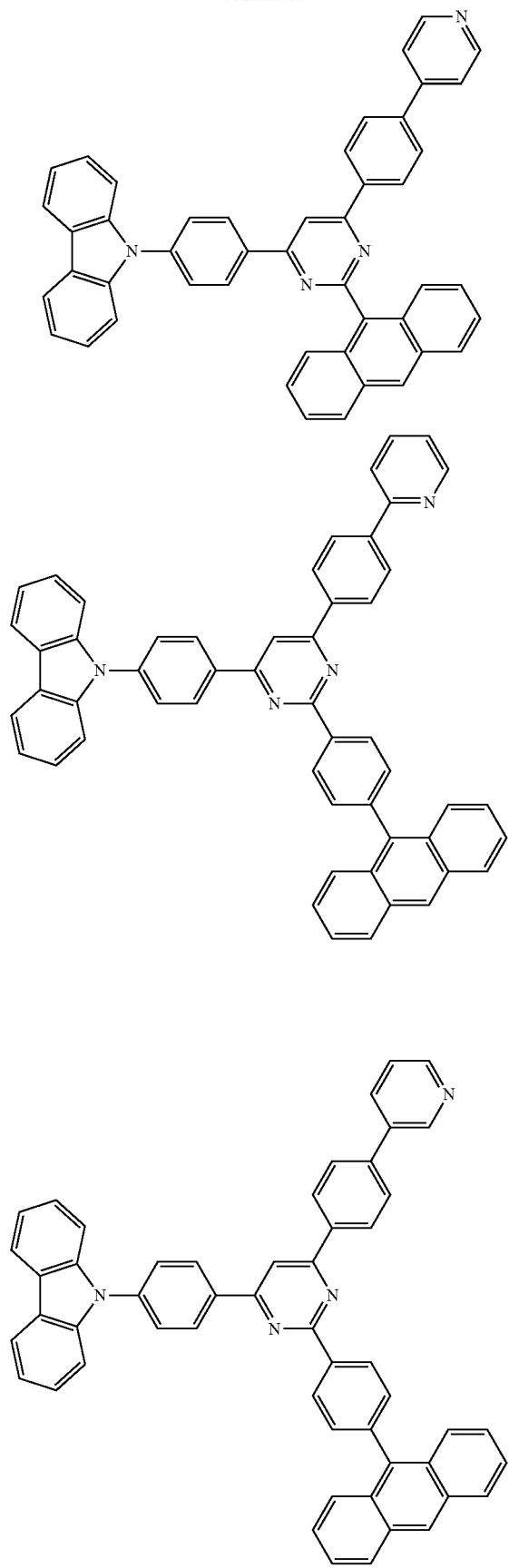
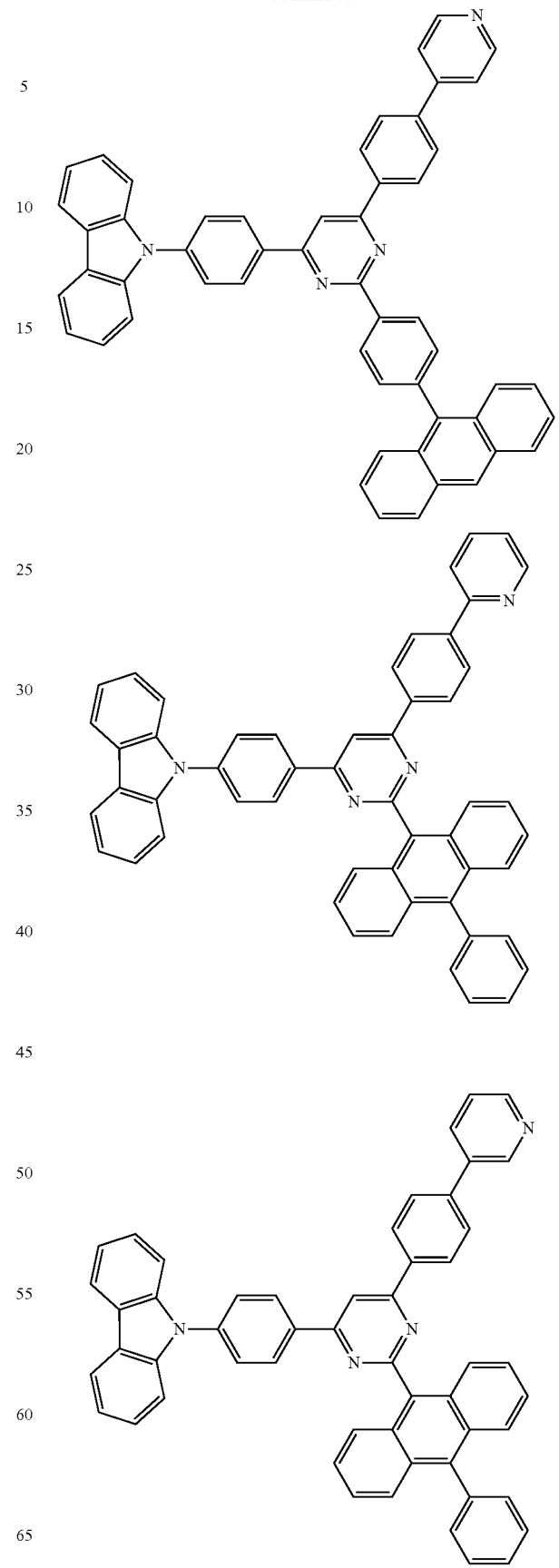

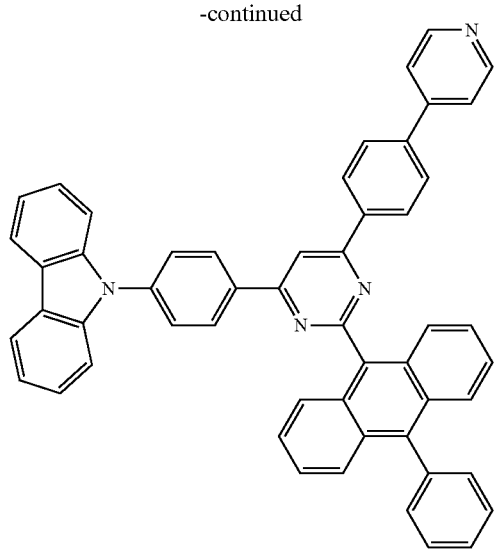
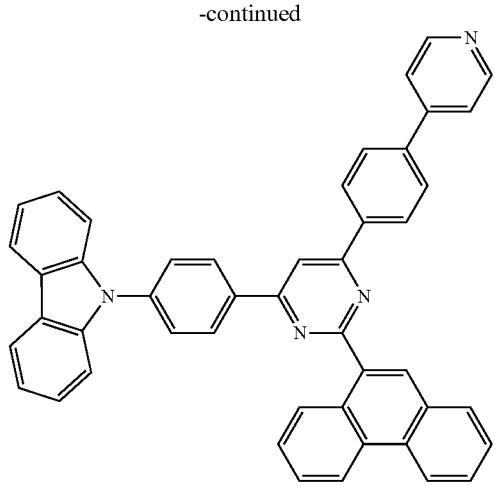
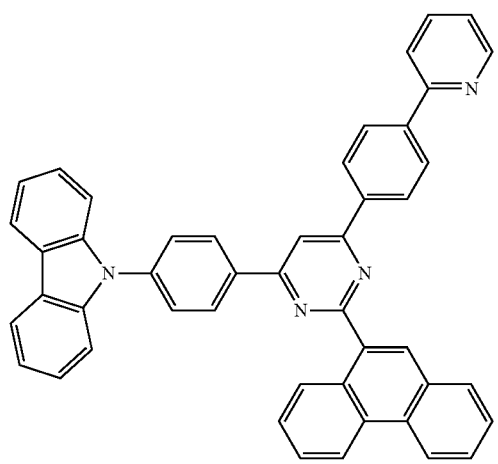
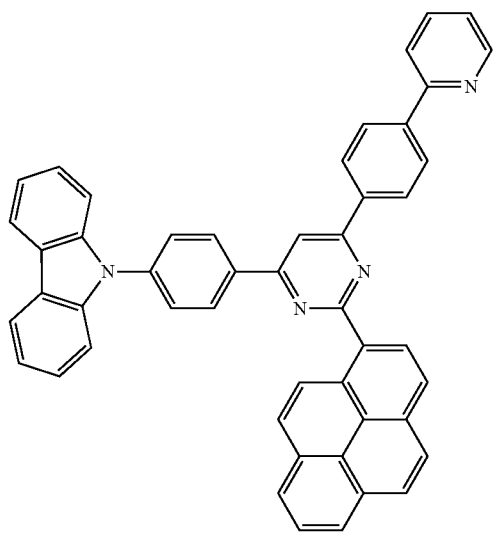
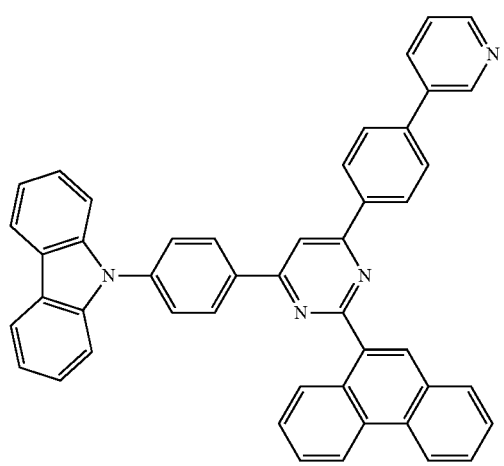
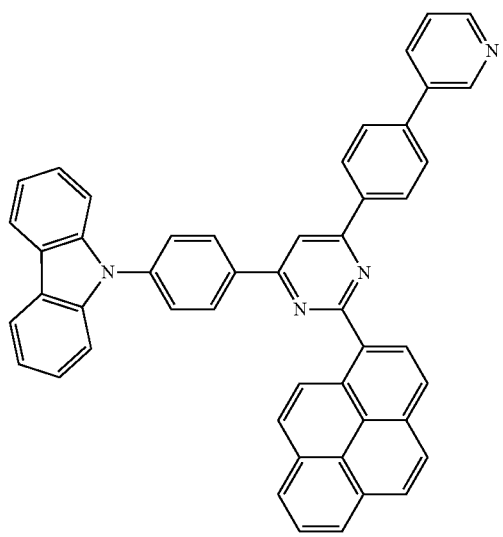

[Formula 32]
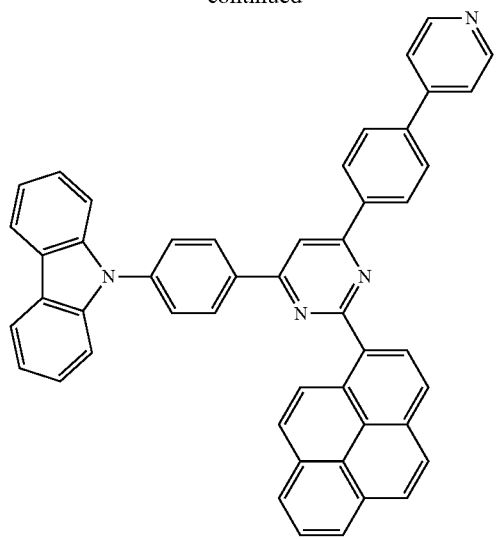
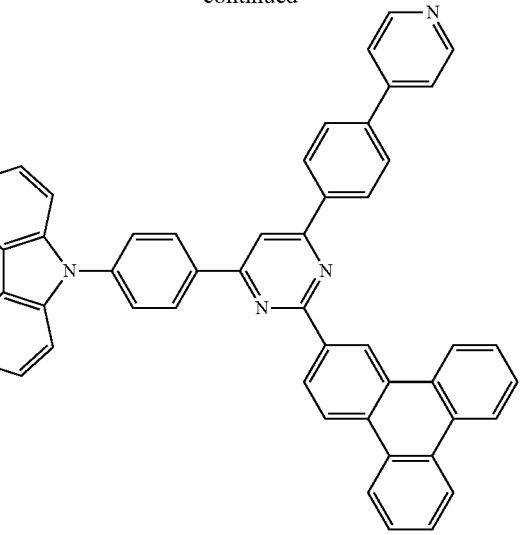
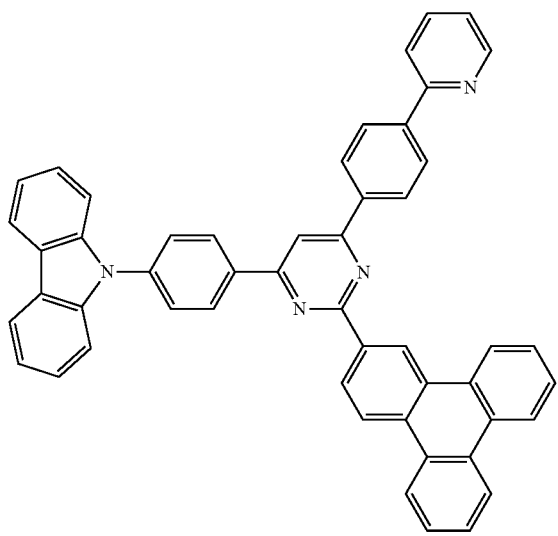
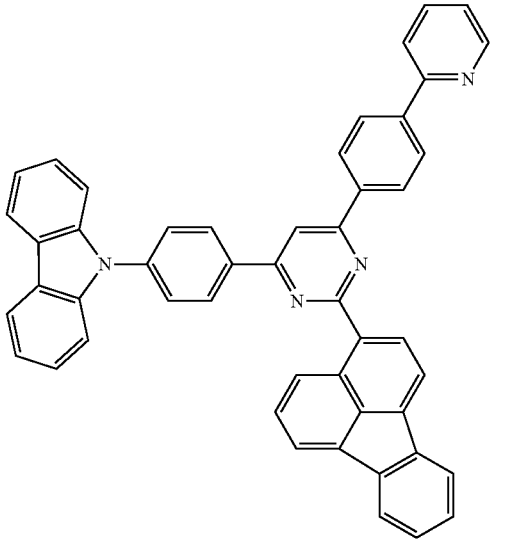
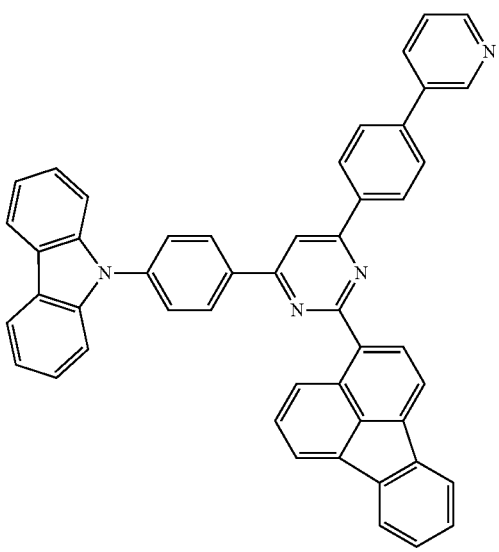

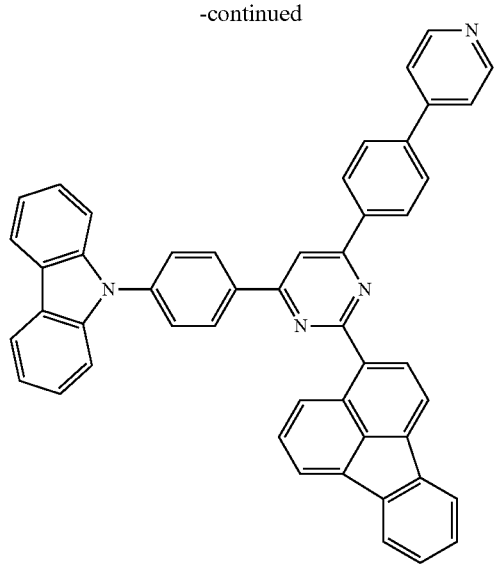
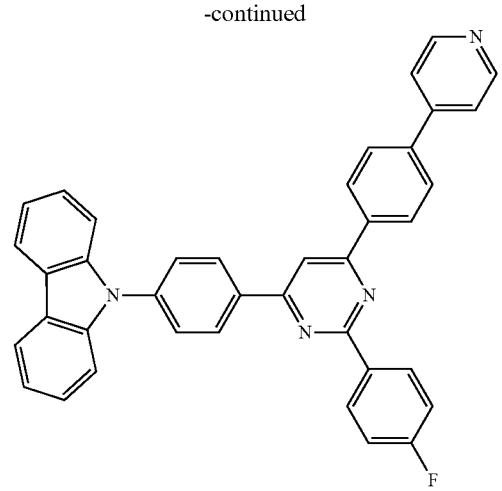
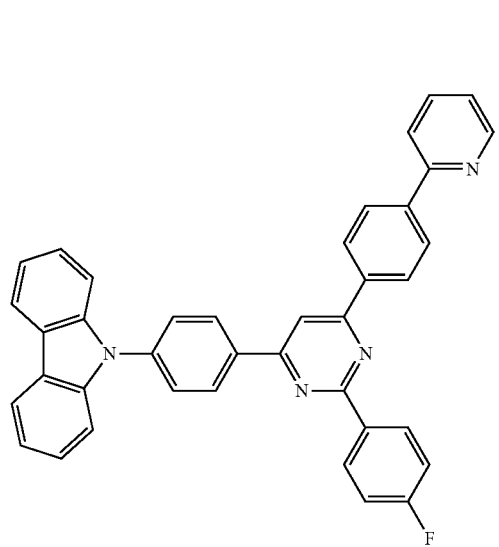
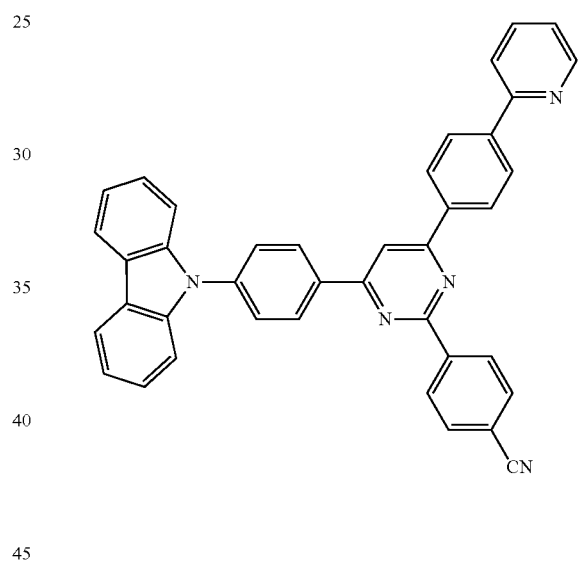
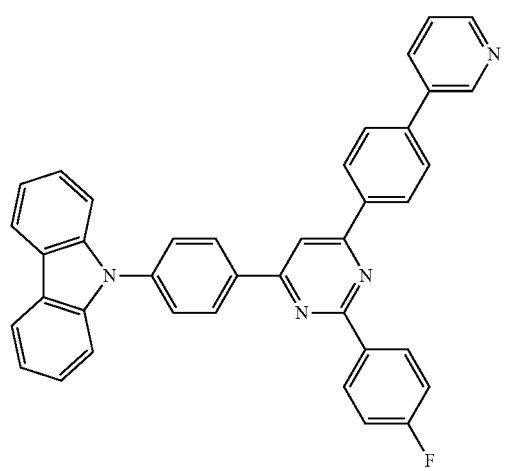
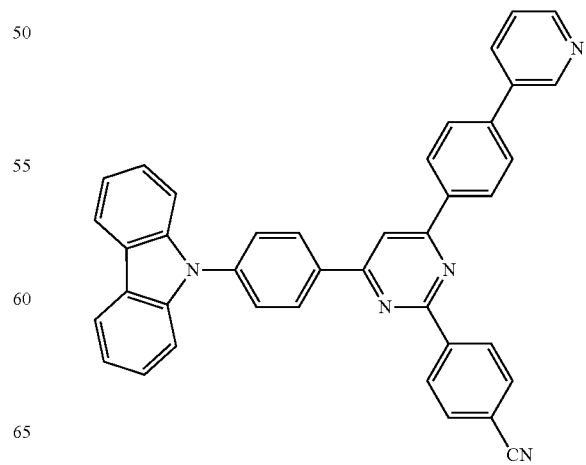

[Formula 33]
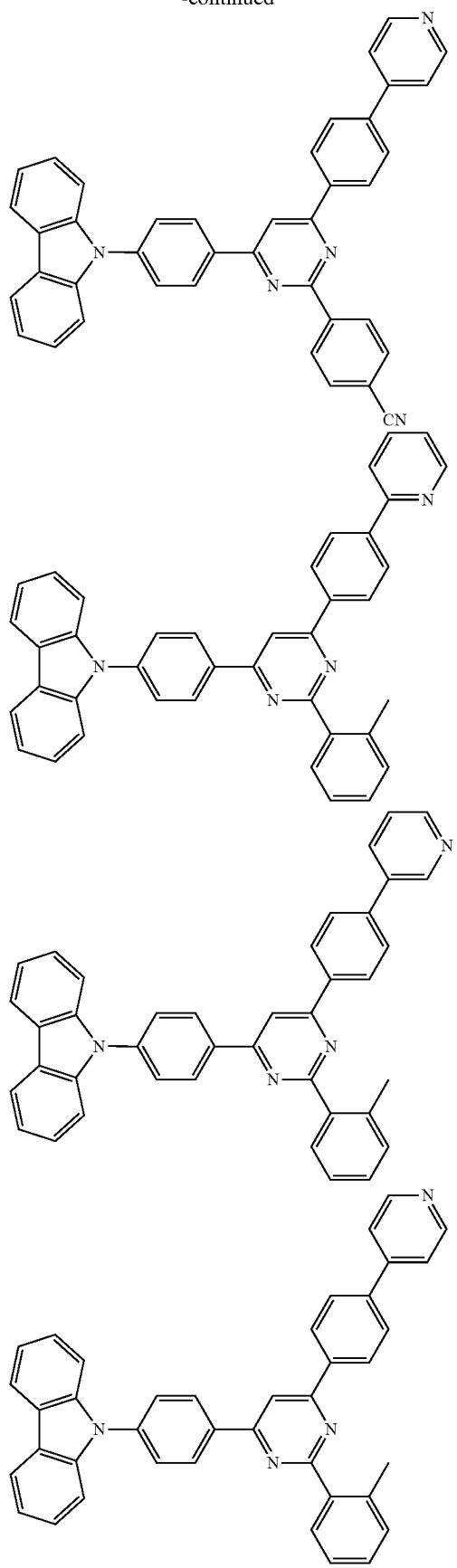
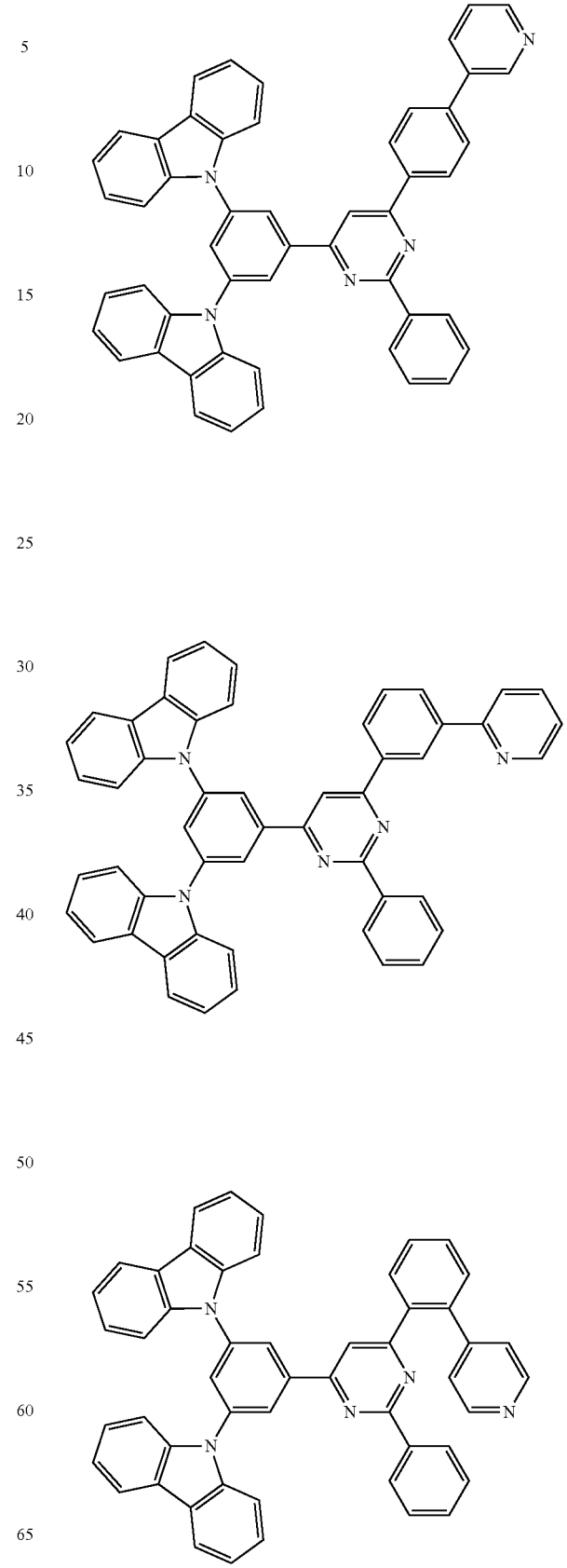

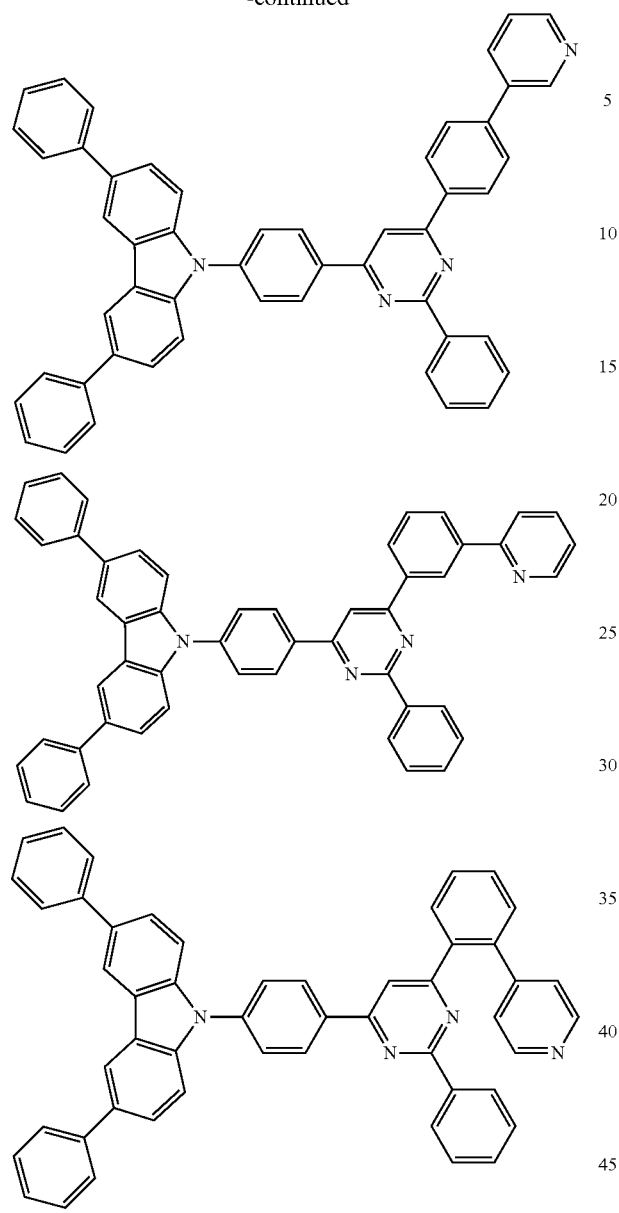
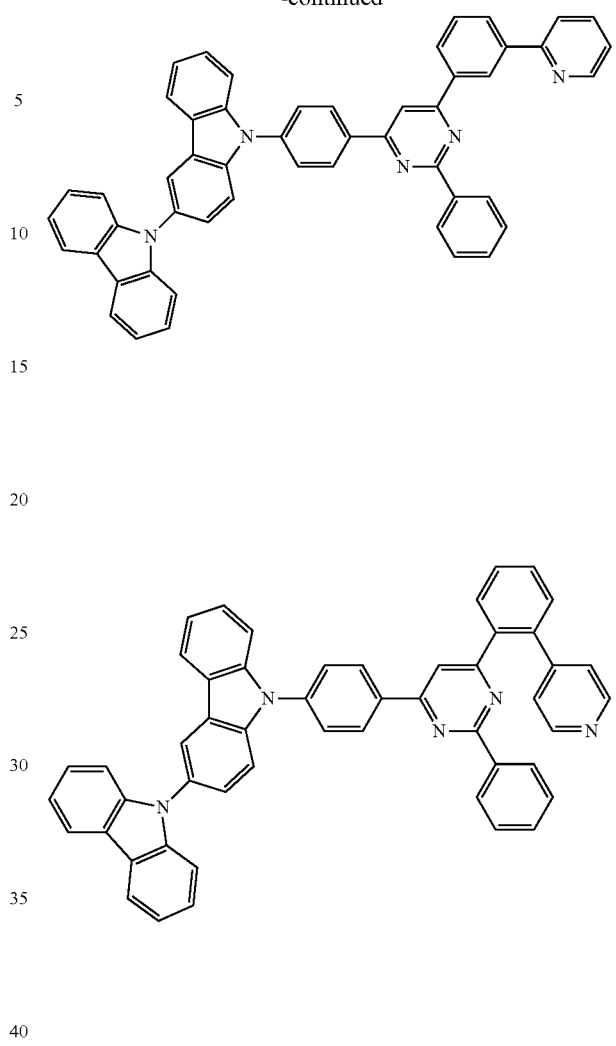
[Formula 34]
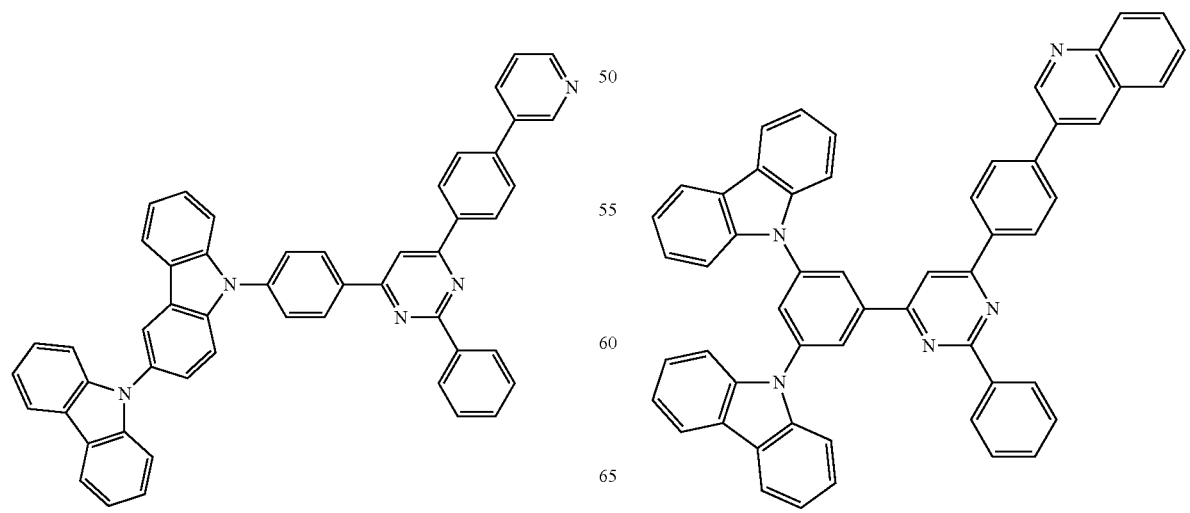

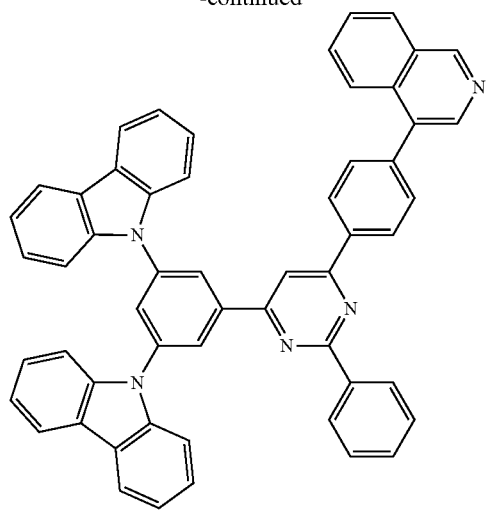
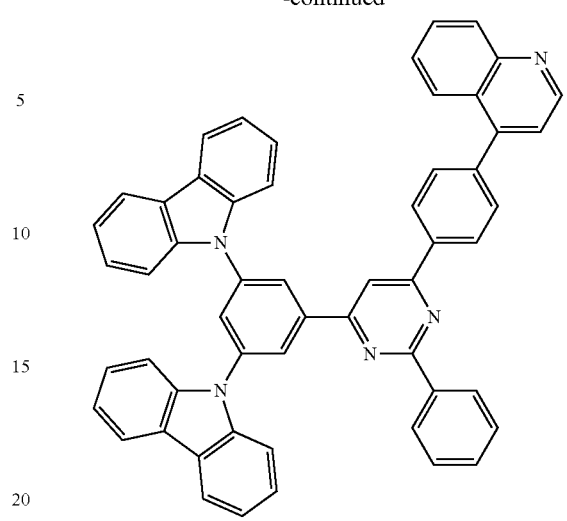
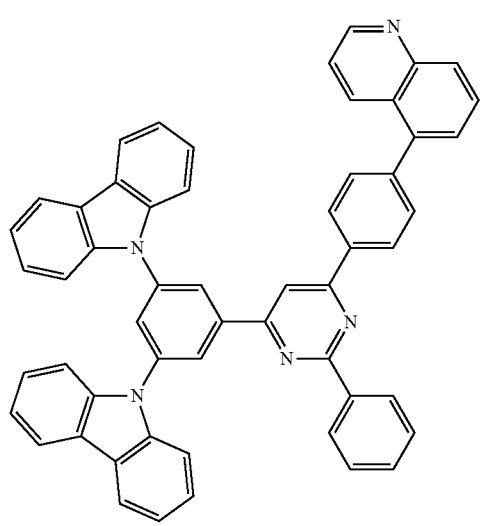
[Formula 35]
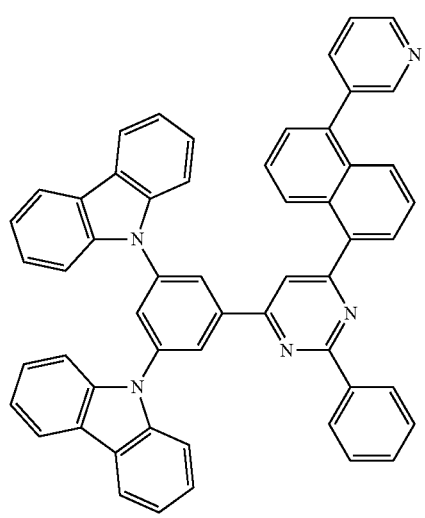

-continued
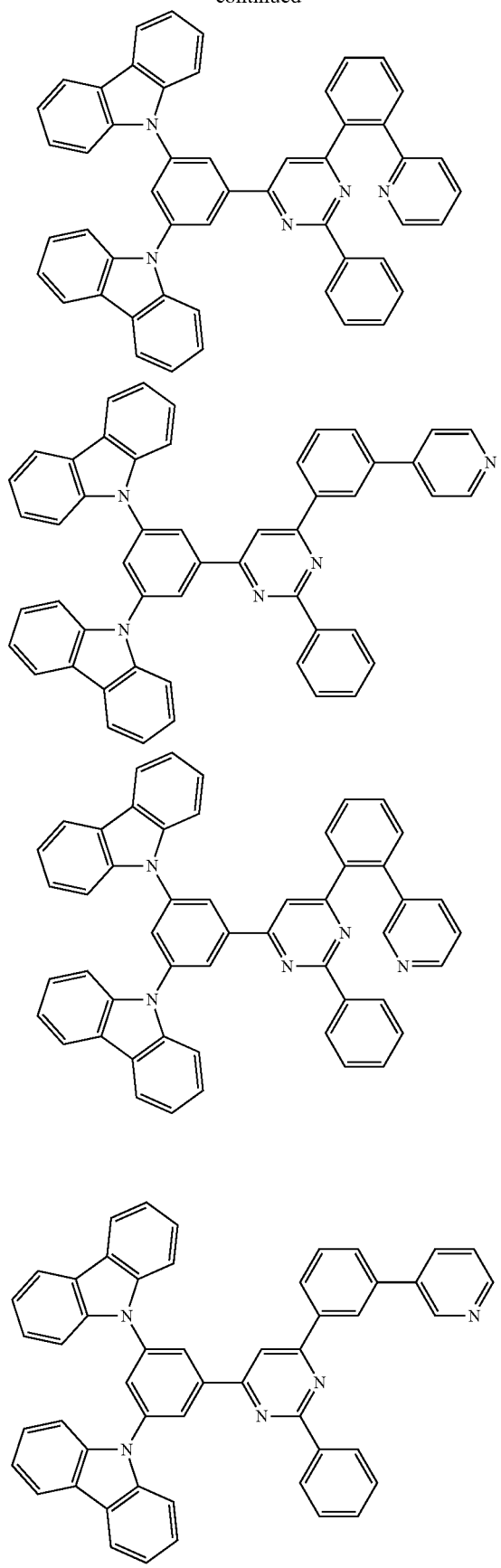
-continued
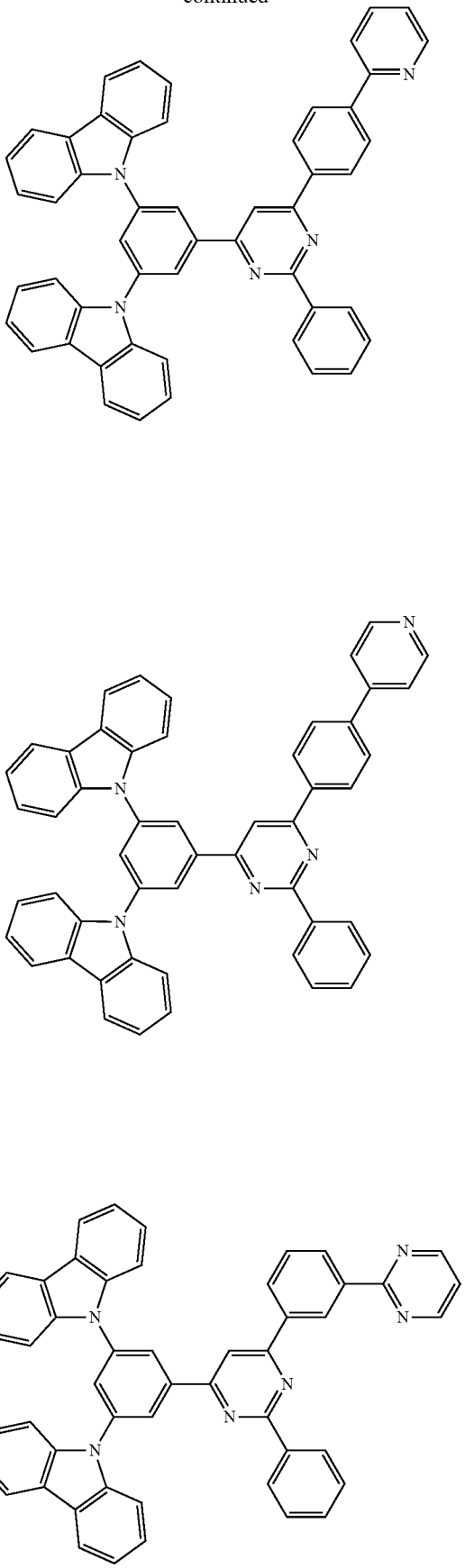

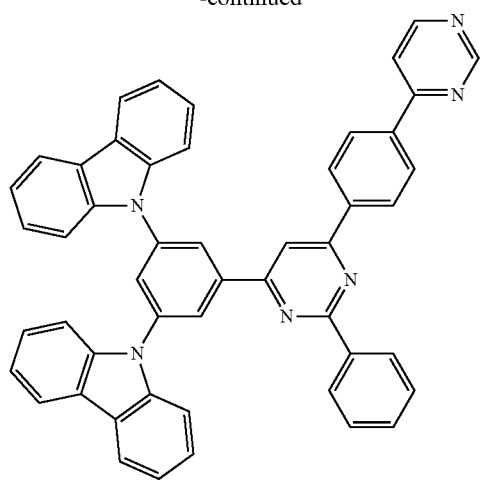
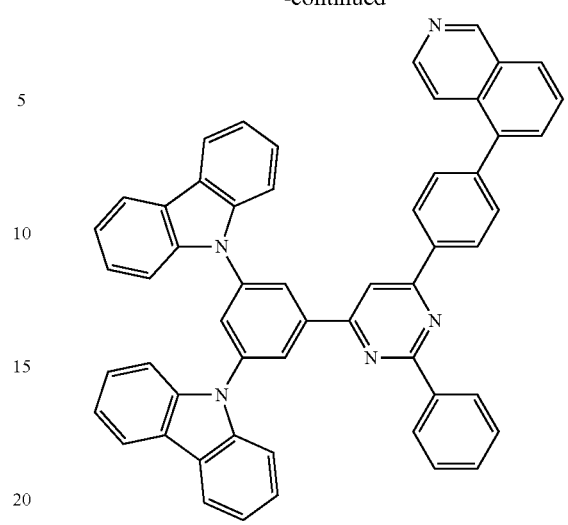
[Formula 36]
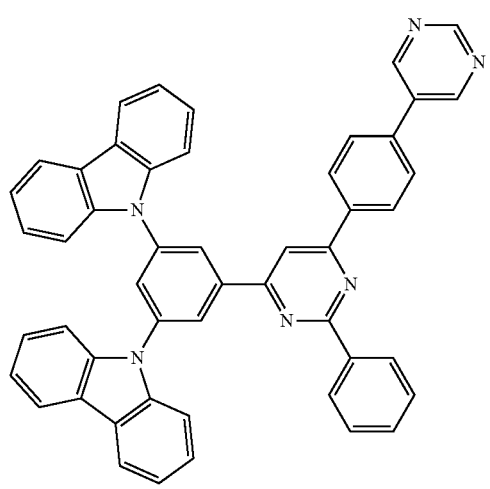
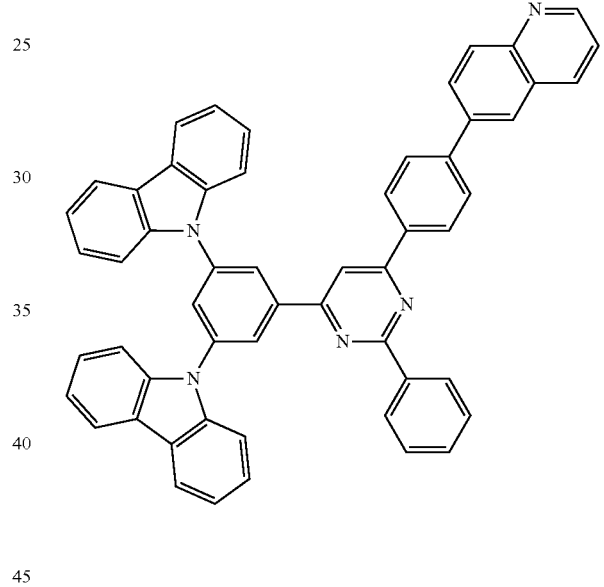
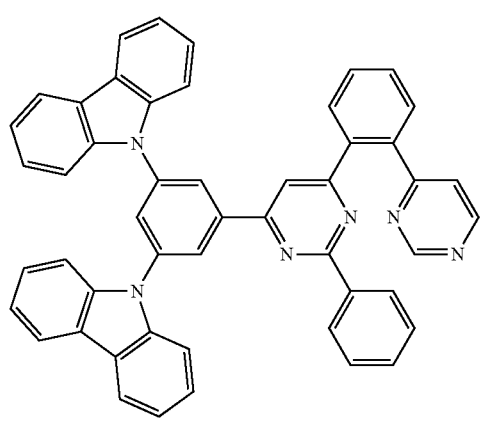
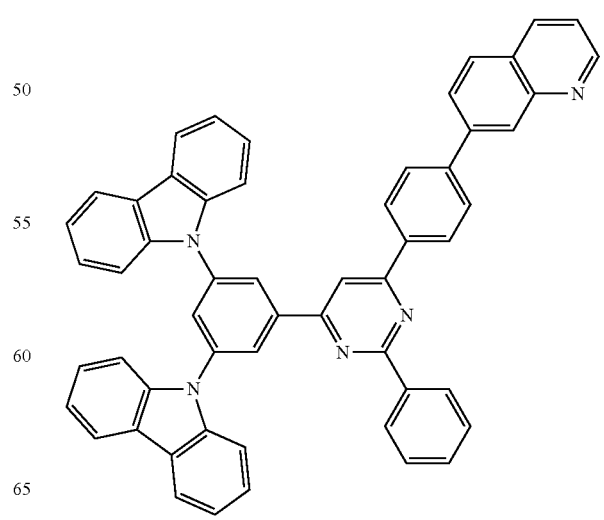

69
-continued
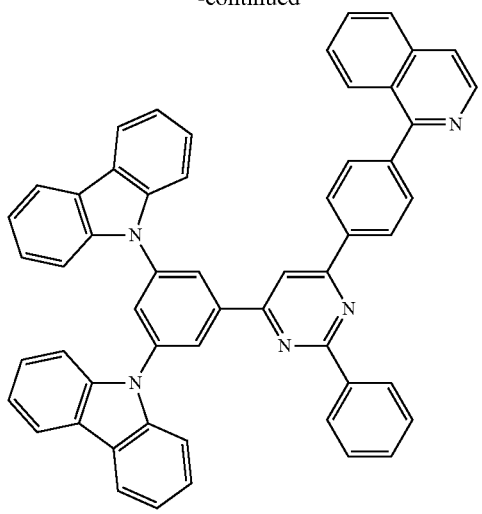
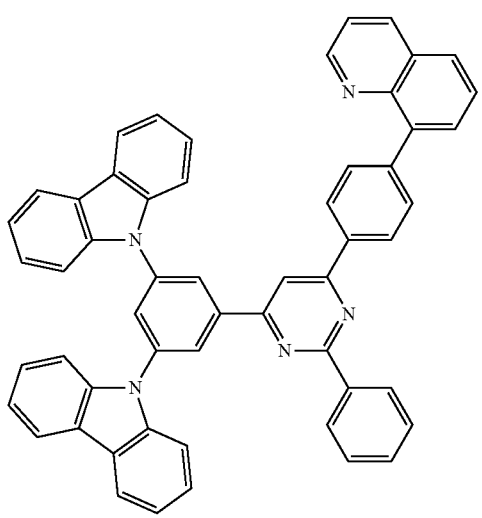
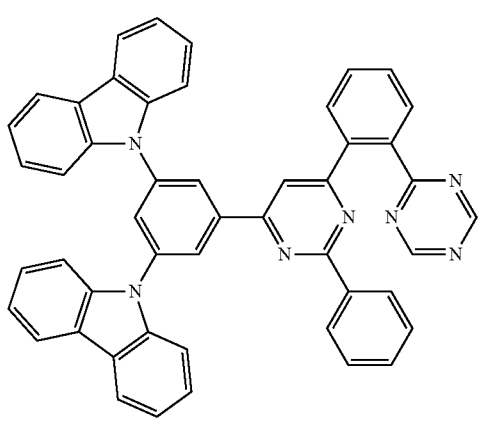
70
-continued
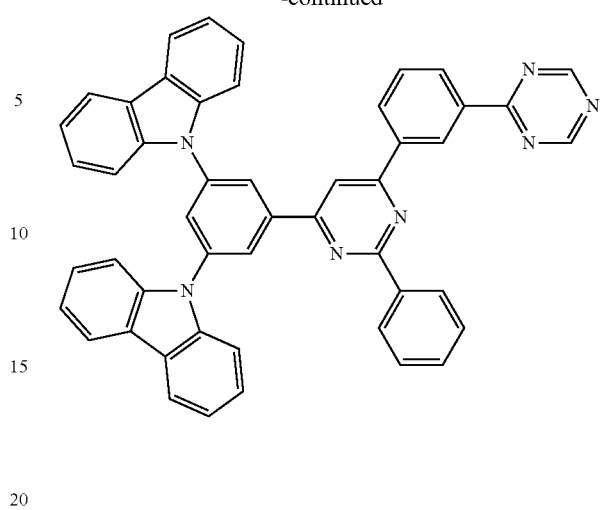
[Formula 37]
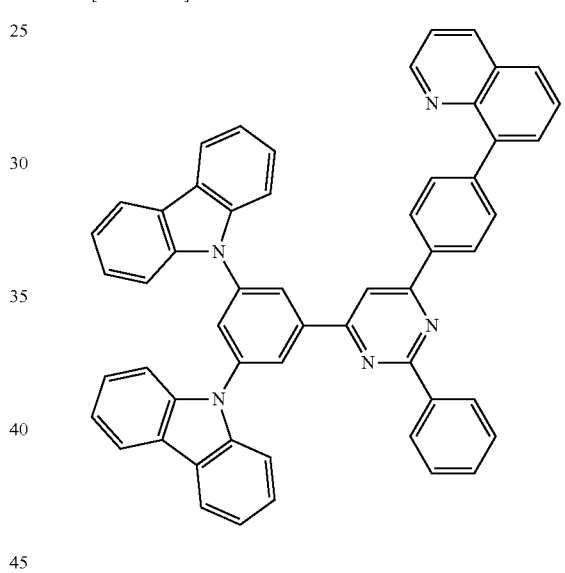
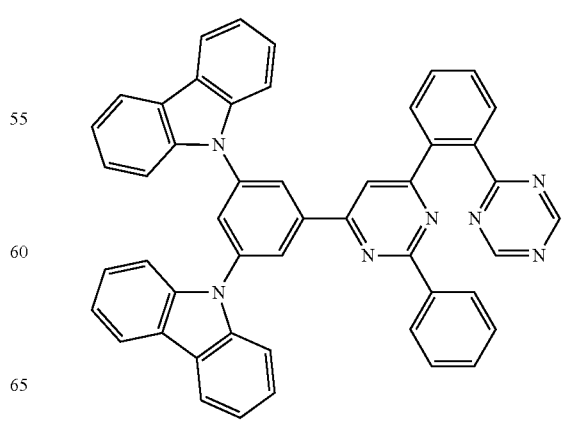

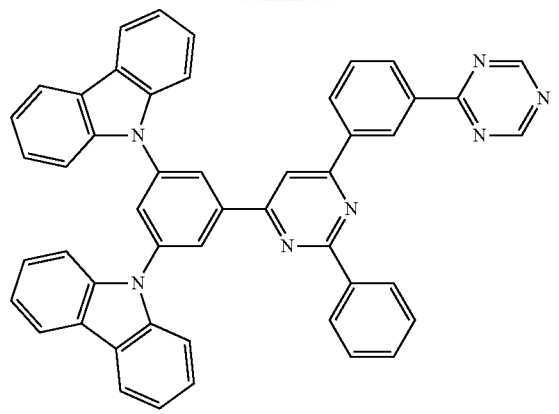
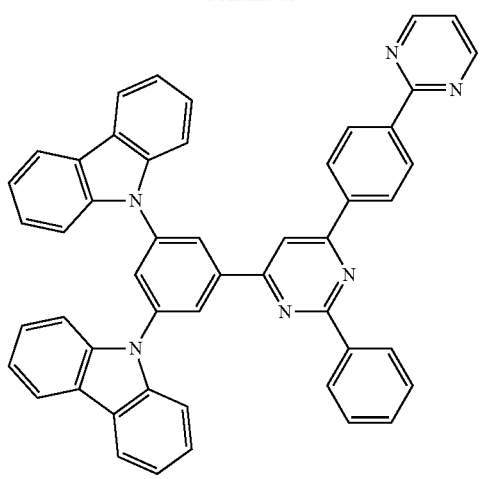
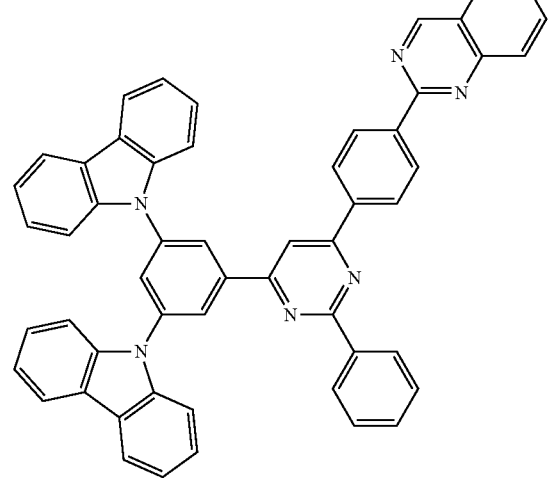
[Formula 38]
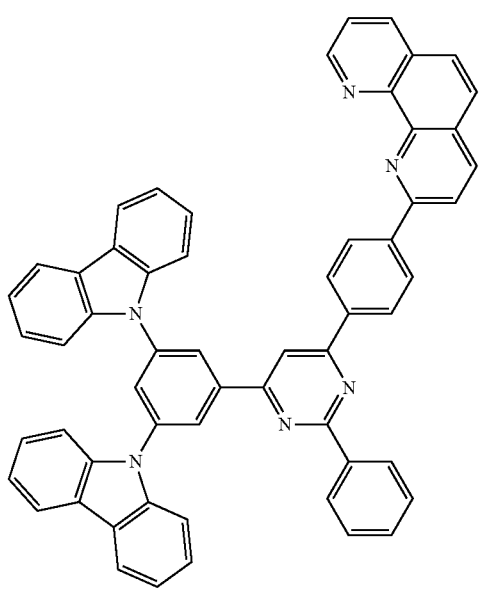
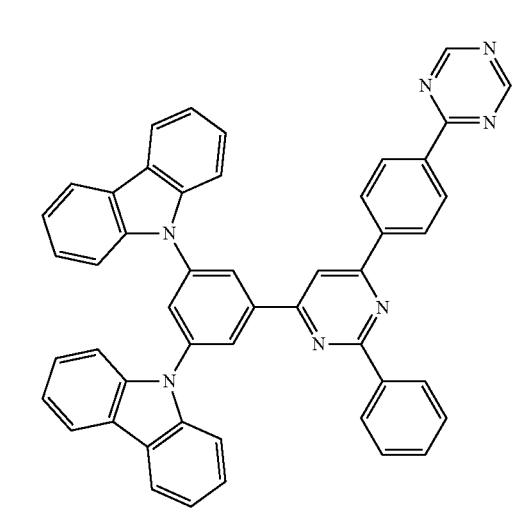
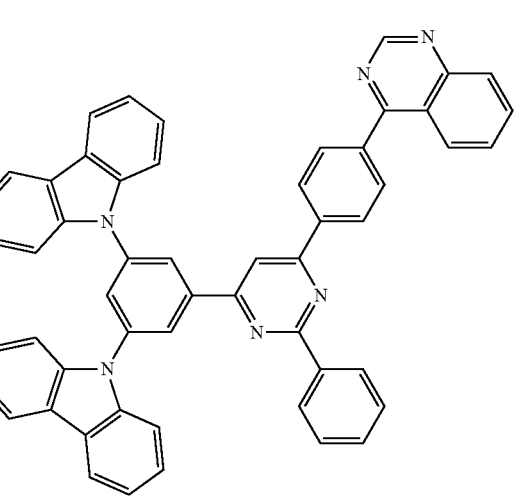

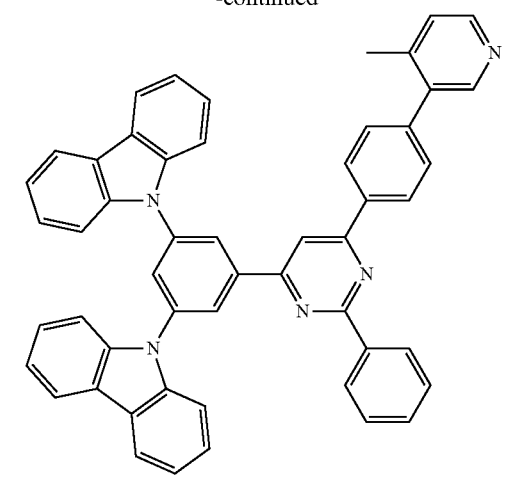
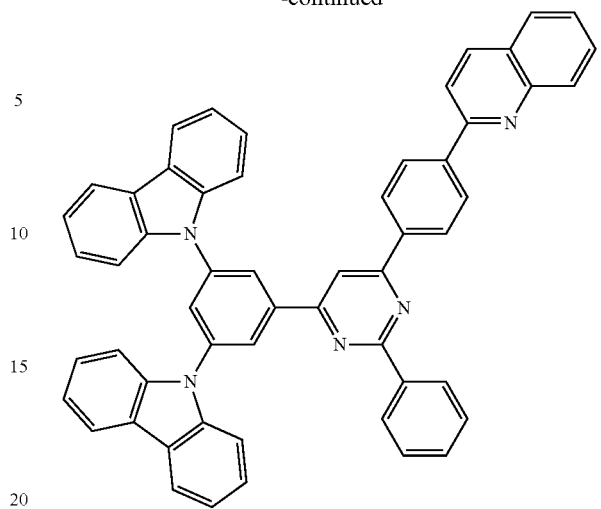
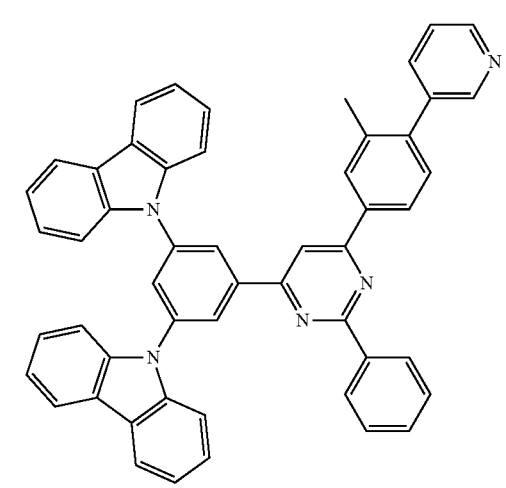
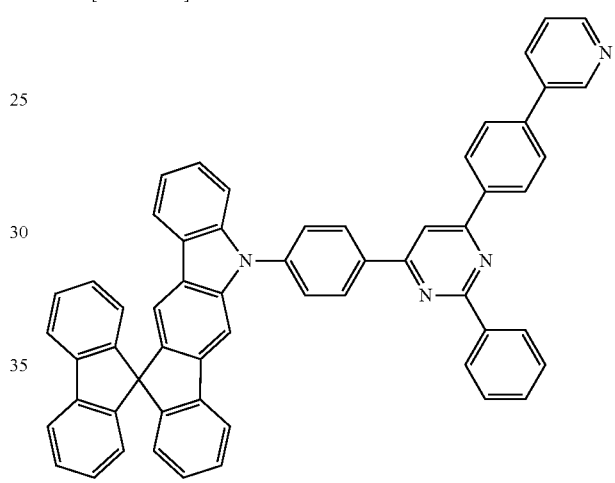
[Formula 39]
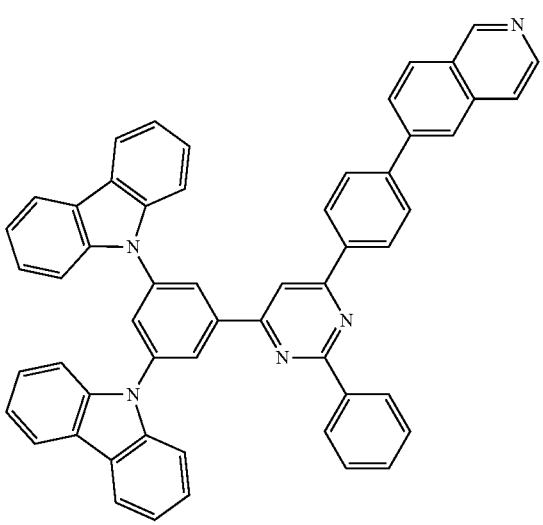
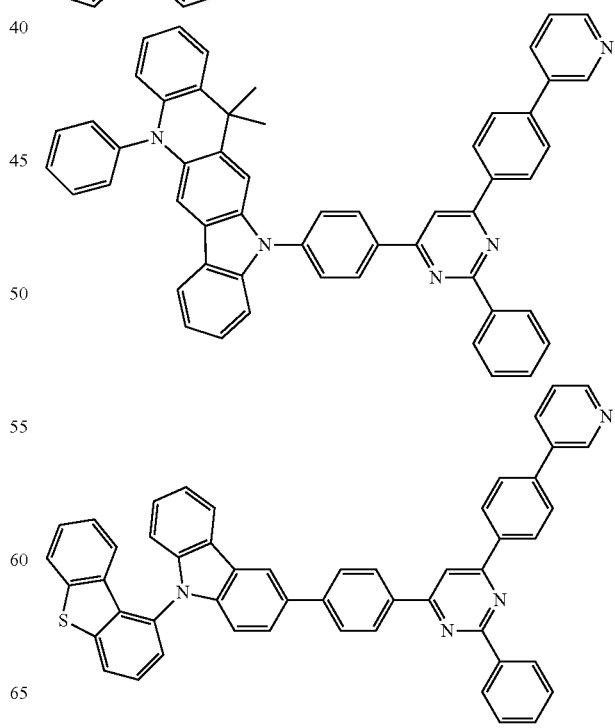

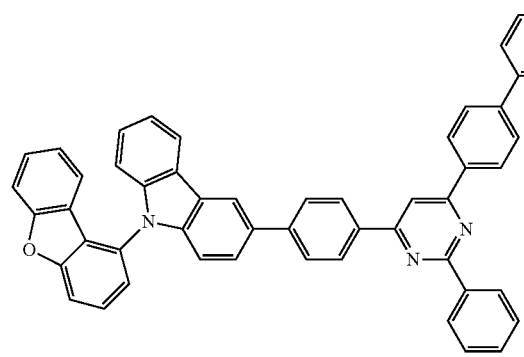
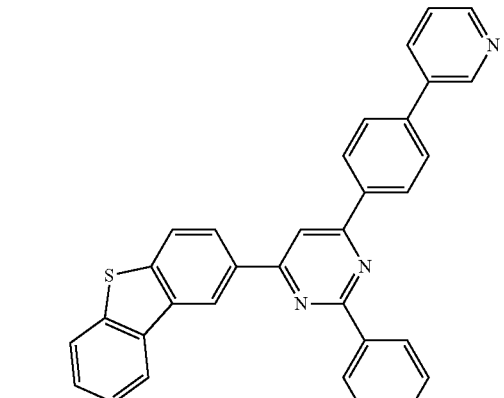
[Formula 40]
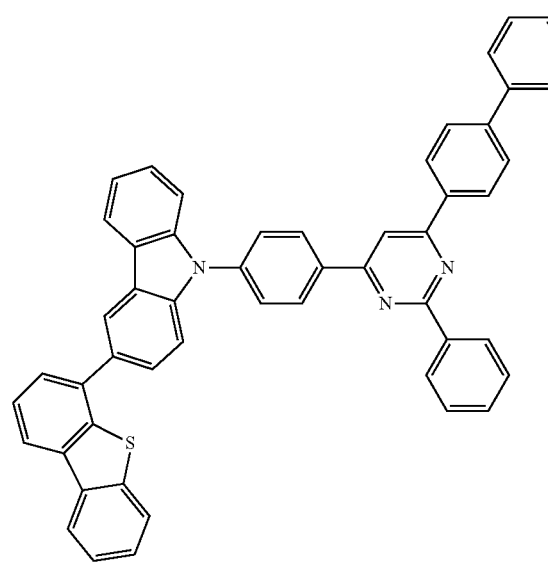
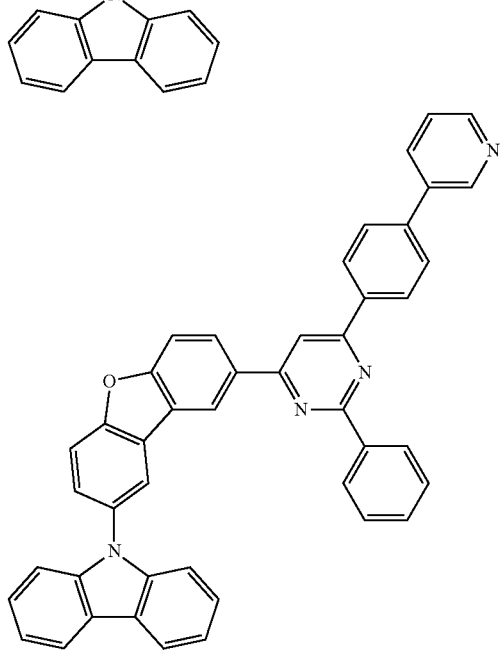
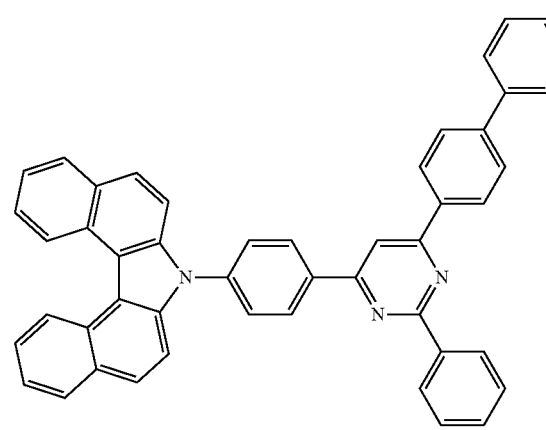
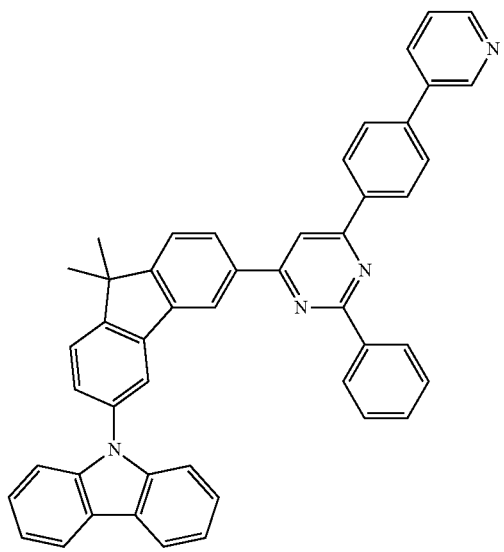

[Formula 41]
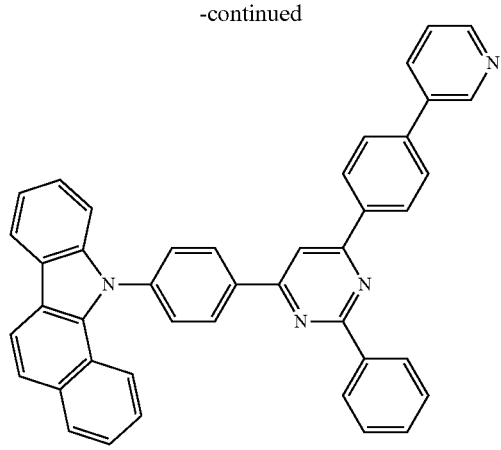
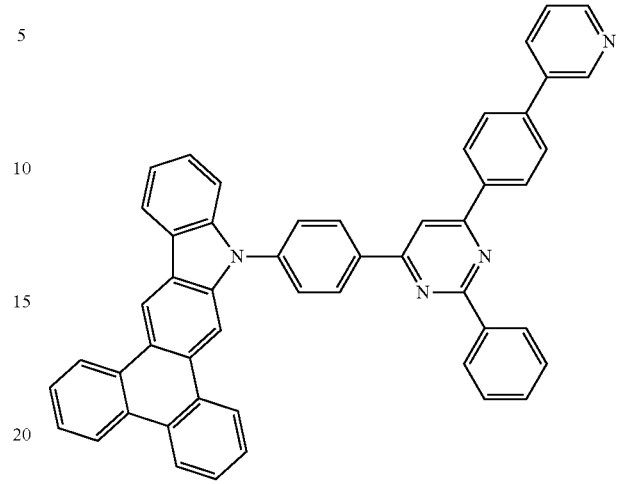
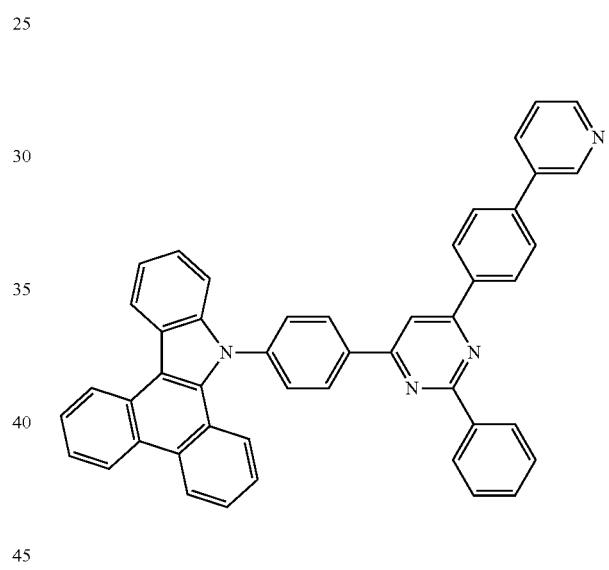
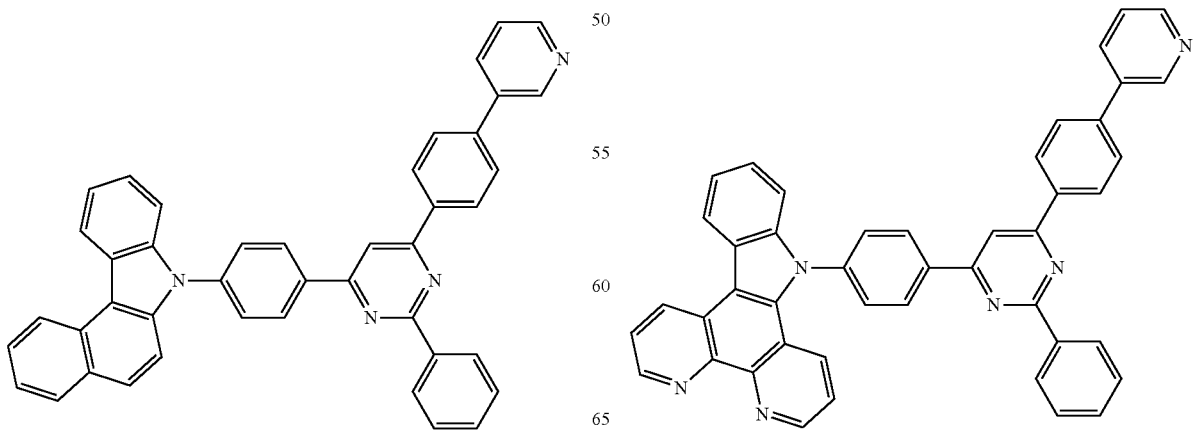

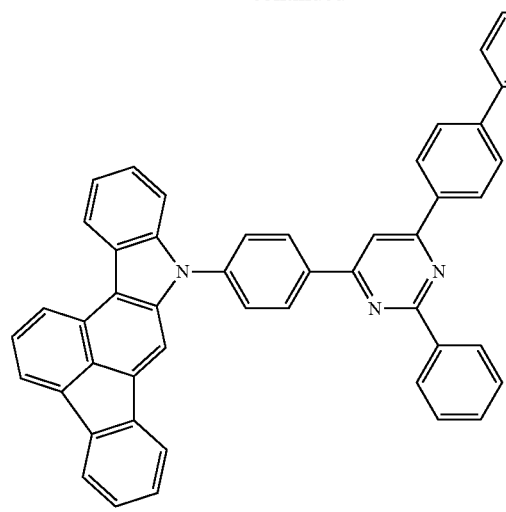
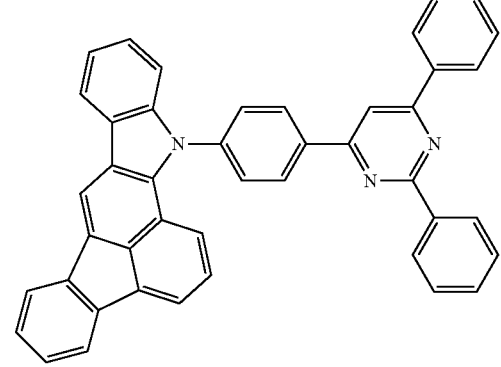
[Formula 42]
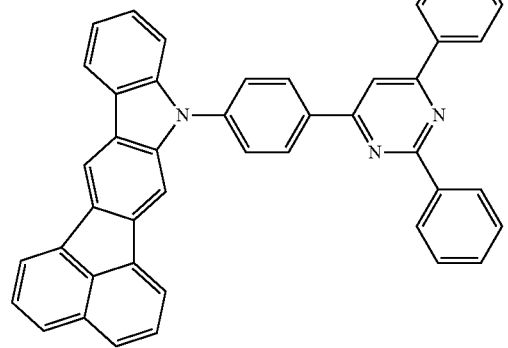
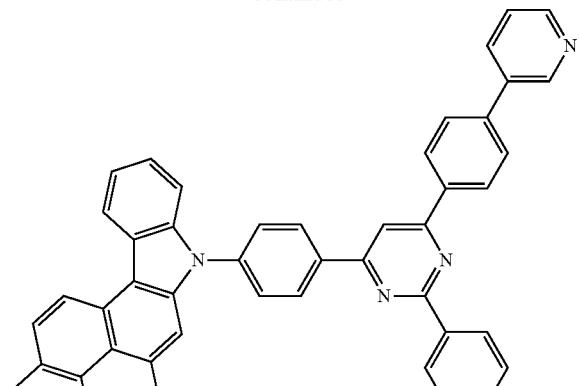
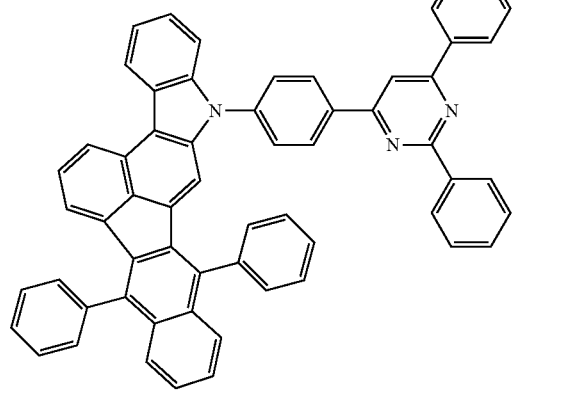
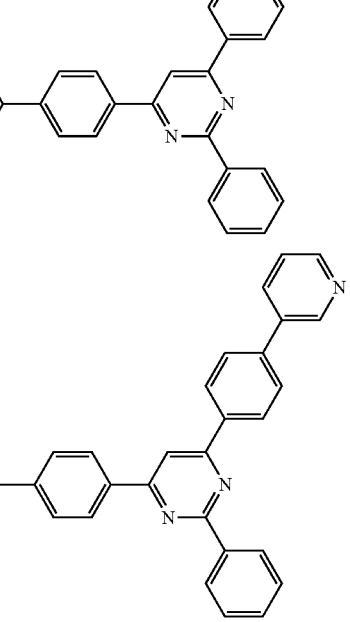

81
-continued
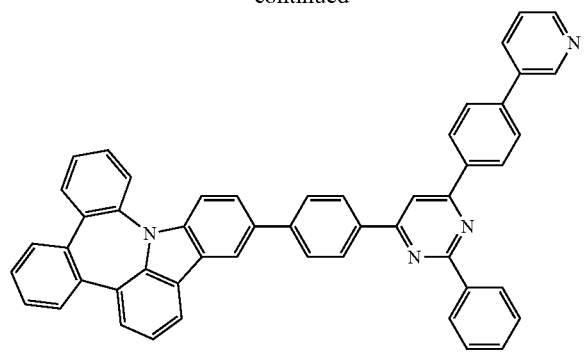
[Formula 43]
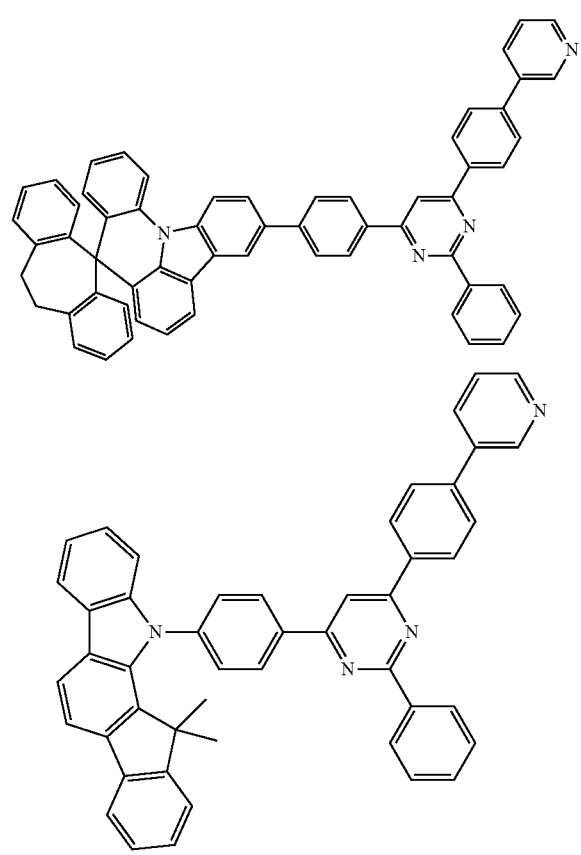
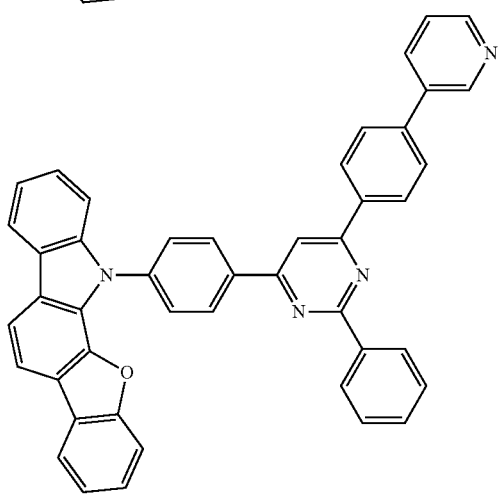
82
-continued
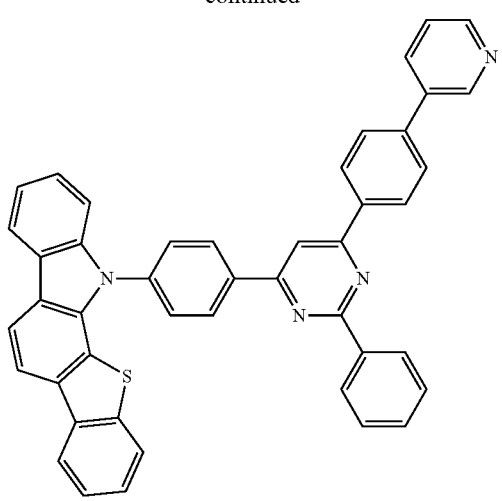
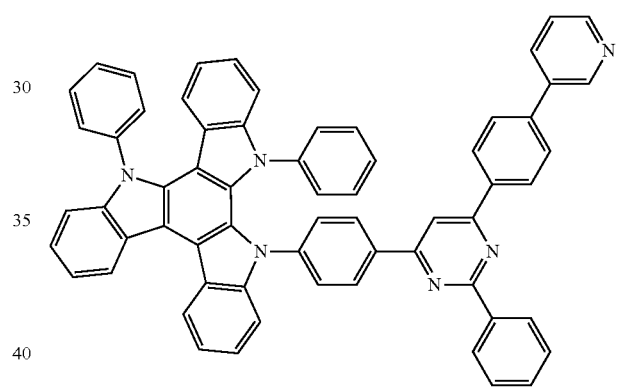
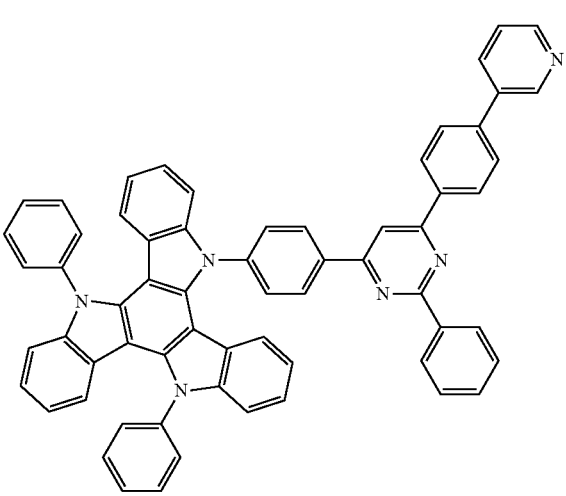

[Formula 44]
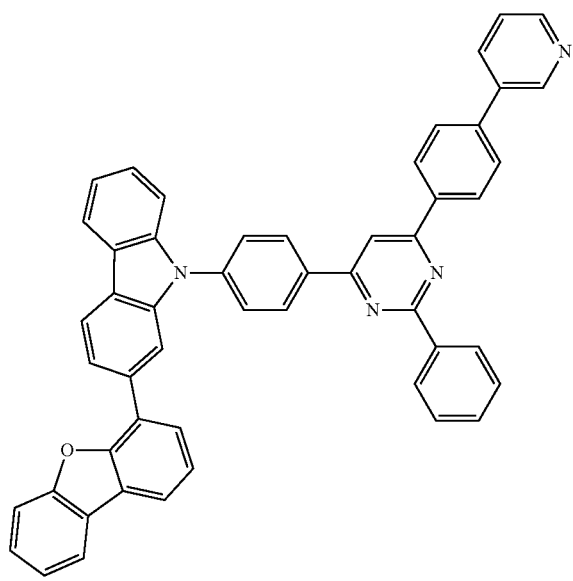
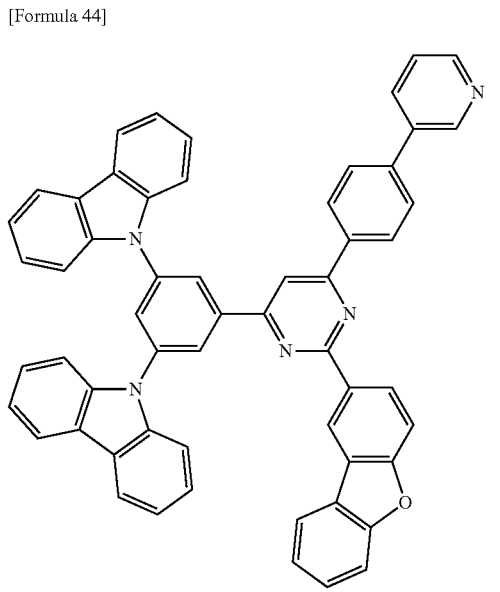
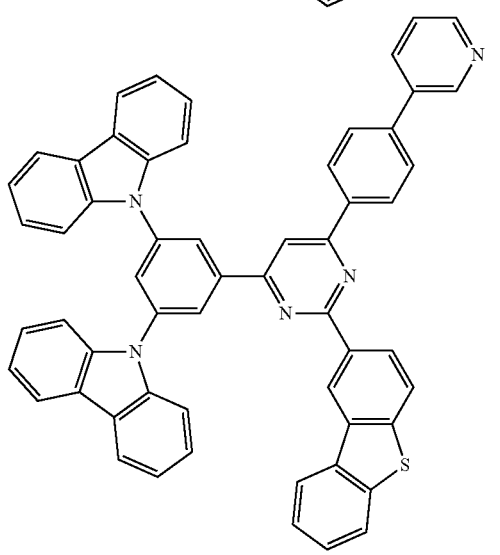
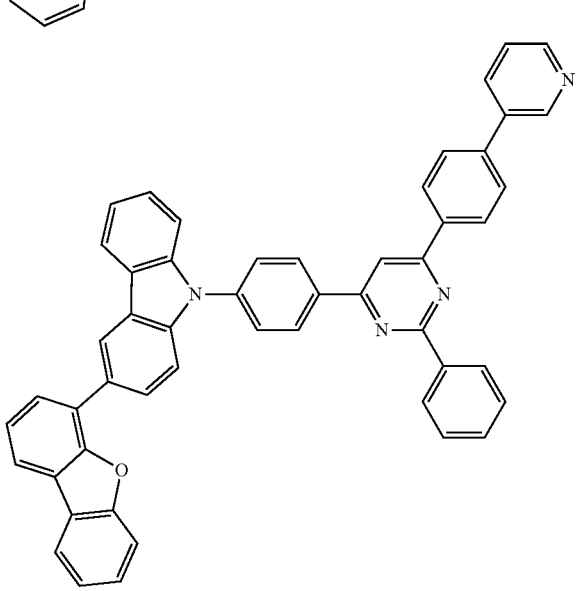
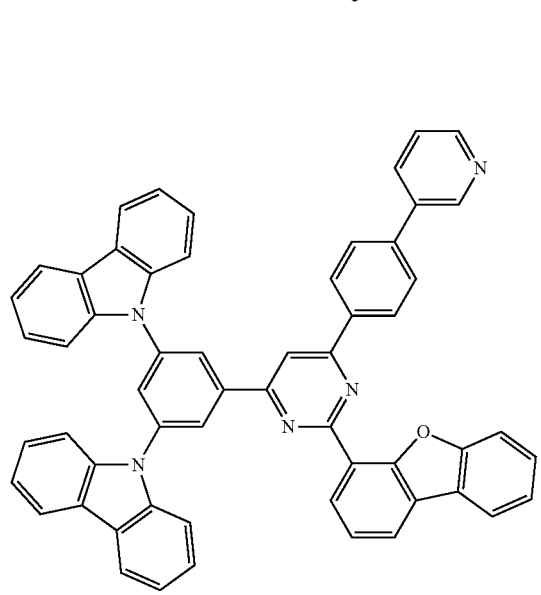

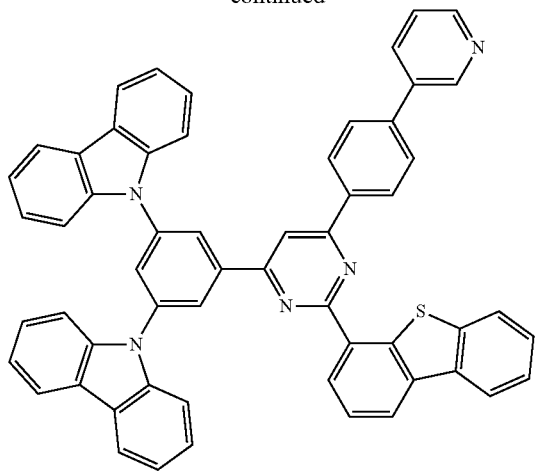

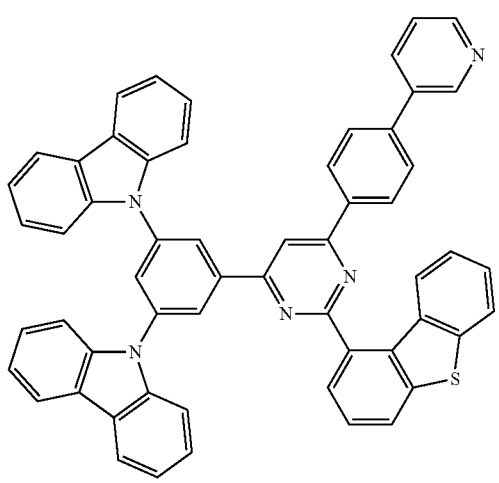

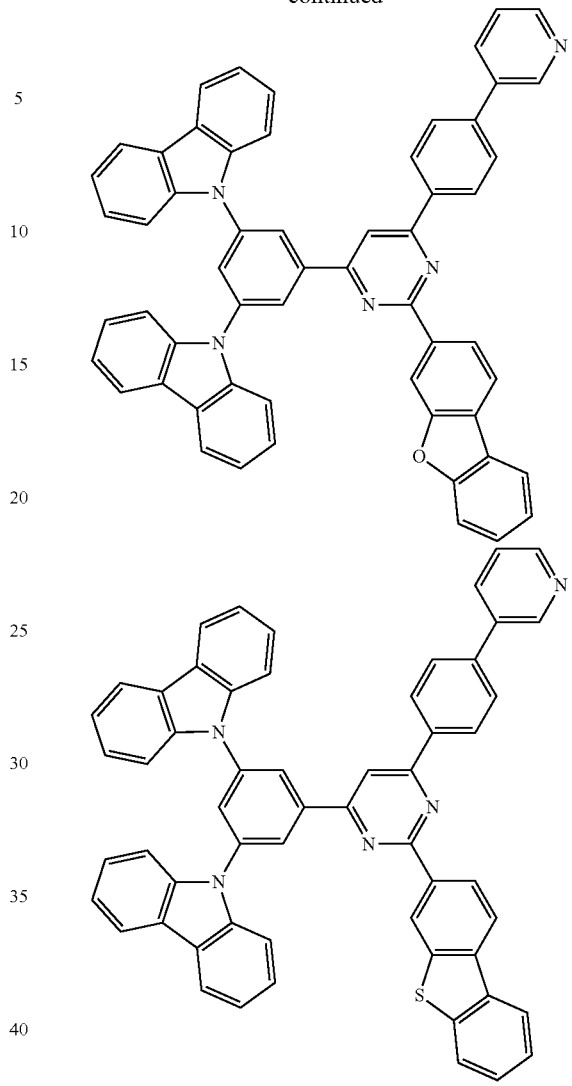

Organic-EL-Device Material

The compound according to the exemplary embodiment is usable as an organic-EL-device material. In this arrangement, the compound according to the exemplary embodiment may be solely used as the organic-EL-device material or may be used with other material(s) to provide the organic-EL-device material.

Organic EL Device

In the exemplary embodiment of the invention, an organic EL device includes: a cathode; an anode; and an organic layer provided between the cathode and the anode. The organic layer is configured to have a plurality of layers at least including an emitting layer.

In the organic EL device in the exemplary embodiment, the organic layer at least includes the emitting layer and further includes an electron transporting zone. The electron transporting zone is a layer provided between the emitting layer and the cathode and at least includes an electron injecting layer. The electron transporting zone may include the electron injecting layer and an electron transporting layer and may further include a hole blocking layer and a space layer. In addition to the above layers, the organic layer may be provided by layers applied in a known organic EL device such as a hole injecting layer, a hole transporting layer and an electron blocking layer. The organic layer may include an inorganic compound.

The organic EL device may be a fluorescent monochromatic emission device or a phosphorescent monochromatic emission device, or alternatively, may be a white-emitting hybrid device of the fluorescent and phosphorescent monochromatic emission devices.

The organic EL device may be in a simple structure having a single emitting unit or may be in a tandem structure including a plurality of emitting units. Among the above, a phosphorescent monochromatic emission device is preferable.

A representative device arrangement of the organic EL device having the simple structure is shown below.

(1) Anode/Emitting Unit/Cathode

The aforementioned emitting unit may be provided by laminating a plurality of phosphorescent-emitting layers and fluorescent-emitting layers. In this arrangement, a space layer may be provided between the emitting layers in order to prevent excitons generated in the phosphorescent-emitting layers from diffusing into the fluorescent-emitting layers. Representative examples of a layer arrangement of the emitting unit are given below:

(a) hole transporting layer/emitting layer (/electron transporting layer);
(b) hole transporting layer/first phosphorescent-emitting layer/second phosphorescent-emitting layer (/electron transporting layer);
(c) hole transporting layer/phosphorescent-emitting layer/space layer/fluorescent-emitting layer (/electron transporting layer);
(d) hole transporting layer/first phosphorescent-emitting layer/second phosphorescent-emitting layer/space layer/fluorescent-emitting layer (/electron transporting layer);
(e) hole transporting layer/first phosphorescent-emitting layer/space layer/second phosphorescent-emitting layer/space layer/fluorescent-emitting layer (/electron transporting layer);
(f) hole transporting layer/phosphorescent-emitting layer/space layer/first fluorescent-emitting layer/second fluorescent-emitting layer (/electron transporting layer);
(g) hole transporting layer/electron blocking layer/emitting layer (/electron transporting layer);
(h) hole transporting layer/emitting layer/hole blocking layer (/electron transporting layer); and
(i) hole transporting layer/fluorescent-emitting layer/triplet blocking layer (/electron transporting layer).

Each of the phosphorescent-emitting layers or the fluorescent-emitting layers in each of the above emitting units can exhibit different emission colors. Specifically, the above emitting unit (d) is in the layer arrangement of the hole transporting layer/first phosphorescent-emitting layer (red emission)/second phosphorescent-emitting layer (green emission)/space layer/fluorescent-emitting layer (blue emission)/electron transporting layer.

An electron blocking layer may be provided as needed between the emitting layer and the hole transporting layer or between the emitting layer and the space layer. Moreover, a hole blocking layer may be provided as needed between the emitting layer and the electron transporting layer. Provision of the electron blocking layer or the hole blocking layer enables electrons or holes to be trapped in the emitting layer(s), thereby enhancing probability of charge recombination in the emitting layer(s) to prolong a lifetime.

A representative device arrangement of the tandem-type organic EL device is shown below.

(2) Anode/First Emitting Unit/Intermediate Layer/Second Emitting Unit/Cathode

Herein, the first emitting unit and the second emitting unit can be independently the same as the aforementioned emitting units.

The intermediate layer is generally referred to as an intermediate electrode, intermediate conductive layer, charge generating layer, electron drawing layer, connection layer or intermediate insulative layer. The intermediate layer can be made of known materials that supply electrons to the first emitting unit and holes to the second emitting unit.

It should be noted that a host material combined with a fluorescent dopant is herein referred to as a fluorescent host while a host combined with a phosphorescent dopant is herein referred to as a phosphorescent host. The fluorescent host and the phosphorescent host are not differentiated only with respect to the molecular structures thereof. In other words, the phosphorescent host herein means a material for forming a phosphorescent-emitting layer containing a phosphorescent dopant, and does not mean to be inapplicable to a material for forming a fluorescent-emitting layer. The same applies to a fluorescent host.

FIG. 1 schematically shows an arrangement of the organic EL device according to the exemplary embodiment.

An organic EL device 1 shown in FIG. 1 includes a substrate 2, an anode 3, a cathode 4 and an organic layer 10 disposed between the anode 3 and the cathode 4.

The organic layer 10 includes a hole injecting/transporting layer 6, an emitting layer 5, an electron transporting layer 7 and an electron injecting layer 8 which are sequentially laminated from the anode 3. Among the above layers, the electron transporting layer 7 and the electron injecting layer 8 define an electron transporting zone 11.

Electron Transporting Zone

The electron transporting zone 11 of the organic EL device 1 according to the exemplary embodiment preferably contains the compound according the exemplary embodiment. In the exemplary embodiment, the electron transporting zone 11 includes the electron transporting layer 7 and the electron injecting layer 8. The compound according to the exemplary embodiment of the invention may be contained in any layer of the electron transporting zone 11. In the exemplary embodiment, the compound is contained in the electron injecting layer 8.

It is preferable that the electron transporting zone 11 in the exemplary embodiment also contains an electron-donating dopant described later.

Electron Injecting Layer

The electron injecting layer has a function to efficiently inject electrons from the cathode into an organic layer unit. When the electron transporting zone is provided by a plurality of layers, an organic layer close to the cathode is defined as the electron injecting layer. The electron injecting layer 8 in the exemplary embodiment contains the above-described compound according to the exemplary embodiment. Specifically, the electron injecting layer 8 contains the compound represented by any one of the formulae (1), (1A), (1B), (13A), (15A) to (16A), (12A-1) to (12A-2), and (12B-1) to (12B-2).

The compound represented by any one of the formulae (1), (1A), (1B), (13A), (15A) to (16A), (12A-1) to (12A-2), and (12B-1) to (12B-2) in the exemplary embodiment exhibits a high electron injecting performance by having a nitrogen-containing heterocyclic group represented by Az at a molecular terminal in the formula (1).

Electron Transporting Layer

The electron transporting layer 7 is an organic layer formed between the emitting layer and the cathode and has a function to transport electrons from the cathode to the emitting layer. The compound and the organic-EL-device material according to the exemplary embodiment are also suitable as an electron-transporting-layer material for forming the electron transporting layer.

The electron transporting material for forming the electron transporting layer in addition to the above organic-EL-device material is preferably an aromatic heterocyclic compound having at least one heteroatom in a molecule, particularly preferably a nitrogen-containing cyclic derivative. The nitrogen-containing cyclic derivative is preferably an aromatic ring having a nitrogen-containing six-membered or five-membered ring skeleton, or a fused aromatic cyclic compound having a nitrogen-containing six-membered or five-membered ring skeleton.

The nitrogen-containing cyclic derivative is preferably exemplified by a nitrogen-containing cyclic metal chelate complex represented by the following formula (A).

[Formula 45]

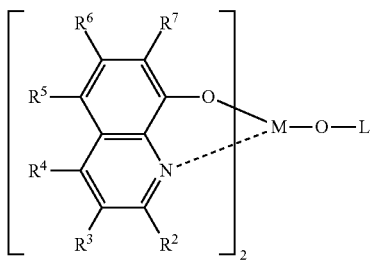

(A)

$R^2$ to $R^7$ in the formula (A) representing the nitrogen-containing cyclic metal chelate complex each independently represent a hydrogen atom, a halogen atom, a hydroxyl group, an amino group, a hydrocarbon group having 1 to 40 carbon atoms, an alkoxy group having 1 to 40 carbon atoms, an aryloxy group having 6 to 50 carbon atoms, an alkoxycarbonyl group, or a aromatic heterocyclic group having 5 to 50 ring carbon atoms. These groups may be substituted.

Examples of the halogen atom are fluorine, chlorine, bromine and iodine.

Examples of the substituted or unsubstituted amino group include an alkylamino group, an arylamino group, and an aralkylamino group.

The alkylamino group and the aralkylamino group are represented by $-NQ^1Q^2$. $Q^1$ and $Q^2$ each independently represent an alkyl group having 1 to 20 carbon atoms or an aralkyl group having 1 to 20 carbon atoms, One of $Q^1$ and $Q^2$ may be a hydrogen atom.

The arylamino group is represented by $-NAr^1Ar^2$. $Ar^1$ and $Ar^2$ represent a non-fused aromatic hydrocarbon group and fused aromatic hydrocarbon group having 6 to 50 carbon atoms. One of $Ar^1$ and $Ar^2$ may be a hydrogen atom.

Examples of the hydrocarbon group having 1 to 40 carbon atoms include an alkyl group, an alkenyl group, a cycloalkyl group, an aryl group, and an aralkyl group.

The alkoxycarbonyl group is represented by $-COOY'$. $Y'$ represents alkyl group having 1 to 20 carbon atoms.

M represents aluminum (Al), gallium (Ga) or indium (In), among which In is preferable.

L represents a group represented by a formula (A') or (A") below.

[Formula 46]

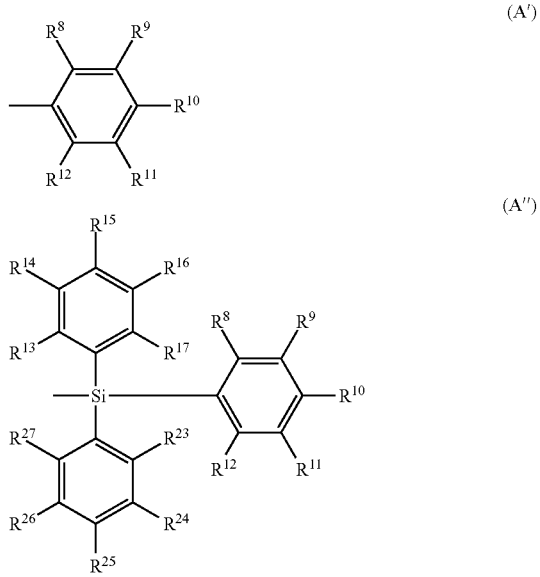

In the formula (A'), $R^8$ to $R^{12}$ each independently represent a hydrogen atom or a substituted or unsubstituted hydrocarbon group having 1 to 40 carbon atoms. Adjacent groups may form a cyclic structure. In the formula (A"), $R^{13}$ to $R^{27}$ each independently represent a hydrogen atom or a substituted or unsubstituted hydrocarbon group having 1 to 40 carbon atoms. Adjacent groups may form a cyclic structure.

The hydrocarbon group having 1 to 40 carbon atoms represented by each of $R^8$ to $R^{12}$ and $R^{13}$ to $R^{27}$ in the formulae (A') and (A") represents the same as the hydrocarbon group represented by each of $R^2$ to $R^7$ in the formula (A) representing the nitrogen-containing cyclic metal chelate complex. Examples of a divalent group formed when adjacent groups of $R^8$ to $R^{12}$ and $R^{13}$ to $R^{27}$ forms a cyclic structure are a tetramethylene group, a pentamethylene group, a hexamethylene group, a diphenylmethane-2,2'-diyl group, a diphenylethane-3,3'-diyl group and a diphenylpropane-4,4'-diyl group.

As an electron transporting compound for the electron transporting layer, 8-hydroxyquinoline or a metal complex of its derivative, an oxadiazole derivative and a nitrogen-containing heterocyclic derivative are preferable. A specific example of the 8-hydroxyquinoline or the metal complex of its derivative is a metal chelate oxinoid compound containing a chelate of oxine (typically 8-quinolinol or 8-hydroxyquinoline). For instance, tris(8-quinolinol) aluminum can be used. Examples of the oxadiazole derivative are as follows.

[Formula 47]

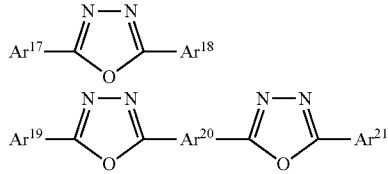

-continued

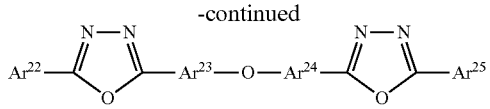

In the formula, $Ar^{17}$, $Ar^{18}$, $Ar^{19}$, $Ar^{21}$, $A^{22}$ and $Ar^{25}$ each represent a substituted or unsubstituted aromatic hydrocarbon group or fused aromatic hydrocarbon group having 6 to 50 carbon atoms. $Ar^{17}$, $Ar^{19}$ and $Ar^{22}$ may be the same as or different from $Ar^{18}$, $Ar^{21}$ and $Ar^{25}$, respectively. Examples of the aromatic hydrocarbon group or fused aromatic hydrocarbon group are a phenyl group, naphthyl group, biphenyl group, anthranil group, perylenyl group and pyrenyl group. Examples of the substituent therefor are an alkyl group having 1 to 10 carbon atoms, an alkoxy group having 1 to 10 carbon atoms or a cyano group.

$Ar^{20}$, $Ar^{23}$ and $Ar^{24}$ each represent a substituted or unsubstituted divalent aromatic hydrocarbon group or fused aromatic hydrocarbon group having 6 to 50 carbon atoms. $Ar^{23}$ and $Ar^{24}$ may be mutually the same or different. Examples of the divalent aromatic hydrocarbon group or fused aromatic hydrocarbon group are a phenylene group, naphthylene group, biphenylene group, anthranylene group, perylenylene group and pyrenylene group. Examples of the substituent therefor are an alkyl group having 1 to 10 carbon atoms, an alkoxy group having 1 to 10 carbon atoms or a cyano group.

An electron transporting compound having a favorable thin-film formability is usable for the electron transporting layer. Examples of the electron transporting compound are as follows.

represented by a formula (B) and a compound having a structure represented by a formula (C).

[Formula 49]

 (B)

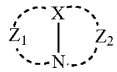 (C)

In the formula (C), X represents a carbon atom or a nitrogen atom. $Z_1$ and $Z_2$ each independently represent a group of atoms capable of forming a nitrogen-containing heterocycle.

Preferably, the nitrogen-containing heterocyclic derivative is an organic compound having a nitrogen-containing aromatic polycyclic group having a five-membered ring or six-membered ring. When the nitrogen-containing heterocyclic derivative includes such nitrogen-containing aromatic polycycles having a plurality of nitrogen atoms, the nitrogen-containing heterocyclic derivative may be a nitrogen-containing aromatic polycyclic organic compound having a skeleton formed by a combination of the skeletons respectively represented by the formulae (B) and (C), or by a combination of the skeletons respectively represented by the formulae (B) and (D).

[Formula 48]

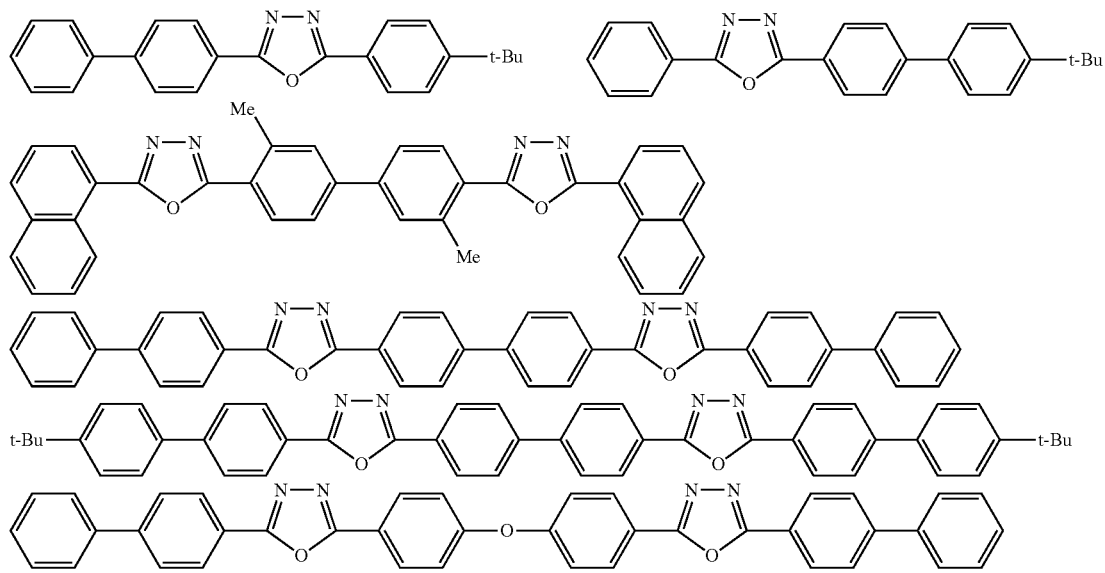

An example of the nitrogen-containing heterocyclic derivative as the electron transporting compound is a nitrogen-containing compound that is not a metal complex, the derivative being formed of an organic compound represented by one of the following formulae. Examples of the nitrogen-containing heterocyclic derivative as the electron transporting compound are a compound having a five-membered ring or six-membered ring having a skeleton

[Formula 50]

 (D)

A nitrogen-containing group of the nitrogen-containing aromatic polycyclic organic compound is selected from nitrogen-containing heterocyclic groups respectively represented by the following formulae.

[Formula 51]

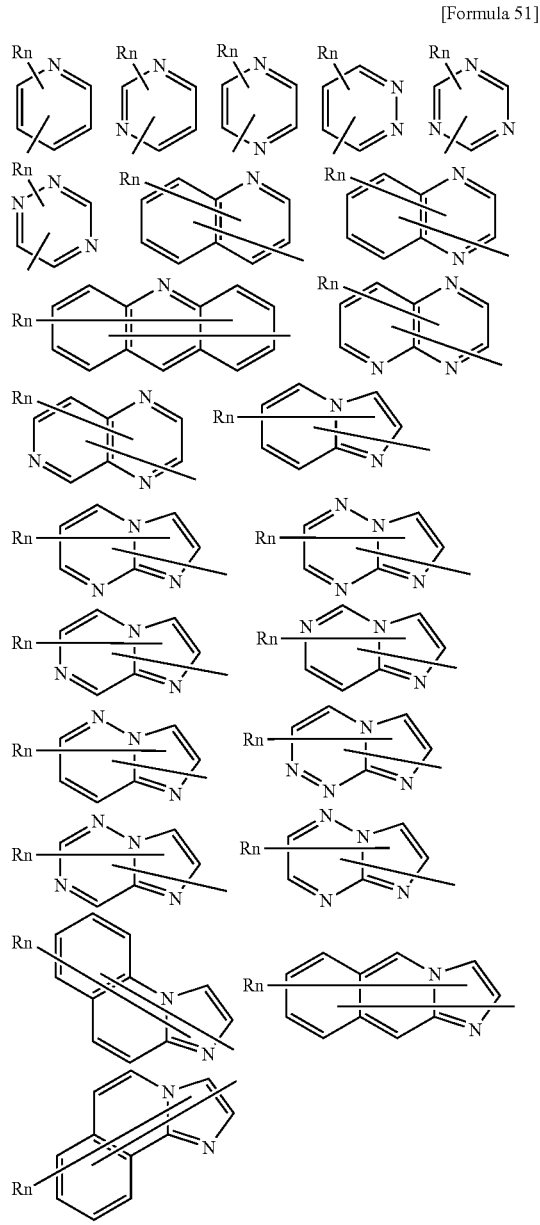

In the formulae: R represents an aromatic hydrocarbon group or fused aromatic hydrocarbon group having 6 to 40 carbon atoms; aromatic heterocyclic group or fused aromatic heterocyclic group having 3 to 40 carbon atoms; alkyl group having 1 to 20 carbon atoms or alkoxy group having 1 to 20 carbon atoms; and n represents an integer of 0 to 5. When n is an integer of 2 or more, the plurality of R may be mutually the same or different.

A preferable specific compound is a nitrogen-containing heterocyclic derivative represented by a formula (D1) below.

$$HAr\text{-}L^1\text{-}Ar^1\text{---}Ar^2 \qquad (D1)$$

In the formula (D1): HAr represents a substituted or unsubstituted nitrogen-containing heterocyclic group having 3 to 40 carbon atoms; $L^1$ represents a single bond, substituted or unsubstituted aromatic hydrocarbon group or fused aromatic hydrocarbon group having 6 to 40 carbon atoms, or substituted or unsubstituted aromatic heterocyclic group or fused aromatic heterocyclic group having 3 to 40 carbon atoms; $Ar^1$ represents a substituted or unsubstituted divalent aromatic hydrocarbon group having 6 to 40 carbon atoms; and $Ar^2$ represents a substituted or unsubstituted aromatic hydrocarbon group or fused aromatic hydrocarbon group having 6 to 40 carbon atoms, or substituted or unsubstituted aromatic heterocyclic group or fused aromatic heterocyclic group having 3 to 40 carbon atoms.

HAr is exemplarily selected from the following group.

[Formula 52]

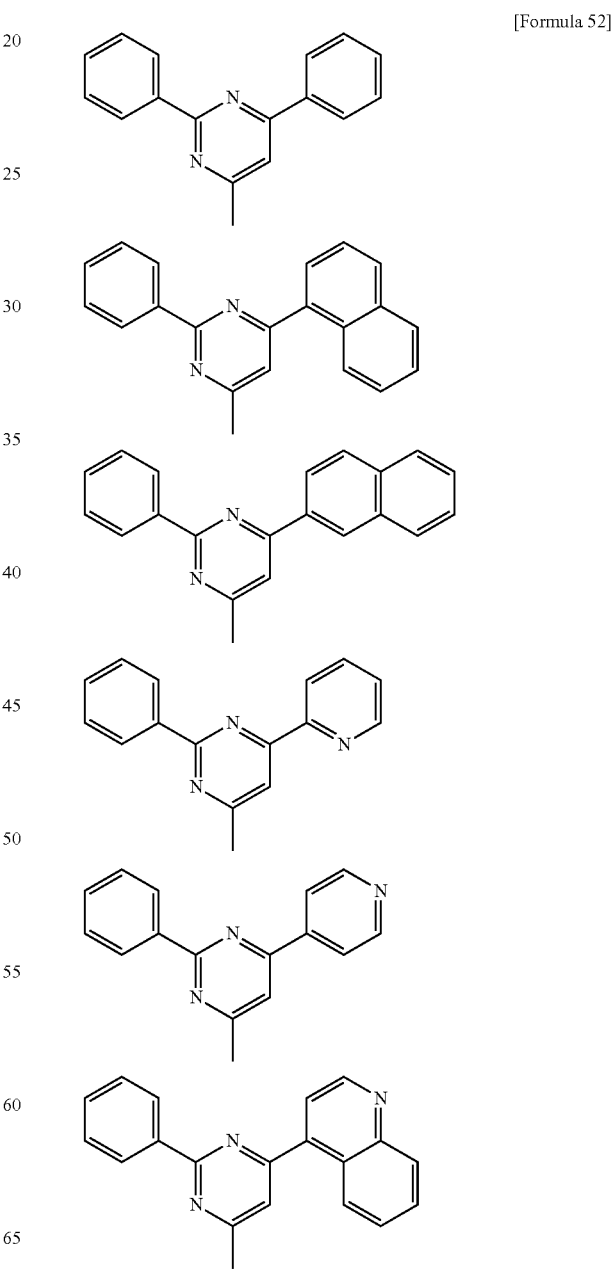

-continued

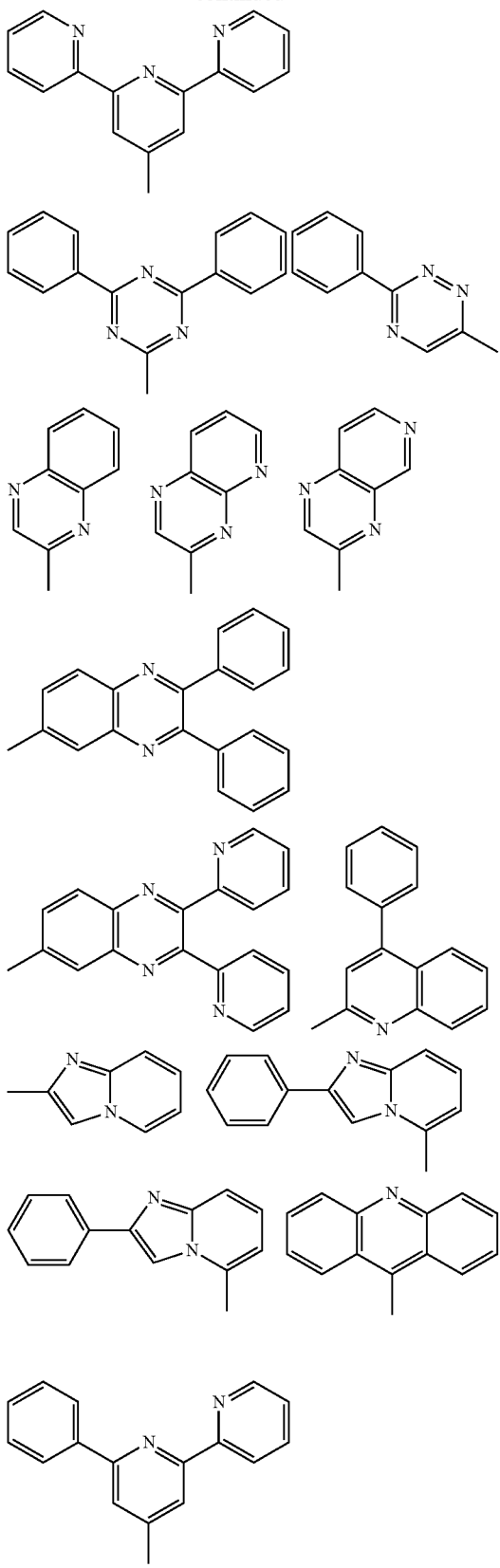

In the formula (D1), $L^1$ is exemplarily selected from the following group.

[Formula 53]

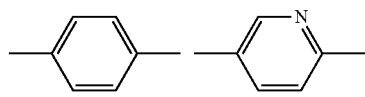

In the formula (D1), $Ar^1$ is exemplarily selected from an arylanthranil group represented by the formulae (D2) and (D3).

[Formula 54]

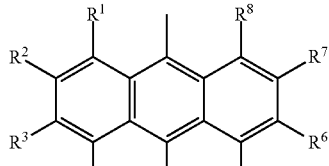
(D2)

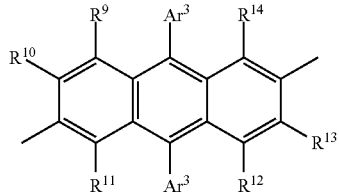
(D3)

In the formulae (D2) and (D3): $R^1$ to $R^{14}$ each independently represent a hydrogen atom, halogen atom, alkyl group having 1 to 20 carbon atoms, alkoxy group having 1 to 20 carbon atoms, aryloxy group having 6 to 40 carbon atoms, substituted or unsubstituted aromatic hydrocarbon group or fused aromatic hydrocarbon group having 6 to 40 carbon atoms, or aromatic heterocyclic group or fused aromatic heterocyclic group having 3 to 40 carbon atoms; and $Ar^3$ represents a substituted or unsubstituted aromatic hydrocarbon group having 6 to 40 carbon atoms or fused aromatic hydrocarbon group, or a substituted or unsubstituted aromatic heterocyclic group or fused aromatic heterocyclic group having 3 to 40 carbon atoms. All of $R^1$ to $R^8$ of a nitrogen-containing heterocyclic derivative may be hydrogen atoms.

In the formula (D1), $Ar^2$ is exemplarily selected from the following group.

[Formula 55]

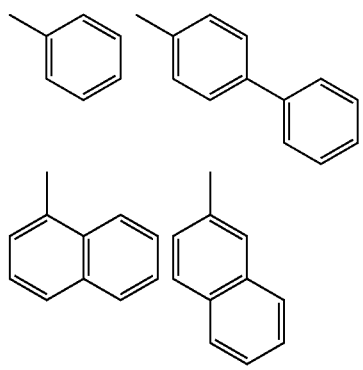

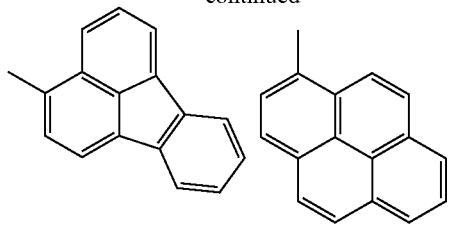

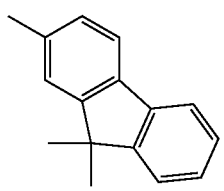

In addition to the above, a compound represented by a formula (D4) can be favorably used as the nitrogen-containing aromatic polycyclic organic compound (i.e., the electron transporting compound).

[Formula 56]

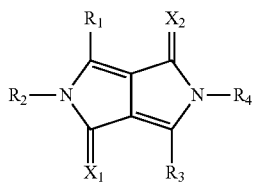

In the formula (D4): $R_1$ to $R_4$ each independently represent a hydrogen atom, substituted or unsubstituted aliphatic group having 1 to 20 carbon atoms, substituted or unsubstituted alicyclic group having 3 to 20 carbon atoms, substituted or unsubstituted aromatic cyclic group having 6 to 50 carbon atoms, or substituted or unsubstituted heterocyclic group having 3 to 50 carbon atoms; and $X_1$ and $X_2$ each independently represent an oxygen atom, sulfur atom or dicyanomethylene group.

A compound represented by a formula (D5) below can also be favorably used as the electron transporting compound.

[Formula 57]

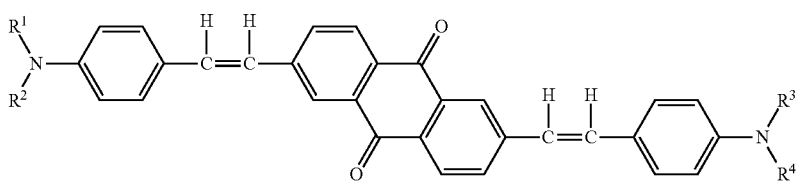

In the formula (D5), $R^1$, $R^2$, $R^3$ and $R^4$, which may be mutually the same or different, each represent an aromatic hydrocarbon group represented by a formula (D6) below or a fused aromatic hydrocarbon group.

[Formula 58]

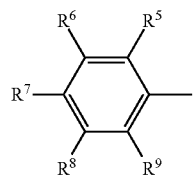

In the formula (D6), $R^5$, $R^6$, $R^7$, $R^8$ and $R^9$, which may be mutually the same or different, each represent a hydrogen atom, a saturated or unsaturated alkoxyl group having 1 to 20 carbon atoms, saturated or unsaturated alkyl group having 1 to 20 carbon atoms, an amino group, or an alkylamino group having 1 to 20 carbon atoms. At least one of $R^5$, $R^6$, $R^7$, $R^8$ and $R^9$ is a group other than a hydrogen atom.

A polymer compound containing the nitrogen-containing heterocyclic group or a nitrogen-containing heterocyclic derivative may be used for the electron transporting compound.

The electron transporting layer of the organic EL device in the exemplary embodiment preferably contains at least one of nitrogen-containing heterocycle derivatives represented by formulae (E) to (G) below.

[Formula 59]

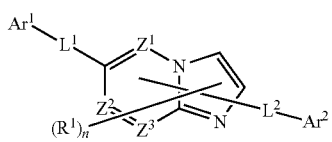

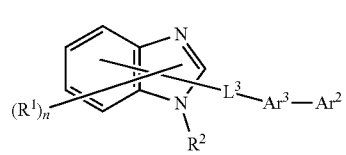

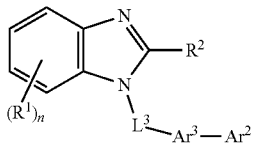

(G)

In the formulae (E) to (G), $Z^1$, $Z^2$ and $Z^3$ each independently represent a nitrogen atom or a carbon atom.

$R^1$ and $R^2$ each independently represent a substituted or unsubstituted aryl group having 6 to 50 ring carbon atoms, substituted or unsubstituted heteroaryl group having 5 to 50 ring atoms, substituted or unsubstituted alkyl group having 1 to 20 carbon atom, substituted or unsubstituted haloalkyl group having 1 to 20 carbon atoms, or substituted or unsubstituted alkoxy group having 1 to 20 carbon atom.

n is an integer of 0 to 5. When n is an integer of 2 or more, a plurality of $R^1$ may be mutually the same or different. Adjacent two $R^1$ may be mutually bonded to form a substituted or unsubstituted hydrocarbon ring.

$Ar^1$ represents a substituted or unsubstituted aryl group having 6 to 50 ring carbon atoms or a substituted or unsubstituted heteroaryl group having 5 to 50 ring atoms.

$Ar^2$ represents a hydrogen atom, substituted or unsubstituted alkyl group having 1 to 20 carbon atoms, substituted or unsubstituted haloalkyl group having 1 to 20 carbon atoms, substituted or unsubstituted alkoxy group having 1 to 20 carbon atoms, substituted or unsubstituted aryl group having 6 to 50 ring carbon atoms, or substituted or unsubstituted heteroaryl having 5 to 50 ring atoms.

However, one of $Ar^1$ and $Ar^2$ is a substituted or unsubstituted fused aromatic hydrocarbon group having 10 to 50 ring carbon atoms, or substituted or unsubstituted fused aromatic heterocyclic group having 9 to 50 ring atoms.

$Ar^3$ represents a substituted or unsubstituted arylene group having 6 to 50 ring carbon atoms or a substituted or unsubstituted heteroarylene group having 5 to 50 ring atoms.

$L^1$, $L^2$ and $L^3$ each independently represent a single bond, a substituted or unsubstituted arylene group having 6 to 50 ring carbon atoms, or a substituted or unsubstituted divalent fused aromatic heterocyclic group having 9 to 50 ring atoms.

Examples of the aryl group having 6 to 50 ring carbon atoms are a phenyl group, naphthyl group, anthryl group, phenanthryl group, naphthacenyl group, chrysenyl group, pyrenyl group, biphenyl group, terphenyl group, tolyl group, fluoranthenyl group and fluorenyl group.

Examples of the heteroaryl group having 5 to 50 ring atoms are a pyrrolyl group, furyl group, thienyl group, silolyl group, pyridyl group, quinolyl group, isoquinolyl group, benzofuryl group, imidazolyl group, pyrimidyl group, carbazolyl group, selenophenyl group, oxadiazolyl group, triazolyl group, pyrazinyl group, pyridazynyl group, triazinyl group, quinoxalinyl group, acridinyl group, imidazo[1,2-a]pyridinyl group, and imidazo[1,2-a]pyrimidinyl group.

Examples of the alkyl group having 1 to 20 carbon atoms are a methyl group, ethyl group, propyl group, butyl group, pentyl group and hexyl group.

The haloalkyl group having 1 to 20 carbon atoms is exemplified by a haloalkyl group provided by substituting one or more hydrogen atoms of the alkyl group with one or more halogen atoms selected from fluorine, chlorine, iodine and bromine.

The alkoxy group having 1 to 20 carbon atoms is exemplified by an alkoxy group having the above alkyl group in an alkyl moiety.

Examples of the arylene group having 6 to 50 ring carbon atoms are groups obtained by eliminating one hydrogen atom from the above aryl groups.

Examples of the divalent fused aromatic heterocyclic group having 9 to 50 ring atoms are groups obtained by eliminating one hydrogen atom from the above fused aromatic heterocyclic groups described as the heteroaryl group.

Although a thickness of the electron transporting layer is not specifically limited, the thickness is preferably 1 nm to 100 nm.

The electron transporting zone 11 of the organic EL device 1 may include a second electron injecting layer in addition to the electron injecting layer 8. The second electron injecting layer is interposed between the electron transporting layer and the electron injecting layer 8. The second electron injecting layer preferably contains an inorganic compound such as an insulator or a semiconductor in addition to the nitrogen-containing cyclic derivative. Such an insulator or a semiconductor, when contained in the second electron injecting layer, can effectively prevent a current leak, thereby enhancing electron capability of the electron injecting layer.

As the insulator, it is preferable to use at least one metal compound selected from the group consisting of an alkali metal chalcogenide, an alkaline-earth metal chalcogenide, a halogenide of alkali metal and a halogenide of alkaline-earth metal. Forming the second electron injecting layer from the alkali metal chalcogenide or the like is preferable for further enhancement of the electron injectability. Specifically, preferred examples of the alkali metal chalcogenide are $Li_2O$, $K_2O$, $Na_2S$, $Na_2Se$ and $Na_2O$, while preferable example of the alkaline-earth metal chalcogenide are CaO, BaO, SrO, BeO, BaS and CaSe.

Preferred examples of the halogenide of the alkali metal are LiF, NaF, KF, LiCl, KCl and NaCl. Preferred examples of the halogenide of the alkaline-earth metal are fluorides such as $CaF_2$, $BaF_2$, $SrF_2$, $MgF_2$ and $BeF_2$, and halogenides other than the fluoride.

Examples of the semiconductor are one of or a combination of two or more of an oxide, a nitride or an oxidized nitride containing at least one element selected from Ba, Ca, Sr, Yb, Al, Ga, In, Li, Na, Cd, Mg, Si, Ta, Sb and Zn. An inorganic compound for forming the second electron injecting layer is preferably a microcrystalline or amorphous semiconductor film. When the second electron injecting layer is formed of such a semiconductor film, more uniform thin film can be formed, thereby reducing pixel defects such as a dark spot. Examples of such an inorganic compound are the alkali metal chalcogenide, alkaline-earth metal chalcogenide, halogenide of the alkali metal and halogenide of the alkaline-earth metal.

When the electron injecting layer contains such an insulator or such a semiconductor, a thickness thereof is preferably in a range of approximately 0.1 nm to 15 nm.

Electron-donating Dopant and Organic Metal Complex

In the organic EL device according to this exemplary embodiment, at least one of an electron-donating dopant and an organic metal complex is preferably contained in an interfacial region between the electron transporting zone and the organic layer or between the cathode and the organic layer.

With this arrangement, the organic EL device can emit light with enhanced luminance intensity and have a longer lifetime.

The electron-donating dopant may be at least one selected from an alkali metal, an alkali metal compound, an alkaline-earth metal, an alkaline-earth metal compound, a rare-earth metal, a rare-earth metal compound and the like.

The organic metal complex may be at least one selected from an organic metal complex including an alkali metal, an organic metal complex including an alkaline-earth metal, and an organic metal complex including rare-earth metal.

Examples of the alkali metal are lithium (Li) (work function: 2.93 eV), sodium (Na) (work function: 2.36 eV), potassium (K) (work function: 2.28 eV), rubidium (Rb) (work function: 2.16 eV) and cesium (Cs) (work function: 1.95 eV), among which alkali metal having a work function of 2.9 eV or less is preferable. Among the above, the alkali metal is preferably K, Rb or Cs, more preferably Rb or Cs, further preferably Cs.

Examples of the alkaline-earth metal are calcium (Ca) (work function: 2.9 eV), strontium (Sr) (work function: 2.0 to 2.5 eV), and barium (Ba) (work function: 2.52 eV), among which alkaline-earth metal having a work function of 2.9 eV or less is preferable.

Examples of the rare-earth metal are scandium (Sc), yttrium (Y), cerium (Ce), terbium (Tb) and ytterbium (Yb), among which rare-earth metal having a work function of 2.9 eV or less is particularly preferable.

Since the above preferred metals have particularly high reduction-causing performance, addition of a relatively small amount of the metals to an electron injecting zone can enhance luminance intensity and lifetime of the organic EL device.

Examples of the alkali metal compound are an alkali oxide such as lithium oxide ($Li_2O$), cesium oxide ($Cs_2O$) and potassium oxide ($K_2O$), and an alkali halogenide such as sodium fluoride (NaF), cesium fluoride (CsF) and potassium fluoride (KF), among which lithium fluoride (LiF), lithium oxide ($Li_2O$) and sodium fluoride (NaF) are preferable.

Examples of the alkaline earth metal oxide are barium oxide (BaO), strontium oxide (SrO), and calcium oxide (CaO). Examples of the alkaline earth metal compound further include barium strontium oxide ($Ba_xSr_{1-x}O$) (0<x<1) that is a mixture of BaO and SrO and brium calcium oxide ($Ba_xCa_{1-x}O$) (0<x<1) that is a mixture of BaO and CaO. BaO, SrO and CaO are preferable as the alkaline earth metal compound.

Examples of the rare-earth metal compound are ytterbium fluoride ($YbF_3$), scandium fluoride ($ScF_3$), scandium oxide ($ScO_3$), yttrium oxide ($Y_2O_3$), cerium oxide ($Ce_2O_3$), gadolinium fluoride ($GdF_3$) and terbium fluoride ($TbF_3$), among which $YbF_3$, $ScF_3$ and $TbF_3$ are preferable.

The alkali metal complex is not particularly limited, as long as at least one of alkali metal ion, alkaline-earth metal ion and rare-earth metal ion is contained therein as metal ion. The ligand for each of the organic metal complexes is preferably quinolinol, benzoquinolinol, acridinol, phenanthridinol, hydroxyphenyl oxazole, hydroxyphenyl thiazole, hydroxydiaryl oxadiazole, hydroxydiaryl thiadiazole, hydroxyphenyl pyridine, hydroxyphenyl benzoimidazole, hydroxybenzo triazole, hydroxy fluborane, bipyridyl, phenanthroline, phthalocyanine, porphyrin, cyclopentadiene, β-diketones, azomethines, or a derivative thereof, but the ligand is not limited thereto.

The electron-donating dopant and the organic metal complex are added to preferably form a layer or an island pattern in the interfacial region. The layer of the electron-donating dopant or the island pattern of the organic metal complex is preferably formed by: depositing at least one of the electron-donating dopant and the organic metal complex while simultaneously depositing an organic substance that is an emitting material or an electron-injecting material for forming the interfacial region, by resistance heating deposition; and dispersing at least one of the electron-donating dopant and an organic metal complex reduction-causing dopant in the organic substance. Dispersion concentration at which the electron-donating dopant is dispersed in the organic substance is a mole ratio (the organic substance to the electron-donating dopant or the organic metal complex) of 100:1 to 1:100, preferably 5:1 to 1:5.

When at least one of the electron-donating dopant and the organic metal complex forms a layer, the emitting material or the electron injecting material for forming the organic layer of the interfacial region is initially layered, and then, at least one of the electron-donating dopant and the organic metal complex is singularly evaporated thereon by resistance heating evaporation to preferably form a 0.1 nm- to 15 nm-thick layer.

When at least one of the electron-donating dopant and the organic metal complex forms an island pattern, the emitting material or the electron injecting material for forming the organic layer of the interfacial region is initially layered, and then, at least one of the electron-donating dopant is singularly evaporated thereon by resistance heating evaporation to preferably form a 0.05 nm- to 1 nm-thick island pattern.

A ratio of the main component to at least one of the electron-donating dopant and the organic metal complex in the organic EL device according to the exemplary embodiment is preferably a mole ratio (the main component to the electron-donating dopant or the organic metal complex) of 5:1 to 1:5, more preferably 2:1 to 1:2.

Substrate

The organic EL device according to the exemplary embodiment is formed on a light-transmissive substrate. The light-transmissive plate, which supports the organic EL device, is preferably a smoothly-shaped substrate that transmits 50% or more of light in a visible region of 400 nm to 700 nm. Specifically, examples of the substrate are a glass plate and a polymer plate. For the glass plate, materials such as soda-lime glass, barium/strontium-containing glass, lead glass, aluminosilicate glass, borosilicate glass, barium borosilicate glass and quartz can be used. The polymer plate is exemplified by a polymer plate provided by using materials such as polycarbonate, acryl, polyethylene terephthalate, polyether sulfide and polysulfone.

Anode

The anode of the organic EL device is used for injecting holes into the hole transporting layer or the emitting layer. It is effective to use a material having a work function of 4.5 eV or more as the anode. Specific examples of a material for the anode are alloys of indium-tin oxide (ITO), tin oxide (NESA), indium zinc oxide, gold, silver, platinum and copper. An anode can be prepared by forming a thin film out of these electrode materials by vapor deposition, sputtering, or the like. When light from the emitting layer is to be emitted through the anode, the anode preferably transmits more than 10% of the light in the visible region. Sheet resistance of the anode is preferably several hundreds Ω/square or lower. Although depending on the material for the anode, thickness of the anode is typically in a range of 10 nm to 1 μm, and preferably in a range of 10 nm to 200 nm.

Cathode

The cathode is used for injecting electrons into the electron injecting layer, the electron transporting layer or the emitting layer and is preferably formed of a material with smaller work function. Although a material for the cathode is not limited, examples of the material are indium, aluminum, magnesium, alloy of magnesium and indium, alloy of magnesium and aluminum, alloy of aluminum and lithium, alloy of aluminum, scandium and lithium, and alloy of magnesium and silver. Like the anode, the cathode may be made by forming a thin film from the above materials through a method such as vapor deposition or sputtering. In addition, the light may be emitted as needed through the cathode.

Emitting Layer

The emitting layer is an organic layer having an emission function and contains a host and a dopant when a doping system is employed. At this time, the host has a function to mainly promote recombination of electrons and holes and trap excitons within the emitting layer while the dopant has a function to promote an efficient emission from the excitons obtained by the recombination.

In a phosphorescent device, the host has a function of trapping the excitons, which are generated mainly in the dopant, within the emitting layer.

Herein, the emitting layer may include, for instance, double hosts (i.e., a host and a co-host) such as a combination of an electron transporting host and a hole transporting host, the double hosts adjusting carrier balance in the emitting layer.

The emitting layer may be a double-dopant layer in which at least two kinds of dopant materials having a high quantum efficiency are introduced and each of the dopants emits. Specifically, a host, a red dopant and a green dopant are co-evaporated on the emitting layer, whereby the emitting layer is commonly used to emit yellow light.

When the emitting layer is a laminate in which a plurality of emitting layers are laminated, electrons and holes are accumulated at the interface of the emitting layers, whereby a recombination region concentrates on the interface of the emitting layers to improve the quantum efficiency.

Injectability into the emitting layer of the holes may differ from that of the electrons and transporting capabilities of the hole and the electrons (represented by mobilities of the holes and the electrons in the emitting layer) may differ from each other.

As a method of forming the emitting layer, known methods such as vapor deposition, spin coating and an LB (Langmuir Blodgett) method may be employed. The emitting layer can be formed from a thin film formed by spin coating or the like, the thin film being formed from a solution prepared by dissolving a binder (e.g. a resin) and a material compound in a solvent.

The emitting layer is preferably a molecular deposit film. The molecular deposit film means a thin film formed by depositing a material compound in gas phase or a film formed by solidifying a material compound in a solution state or in liquid phase. The molecular deposit film is typically distinguished from a thin film formed by the LB method (molecular accumulation film) by differences in aggregation structures, higher order structures and functional differences arising therefrom.

The dopant is selected from a fluorescent dopant generating fluorescent emission and a phosphorescent dopant generating phosphorescent emission.

The phosphorescent dopant forming the emitting layer is a compound capable of emitting light from a triplet state. The phosphorescent dopant is not particularly limited as long as emitting light from the triplet state, but is preferably an organic metal complex including: at least one metal selected from Ir, Pt, Os, Au, Cu, Re and Ru; and a ligand. The ligand preferably has an ortho-metal bond. The phosphorescent dopant is preferably a metal complex containing a metal selected from Ir, Os and Pt because such a metal complex, which exhibits high phosphorescence quantum yield, can further enhance external quantum efficiency of the organic EL device. The phosphorescent dopant is more preferably a metal complex such as an iridium complex, osmium complex or platinum complex, and an ortho-metalated complex, among which an iridium complex and platinum complex are further preferable and an ortho-metalated iridium complex is more further preferable.

A content of the phosphorescent dopant in the emitting layer is not particularly limited. Although the content thereof can be selected according to the need, for instance, the content thereof is preferably in a range of 0.1 mass % to 70 mass %, more preferably of 1 mass % to 30 mass %. When the content of the phosphorescent dopant is 0.1 mass % or more, a sufficient emission is obtained. When the content of the phosphorescent dopant is 70 mass % or less, concentration quenching is avoidable.

Specific examples of the organic metal complex suitable as the phosphorescent dopant are shown below.

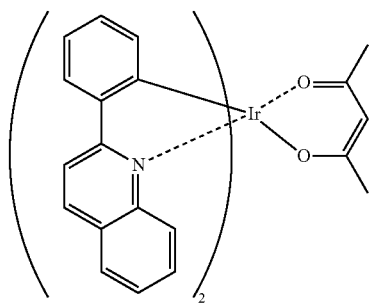

[Formula 60]

PQir

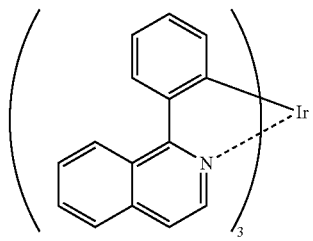

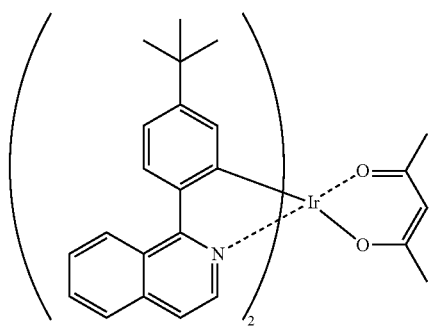

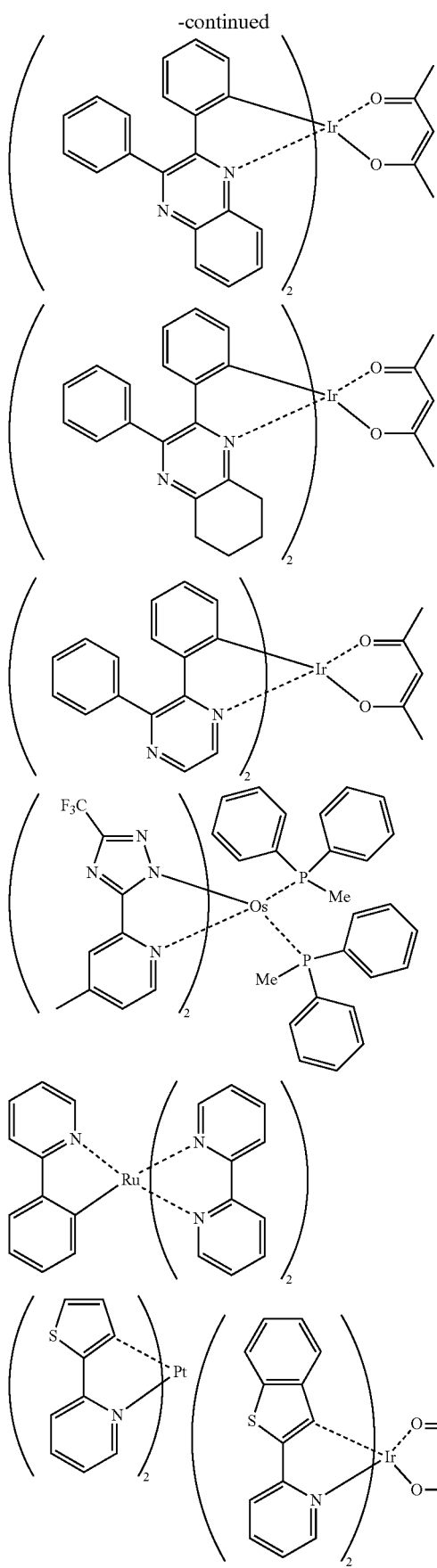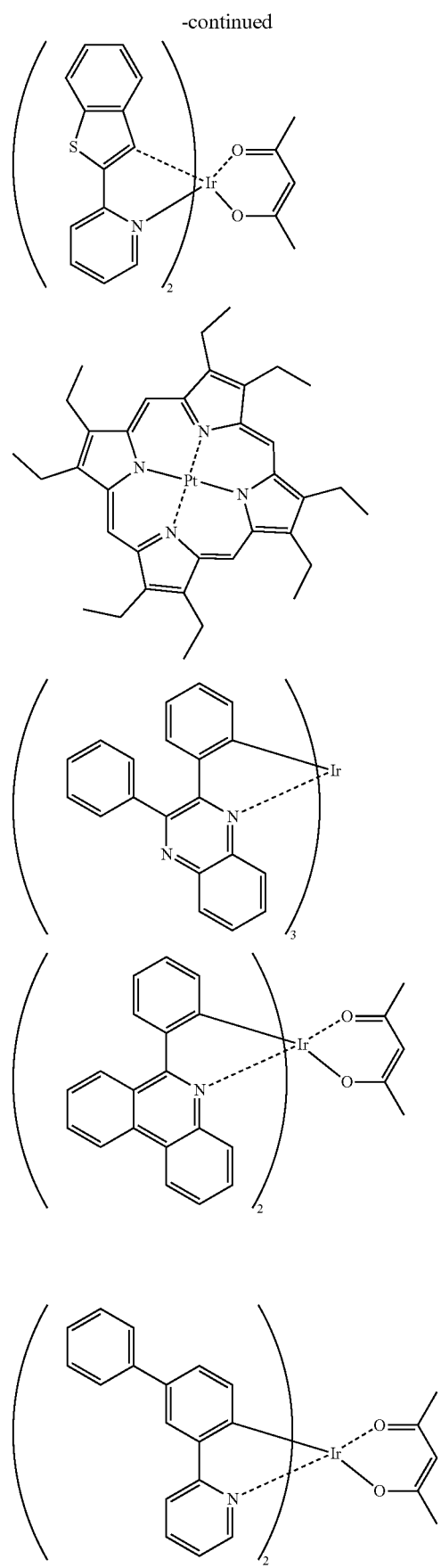

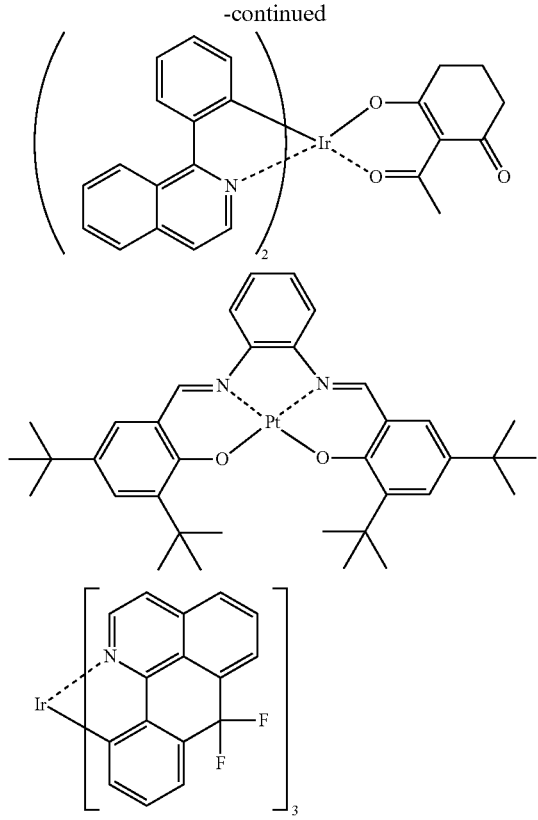
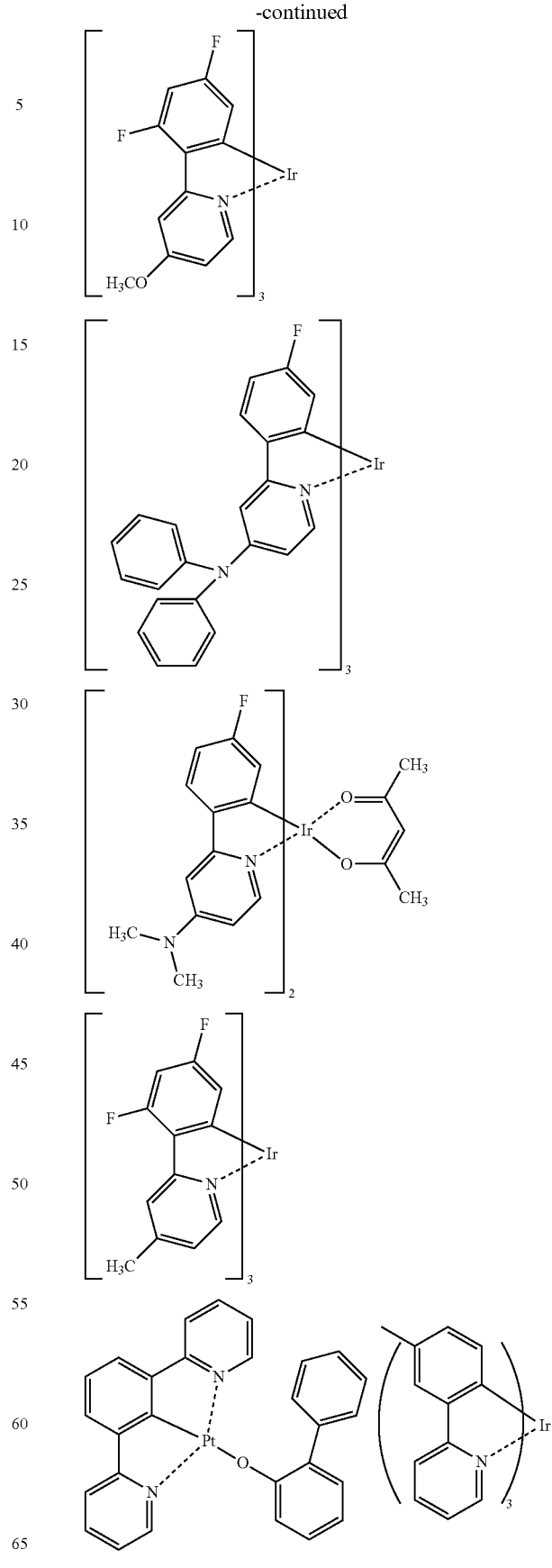
[Formula 61]

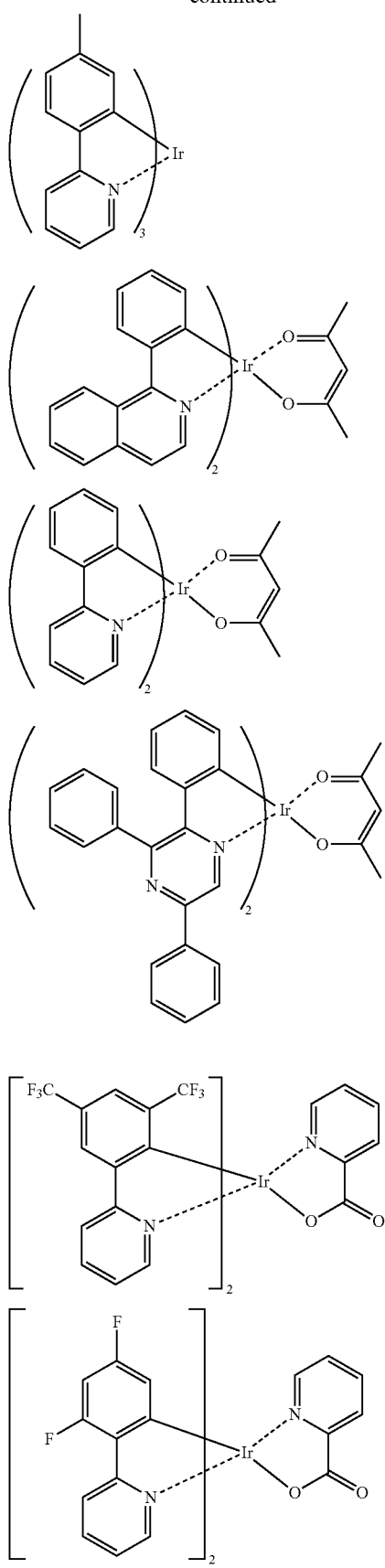
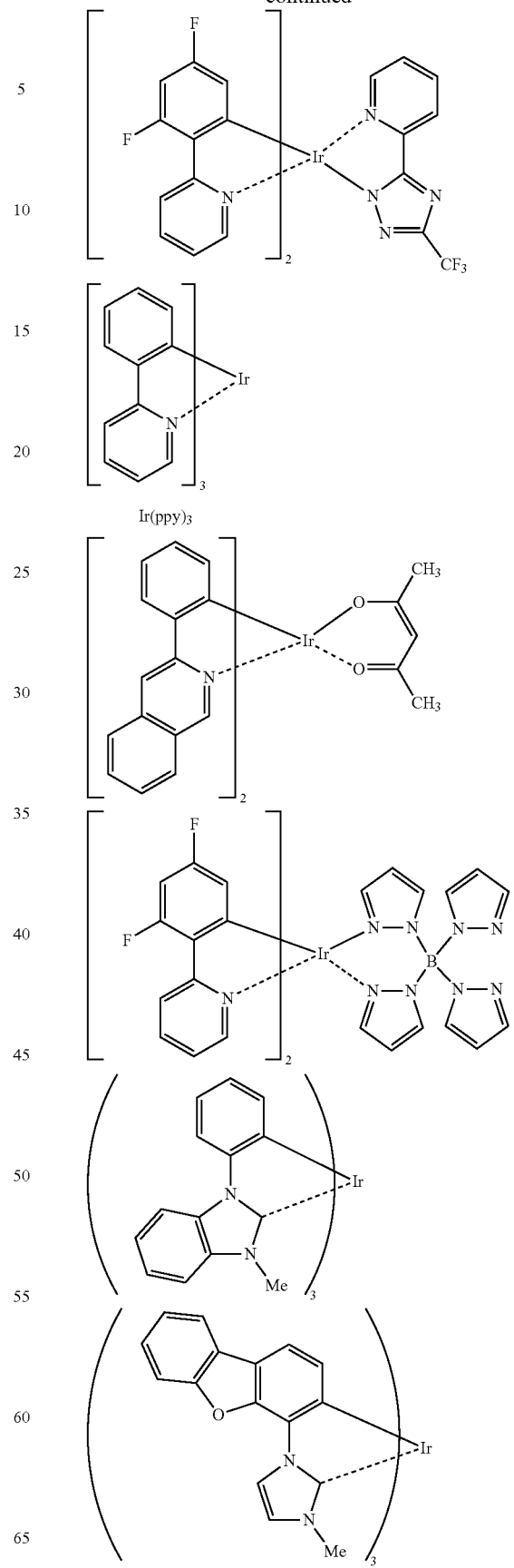

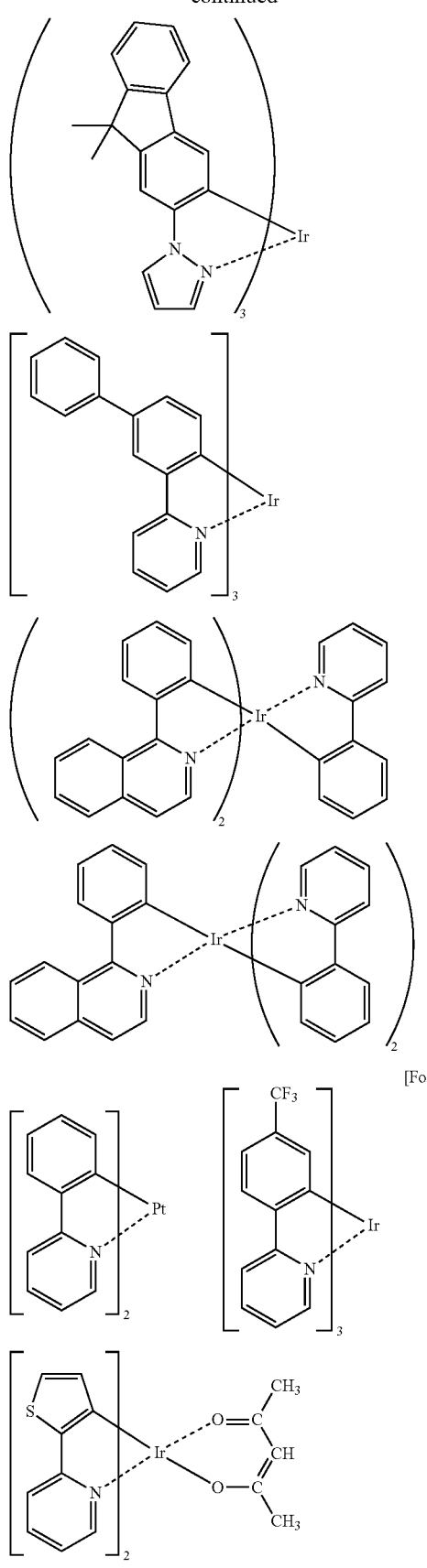
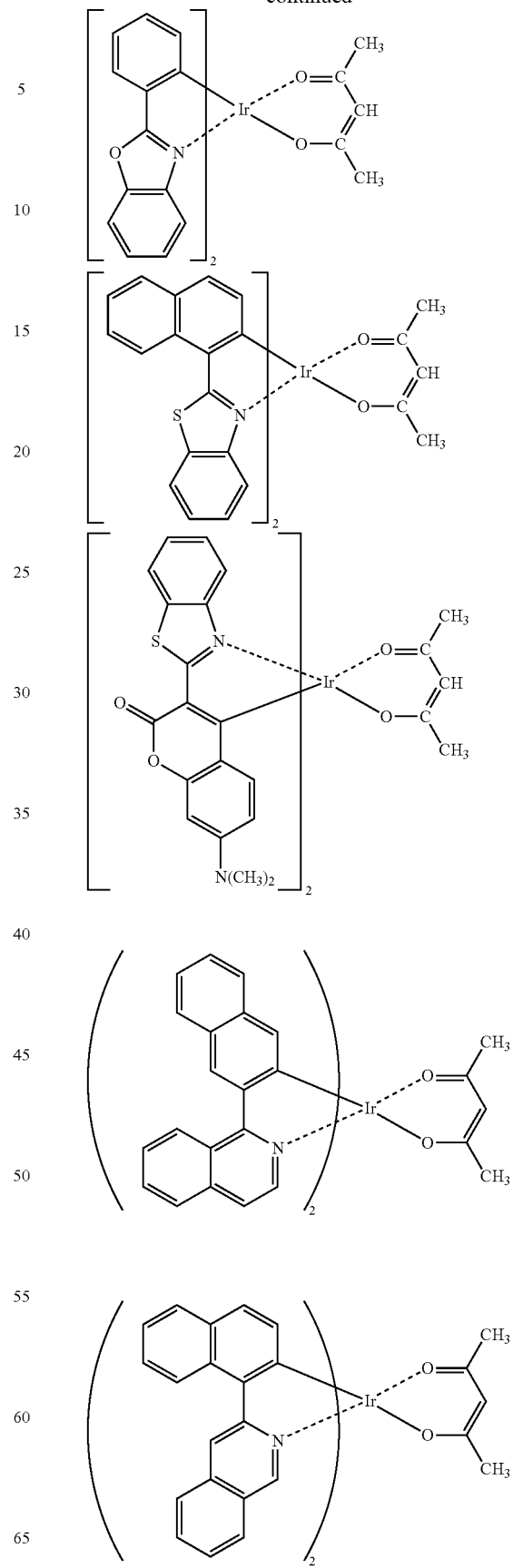
[Formula 63]

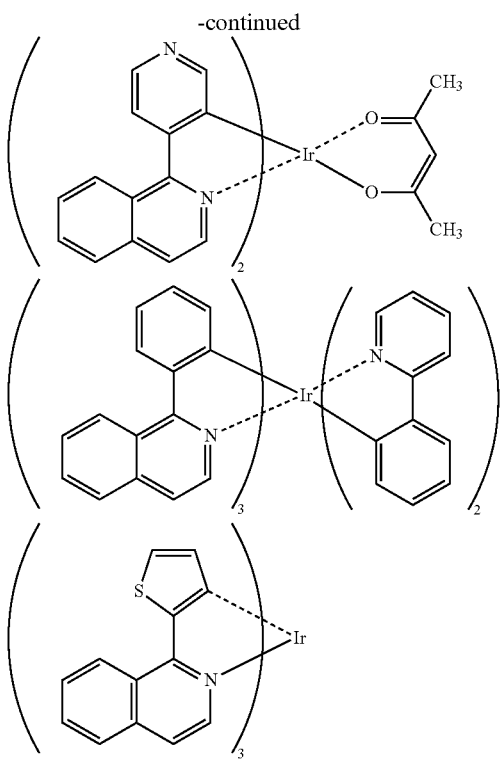

The phosphorescent host is a compound having a function to enable the phosphorescent dopant to emit efficiently by efficiently trapping triplet energy of the phosphorescent dopant in the emitting layer.

In the organic EL device of the exemplary embodiment, an emission wavelength of the phosphorescent dopant material contained in the emitting layer is not particularly limited. At least one of the phosphorescent dopant material contained in the emitting layer preferably emits light having the emission wavelength of 490 to 700 nm, more preferably light having the emission wavelength of 490 nm to 650 nm. Preferable emission colors of the emitting layer are, for instance, red, yellow and green.

Specific examples of the compound suitable for the phosphorescent host are a carbazole derivative, triazoles derivative, oxazole derivative, oxadiazole derivative, imidazoles derivative, polyarylalkane derivative, pyrazoline derivative, pyrazolone derivative, phenylenediamine derivative, arylamine derivative, amino-substituted chalcone derivative, styryl anthracene derivative, fluorenone derivative, hydrazone derivative, stilbene derivative, silazane derivative, aromatic tertiary amine compound, styrylamine compound, aromatic dimethylidene compound, porphyrin compound, anthraquinodimethane derivative, anthrone derivative, diphenylquinone derivative, thiopyrandioxide derivative, carbodiimide derivative, fluorenylidenemethan derivative, distyryl pyrazine derivative, hyterocyclic tetracarboxylic acid anhydride such as naphthaleneperylene, phthalocyanine derivative, various metal complex polysilane compounds typified by a metal complex of 8-quinolinol derivative, and a metal complex having metal phthalocyanine, benzoxazole or benzothiazole as the ligand, poly(N-vinylcarbazole) derivative, aniline copolymer, conductive high molecular weight oligomers such as thiophene oligomer and polythiophene, polymer compounds such as polythiophene derivative, polyphenylene derivative, polyphenylene vinylene derivative and polyfluorene derivative.

One of the phosphorescent host may be used alone, or two or more thereof may be used in combination. Specifically, the following compounds are shown.

[Formula 64]

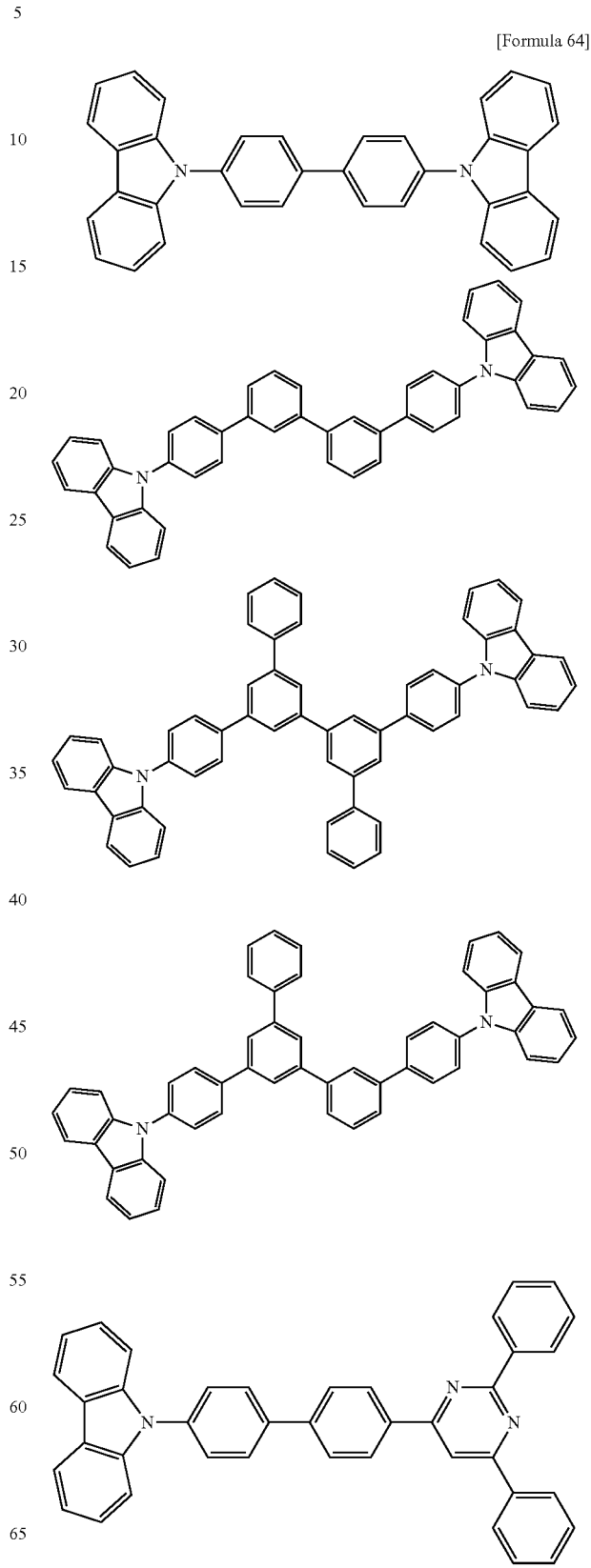

115
-continued

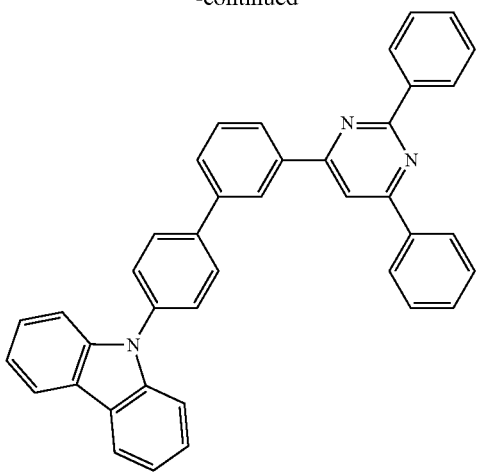

The organic EL device according to this exemplary embodiment may include an emitting layer containing a fluorescent material (i.e., a fluorescent-emitting layer). Known fluorescent materials are usable for the fluorescent-emitting layer. The fluorescent material is preferably at least one selected from an anthracene derivative, fluoranthene derivative, styrylamine derivative and arylamine derivative, among which the anthracene derivative and the arylamine derivative are more preferable. As the host material, the anthracene derivative is further preferable. As the dopant, the arylamine derivative is preferable. Specifically, preferable materials described in International Publication Nos. 2010/134350 and 2010/134352 are selected. The compound and the organic-EL-device material according to the exemplary embodiment may be used as the fluorescent material for the fluorescent-emitting layer and may be used as the host for the fluorescent-emitting layer.

The anthracene derivative as the fluorescent material preferably has 26 to 100 ring carbon atoms, more preferably 26 to 80 ring carbon atoms, further preferably 26 to 60 ring carbon atoms. More specifically, the anthracene derivative is preferably an anthracene derivative represented by a formula (10) below.

[Formula 65]

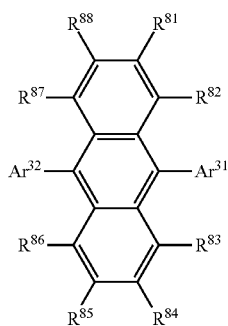

(10)

In the formula (10), $Ar^{31}$ and $Ar^{32}$ each independently represent a substituted or unsubstituted aryl group having 6 to 50 ring carbon atoms or a heterocyclic group having 5 to 50 ring atoms.

$R^{81}$ to $R^{88}$ each independently represent a hydrogen atom, a substituted or unsubstituted aryl group having 6 to 50 ring carbon atoms, a substituted or unsubstituted heterocyclic group having 5 to 50 ring atoms, a substituted or unsubstituted alkyl group having 1 to 50 carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted alkoxycarbonyl group having 2 to 50 carbon atoms, a substituted or unsubstituted silyl group, a carboxyl group, a halogen atom, a cyano group, a nitro group or a hydroxyl group.

The aryl group having 6 to 50 ring carbon atoms is preferably an aryl group having 6 to 40 ring carbon atoms, more preferably an aryl group having 6 to 30 ring carbon atoms.

The heterocyclic group having 5 to 50 ring atoms is preferably a heterocyclic group having 5 to 40 ring atoms, more preferably a heterocyclic group having 5 to 30 ring atoms.

The alkyl group having 1 to 50 carbon atoms is preferably an alkyl group having 1 to 30 carbon atoms, more preferably an alkyl group having 1 to 10 carbon atoms, further preferably an alkyl group having 1 to 5 carbon atoms.

The alkoxy group having 1 to 50 carbon atoms is preferably an alkoxy group having 1 to 30 carbon atoms, more preferably an alkoxy group having 1 to 10 carbon atoms, further preferably an alkoxy group having 1 to 5 carbon atoms.

The aralkyl group having 7 to 50 carbon atoms is preferably an aralkyl group having 7 to 30 carbon atoms, more preferably an aralkyl group having 7 to 20 carbon atoms.

The aryloxy group having 6 to 50 ring carbon atoms is preferably an aryloxy group having 6 to 40 ring carbon atoms, more preferably an aryloxy group having 6 to 30 ring carbon atoms.

The arylthio group having 6 to 50 ring carbon atoms is preferably an arylthio group having 6 to 40 ring carbon atoms, more preferably an arylthio group having 6 to 30 ring carbon atoms.

The alkoxycarbonyl group having 2 to 50 carbon atoms is preferably an alkoxycarbonyl group having 2 to 30 carbon atoms, more preferably an alkoxycarbonyl group having 2 to 10 carbon atoms, further preferably an alkoxycarbonyl group having 2 to 5 carbon atoms.

Examples of the halogen atom are a fluorine atom, a chlorine atom and a bromine atom.

$Ar^{31}$ and $Ar^{32}$ are preferably a substituted or unsubstituted aryl group having 6 to 50 ring carbon atoms.

The anthracene derivative represented by the formula (10) is preferably an anthracene derivative represented by a formula (10-1) below.

[Formula 66]

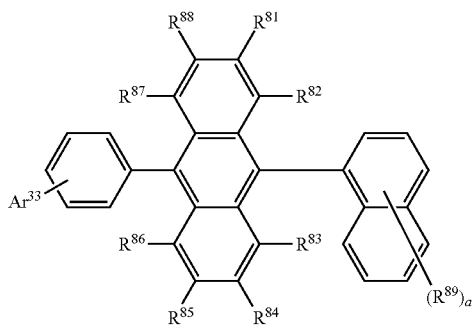

(10-1)

In the formula (10-1), Ar$^{33}$ represents a substituted or unsubstituted aryl group having 6 to 50 ring carbon atoms or a heterocyclic group having 5 to 50 ring atoms. R$^{81}$ to R$^{88}$ represent the same as defined above. R$^{89}$ represents the same as the definition of R$^{81}$ to R$^8$. a is an integer of 1 to 7.

Preferable examples of R$^{81}$ to R$^{88}$ are the same as the above examples thereof. Preferable examples of R$^{89}$ are the same as R$^{81}$ to R$^{88}$. a is preferably an integer of 1 to 3, more preferably 1 or 2.

The aryl group having 6 to 50 ring carbon atoms represented by Ar$^{33}$ is preferably an aryl group having 6 to 40 ring carbon atoms, more preferably an aryl group having 6 to 30 ring carbon atoms, further preferably an aryl group having 6 to 20 ring carbon atoms, more further preferably an aryl group having 6 to 12 ring carbon atoms.

The arylamine derivative as the fluorescent material is preferably an aryldiamine derivative, more preferably an aryldiamine derivative having a pyrene skeleton, further preferably an aryldiamine derivative having a pyrene skeleton and a dibenzofuran skeleton.

More specifically, the aryldiamine derivative is preferably an aryldiamine derivative represented by a formula (11) below.

[Formula 67]

(11)

In the above formula (11), Ar$^{34}$ to Ar$^{37}$ each independently represent a substituted or unsubstituted aryl group having 6 to 50 ring carbon atoms or a substituted or unsubstituted heteroaryl group having 5 to 50 ring atoms.

L$^{21}$ represents a substituted or unsubstituted arylene group having 6 to 50 ring carbon atoms or a substituted or unsubstituted heteroarylene group having 5 to 50 ring atoms.

The aryl group having 6 to 50 ring carbon atoms is preferably an aryl group having 6 to 30 ring carbon atoms, more preferably an aryl group having 6 to 20 ring carbon atoms, further preferably an aryl group having 6 to 12 ring carbon atoms, more further preferably a phenyl group and a naphthyl group.

The heteroaryl group having 5 to 50 ring atoms is preferably a heteroaryl group having 5 to 40 ring atoms, more preferably a heteroaryl group having 5 to 30 ring atoms, further preferably a heteroaryl group having 5 to 20 ring atoms. Examples of the heteroaryl group are a carbazolyl group, dibenzofuranyl group, and dibenzothiophenyl group, among which dibenzofuranyl group is preferable. A substituent for the heteroaryl group is preferably an aryl group having 6 to 30 ring carbon atoms (preferably having 6 to 20 ring carbon atoms, more preferably having 6 to 12 ring carbon atoms), among which a phenyl group and a naphthyl group are more preferable.

The arylene group having 6 to 50 ring carbon atoms is preferably an arylene group having 6 to 40 ring carbon atoms, more preferably an arylene group having 6 to 30 ring carbon atoms, further preferably an arylene group having 6 to 20 ring carbon atoms, more further preferably a pyrenyl group.

The thickness of the emitting layer is preferably in a range of 5 to 50 nm, more preferably in a range of 7 to 50 nm, further preferably in a range of 10 to 50 nm. When the thickness of the emitting layer is 5 nm or more, the emitting layer is easily formed. When the thickness of the emitting layer is 50 nm or less, increase in the drive voltage is avoidable.

Hole Transporting Layer

The hole transporting layer is an organic layer formed between the emitting layer and the anode and has a function to transport holes from the anode to the emitting layer. When the hole transporting layer is provided by a plurality of layers, an organic layer close to the anode is defined as the hole injecting layer. The hole injecting layer has a function to efficiently inject holes from the anode into the organic layer unit.

A material for forming the hole transporting layer is preferably an aromatic amine compound such as an aromatic amine derivative represented by a formula (H) below.

[Formula 68]

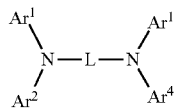

(H)

In the formula (H), Ar$^1$ to Ar$^4$ each represent a substituted or unsubstituted aromatic hydrocarbon group or fused aromatic hydrocarbon group having 6 to 50 ring carbon atoms, substituted or unsubstituted aromatic heterocyclic group or fused aromatic heterocyclic group having 5 to 50 ring atoms, or a group formed by combining the aromatic hydrocarbon group or the fused aromatic hydrocarbon group with the aromatic heterocyclic group or fused aromatic heterocyclic group.

In the formula (H), L represents a substituted or unsubstituted aromatic hydrocarbon group or fused aromatic hydrocarbon group having 6 to 50 ring carbon atoms, or a substituted or unsubstituted aromatic heterocyclic group or fused aromatic heterocyclic group having 5 to 50 ring atoms.

Specific examples of the compound of the formula (H) are shown below.

[Formula 69]
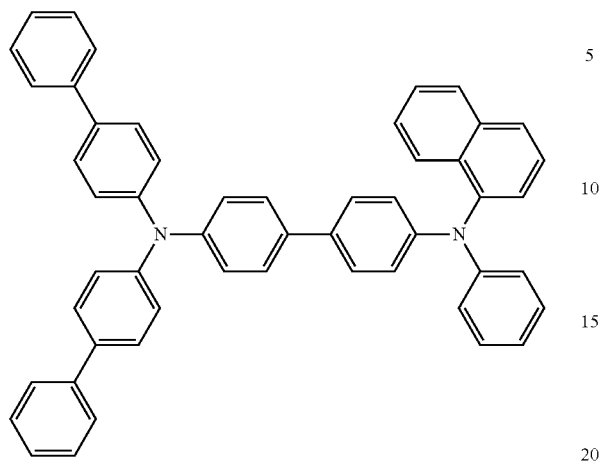
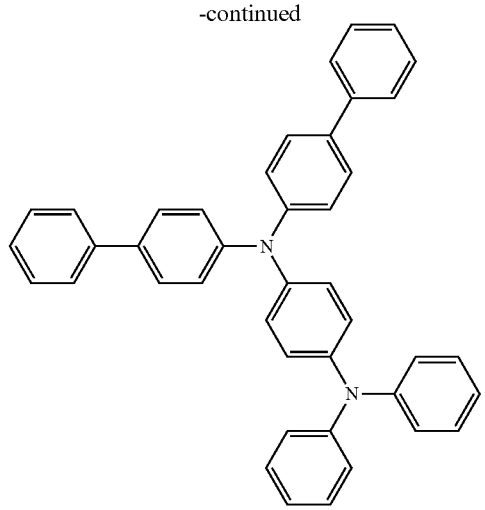
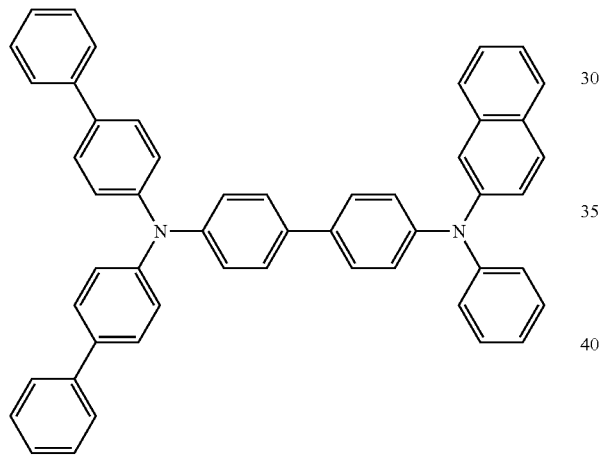
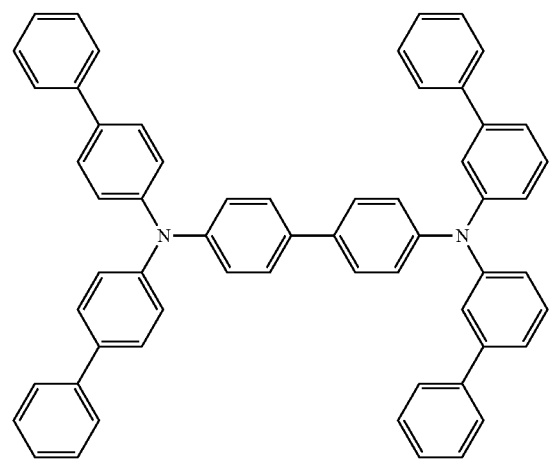
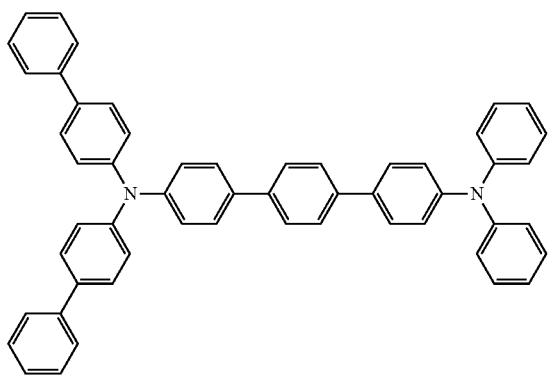
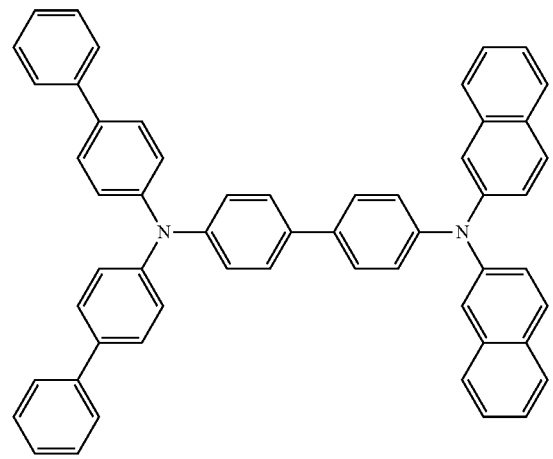

121
-continued
122
-continued
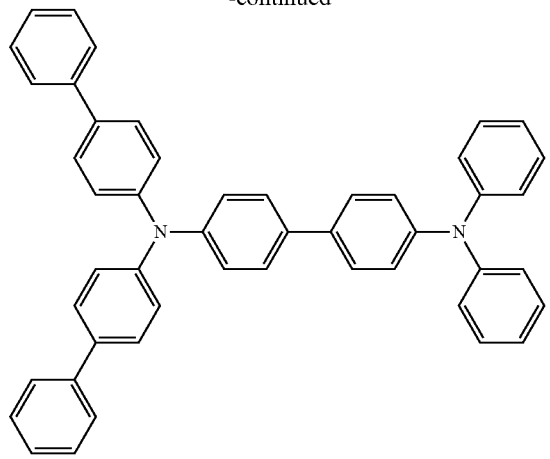
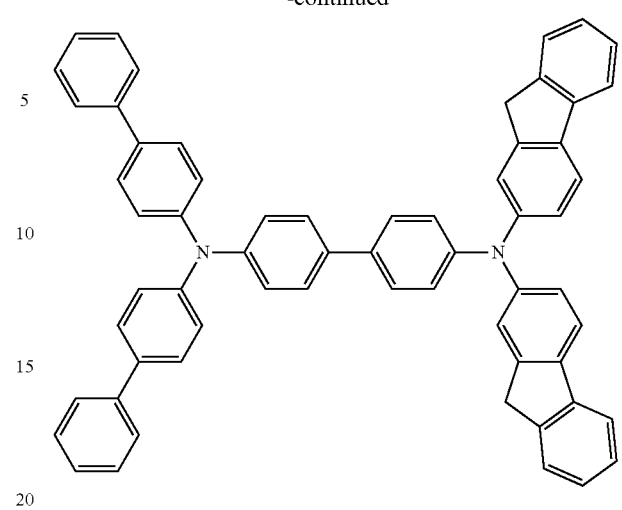
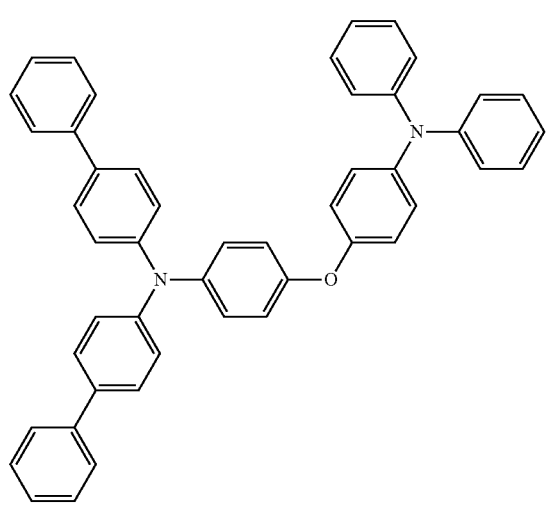
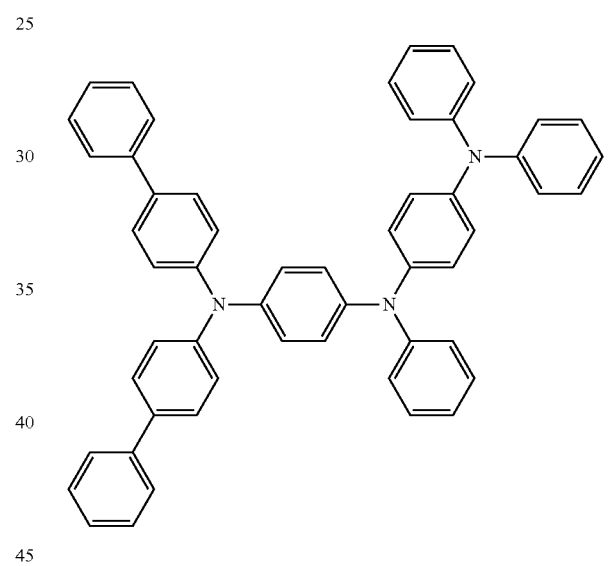
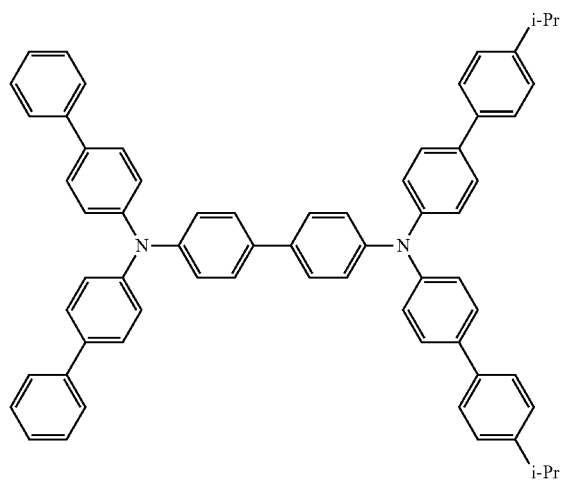
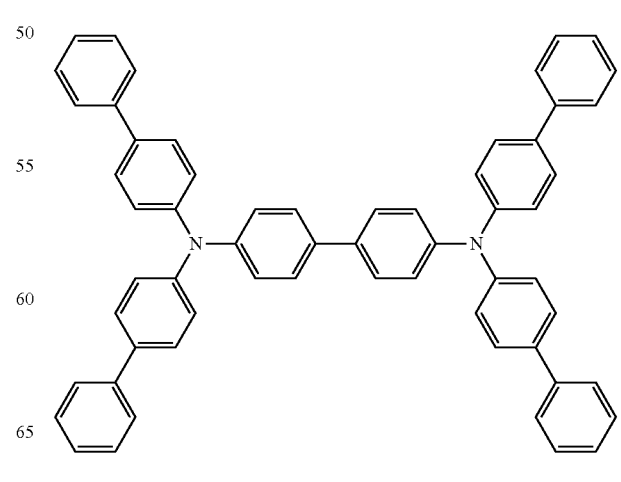

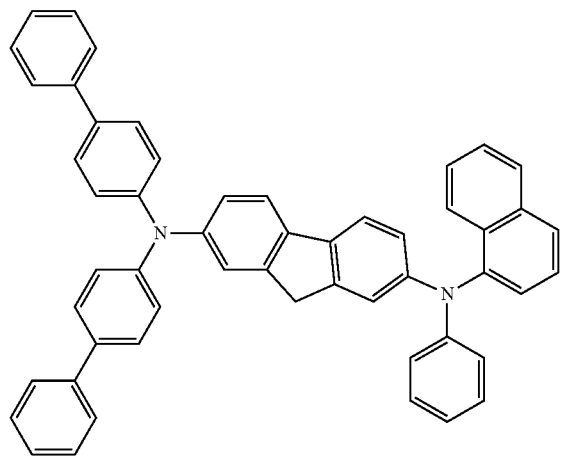
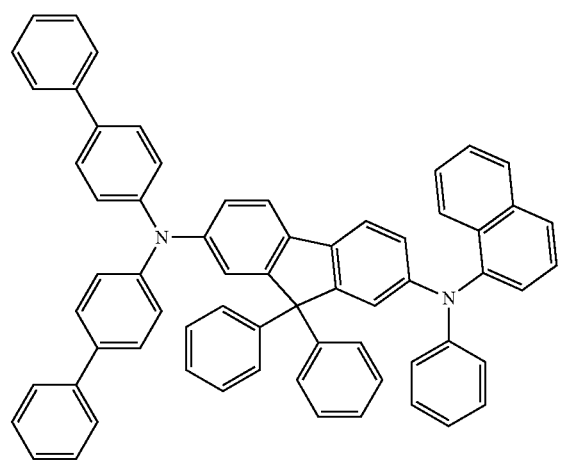
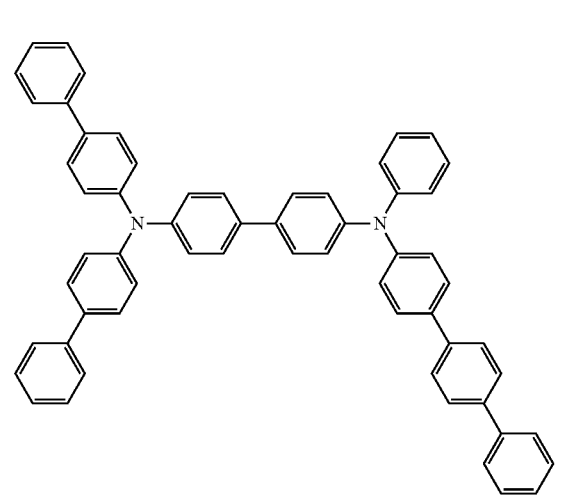
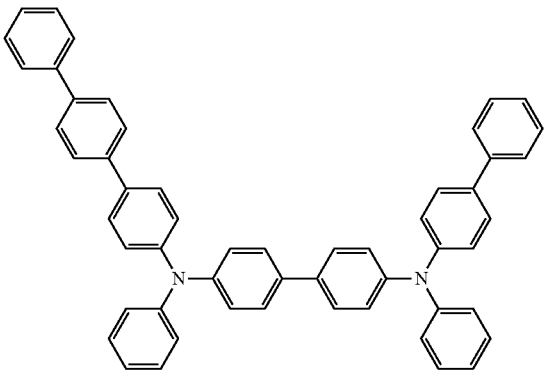
[Formula 70]
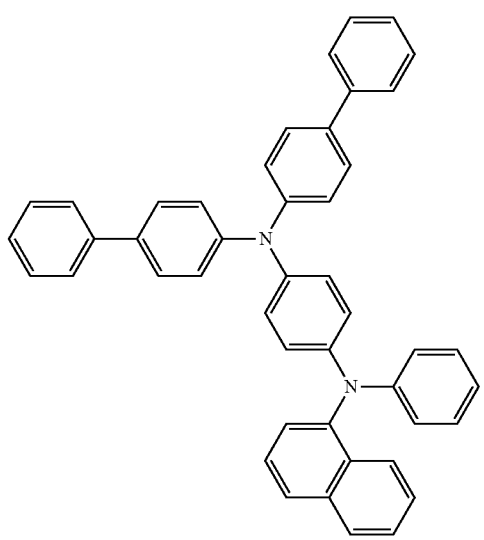
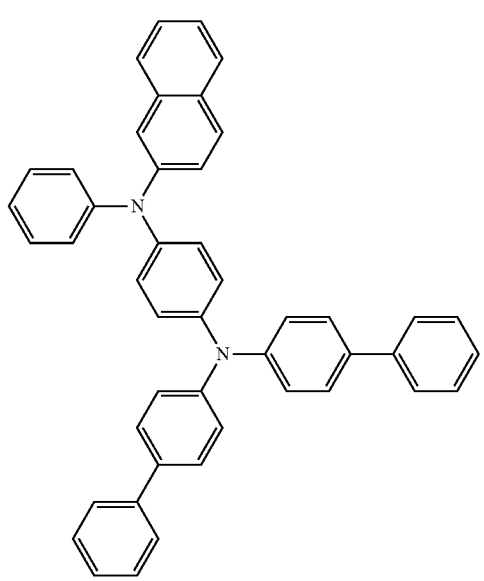

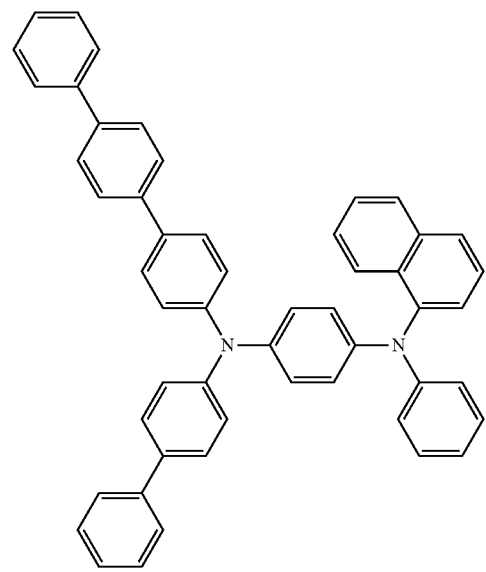
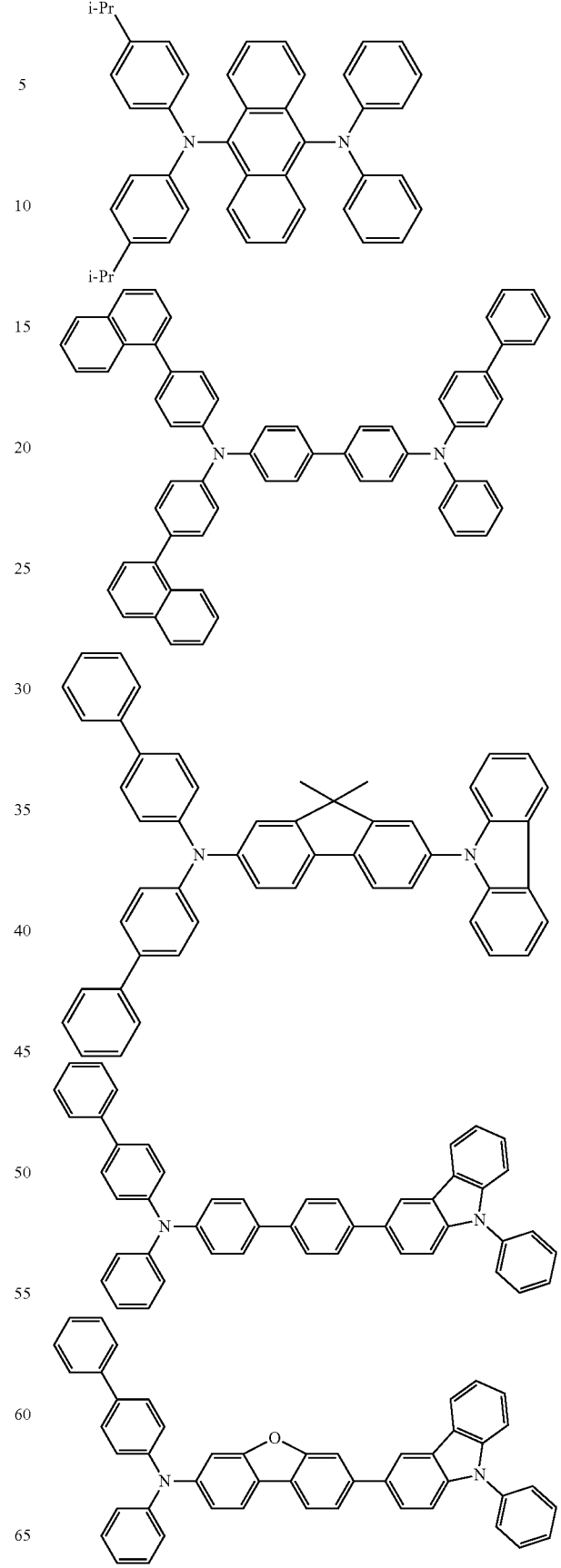

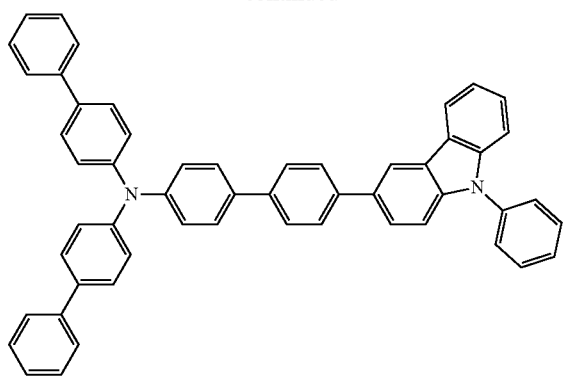
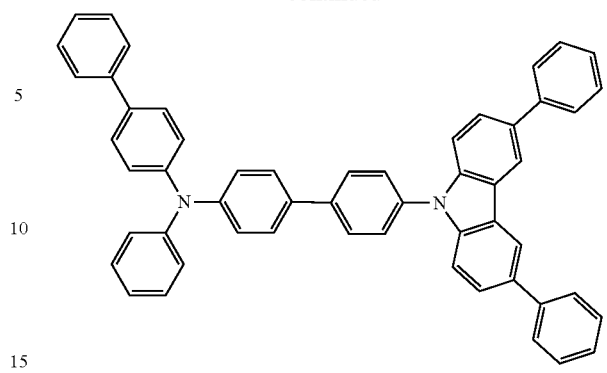
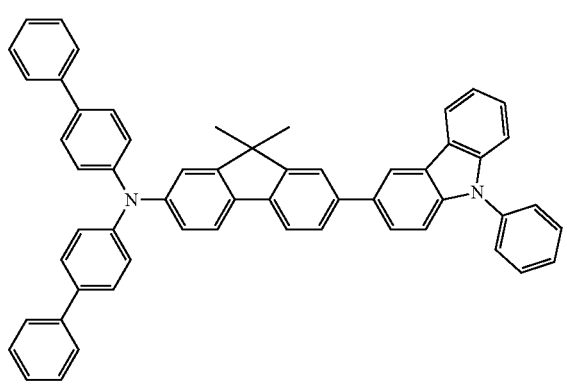
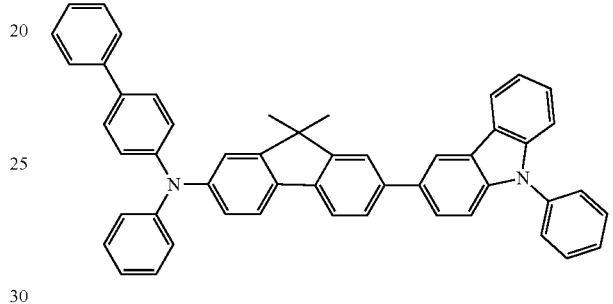

Aromatic amine represented by a formula (J) is also preferably usable for forming the hole transporting layer.

[Formula 71]

In the formula (J), the definition of $Ar^1$ to $Ar^3$ is the same as the definition of $Ar^1$ to $Ar^4$ in the formula (H). Examples of the compound represented by the formula (J) are shown below. However, the compound represented by the formula (J) is not limited thereto.

[Formula 72]

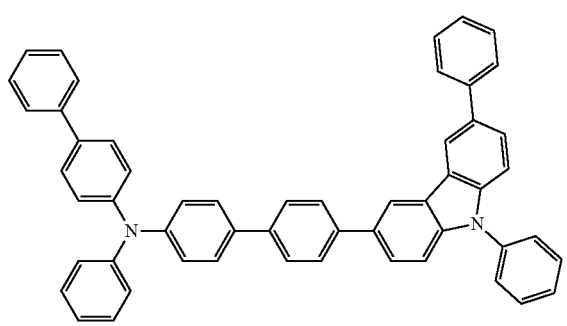
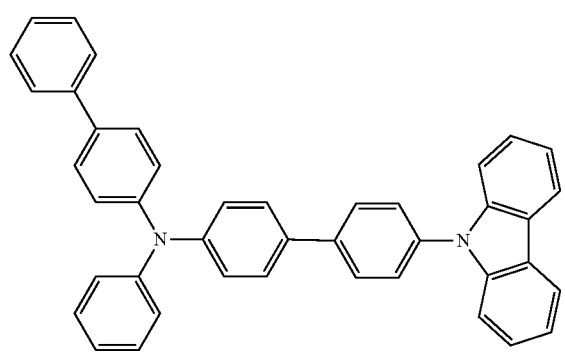
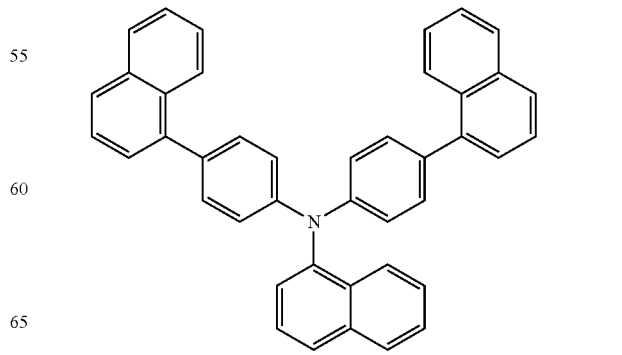

129
-continued
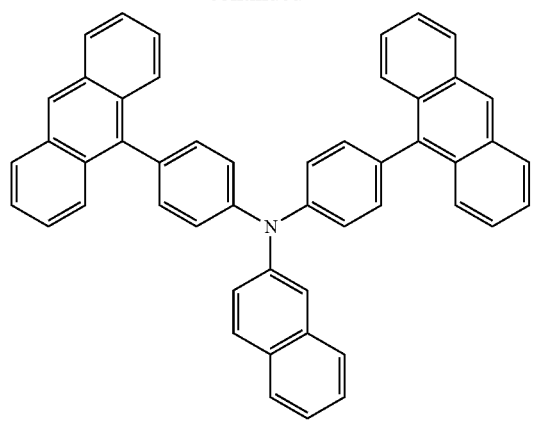
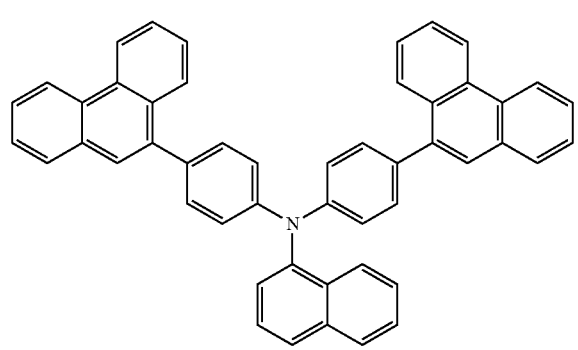
130
-continued
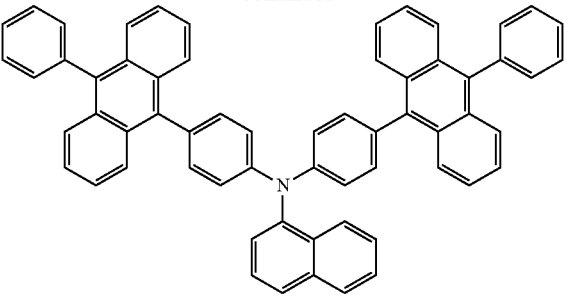
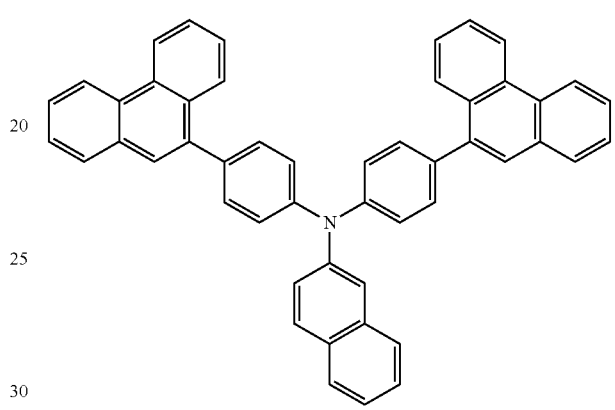
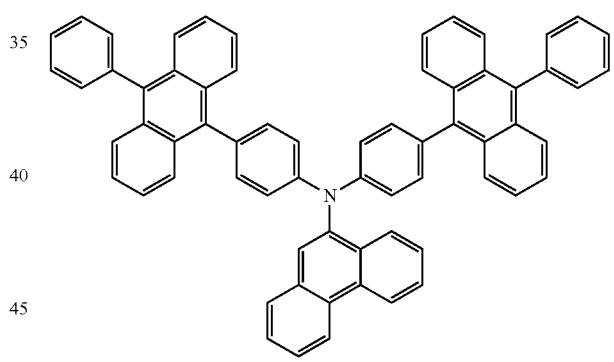
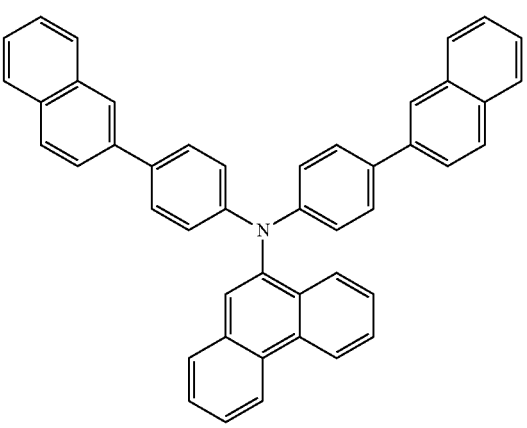

131
-continued
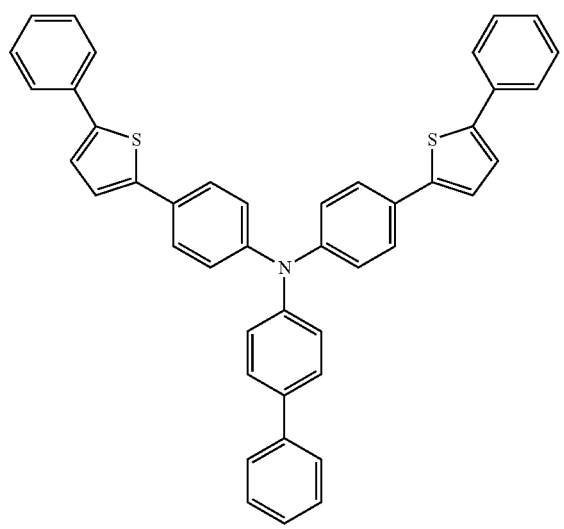
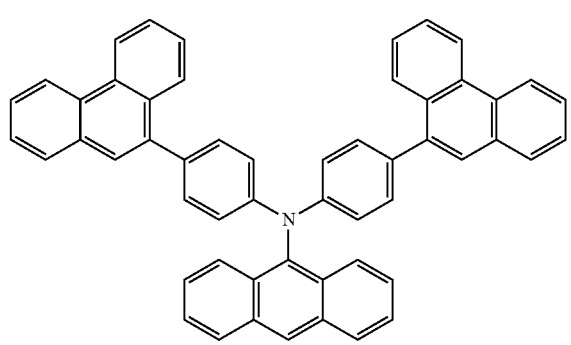
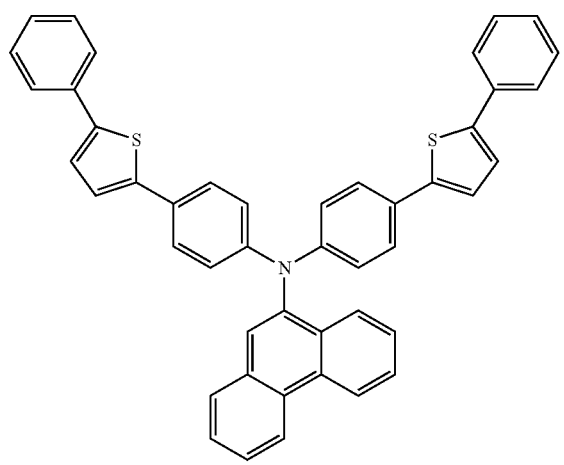
132
-continued
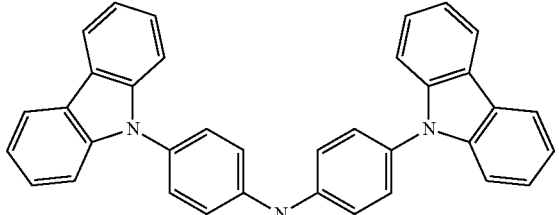
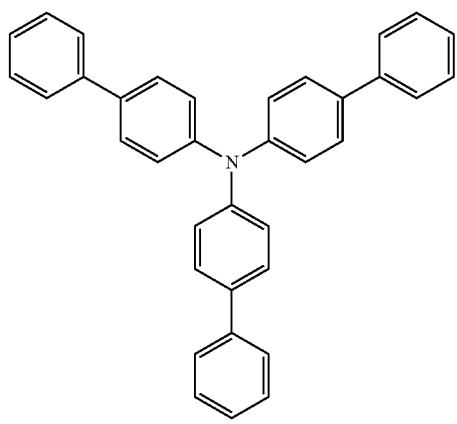
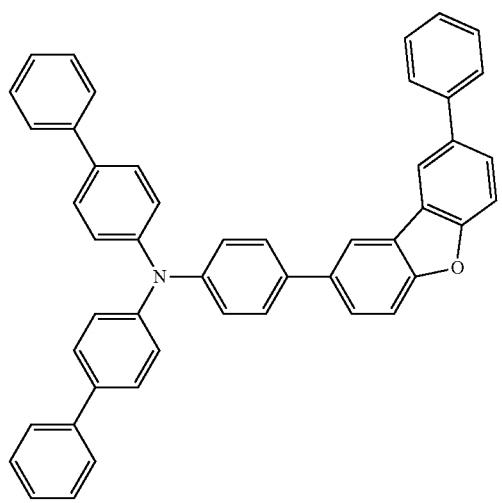

-continued

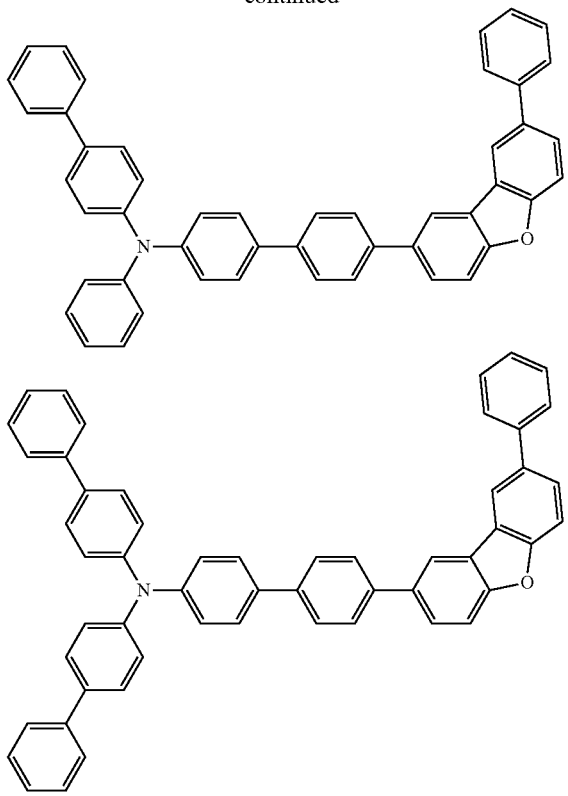

The hole transporting layer of the organic EL device according to the exemplary embodiment may have a double-layer structure of a first hole transporting layer (near the anode) and a second hole transporting layer (near the cathode).

Although a film thickness of the hole transporting layer is not particularly limited, the film thickness is preferably 10 nm to 200 nm.

In the organic EL device according to the exemplary embodiment, a layer containing an acceptor material may be bonded to a side near the anode of the hole transporting layer or the first hole transporting layer. With this arrangement, reduction in the drive voltage and manufacturing costs is expected.

The acceptor material is preferably a compound represented by the following formula (K).

[Formula 73]

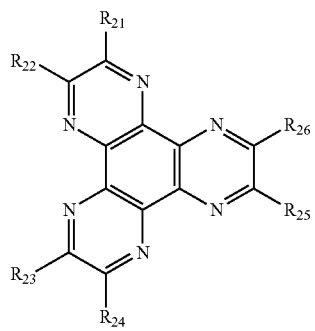

(K)

In the formula (K), $R_{21}$ to $R_{26}$ may be mutually the same or different and each independently represent a cyano group, —$CONH_2$, a carboxyl group or —$COOR_{27}$ in which $R_{27}$ represents an alkyl group having 1 to 20 carbon atoms or a cycloalkyl group having 3 to 20 carbon atoms. Among a pair of $R_{21}$ and $R_{22}$, a pair of $R_{23}$ and $R_{24}$ and a pair of $R_{25}$ and $R_{26}$, one or more of the pairs may be combined to form a group represented by —CO—O—CO—

Examples of $R_{27}$ include a methyl group, ethyl group, n-propyl group, isopropyl group, n-butyl group, isobutyl group, t-butyl group, cyclopentyl group and cyclohexyl group.

Although a film thickness of the acceptor material is not particularly limited, the film thickness is preferably 5 nm to 20 nm.

n/p Doping

In the aforementioned hole transporting layer and electron transporting zone, carrier injectability is adjustable by doping (n) of the donor material or doping (p) of the acceptor material as described in the specification of JP Patent No. 3695714.

n-doping is representatively exemplified by a method of doping a metal such as Li or Cs to an electron transporting material. p-doping is representatively exemplified by a method of doping an acceptor material such as $F_4TCNQ$(2,3,5,6-Tetrafluoro-7,7,8,8-tetracyanoquinodimethane) to a hole transporting material.

Space Layer

For instance, when a fluorescent-emitting layer is laminated to a phosphorescent-emitting layer, the space layer is provided between the fluorescent-emitting layer and the phosphorescent-emitting layer in order to prevent excitons generated in the phosphorescent-emitting layer from diffusing into the fluorescent-emitting layer or to adjust carrier balance. Moreover, the space layer may be provided between a plurality of phosphorescent-emitting layers.

Since the space layer is provided between the emitting layers, the space layer is preferably formed of a material having both of electron transporting capability and hole transporting capability. Moreover, triplet energy of the space layer is preferably 2.6 eV or more in order to prevent diffusion of triplet energy into an adjacent phosphorescent-emitting layer. The material used for the space layer is the same as the aforementioned material used for the hole transporting layer.

Blocking Layer

The organic EL device according to the exemplary embodiment preferably includes a blocking layer such as an electron blocking layer, hole blocking layer or triplet blocking layer at a part adjacent to the emitting layer. Herein, the electron blocking layer prevents electrons from leaking from the emitting layer into the hole transporting layer while the hole blocking layer prevents holes from leaking from the emitting layer into the electron transporting layer.

The triplet blocking layer has a function of preventing triplet excitons generated in the emitting layer from diffusing into neighboring layers to trap the triplet excitons within the emitting layer, thereby suppressing energy deactivation of the triplet excitons on molecules other than the emitting dopant in the electron transporting layer.

When the triplet blocking layer is provided in a phosphorescent device, triplet energy of a phosphorescent dopant in the emitting layer is denoted as $E^T_d$ and triplet energy of a compound used as the triplet blocking layer is denoted as $E^T_{TB}$. In an energy relationship of $E^T_d < E^T_{TB}$, triplet excitons of the phosphorescent dopant are trapped (cannot be transferred to another molecule) to leave no alternative route for energy deactivation other than emission on the dopant, so that highly efficient emission can be expected. However, when an energy gap ($\Delta E^T = E^T_{TB} - E^T_d$) is small even though the relationship of $E^T_d < E^T_{TB}$ is satisfied, under actual environments for driving a device (i.e., at around the room temperature), it is considered that triplet excitons can be transferred to another molecule irrespective of the energy gap $\Delta E^T$ by absorbing heat energy around the device. Particularly, since the excitons of the phosphorescent device has longer lifetime than those of a fluorescent device, influence by heat absorption during transfer of the excitons is more likely to be given on the phosphorescent device relative to the fluorescent device. The larger energy gap $\Delta E^T$ relative to heat energy at the room temperature is preferable, more preferably 0.1 eV or more, further preferable at 0.2 eV or more. On the other hand, in the fluorescent device, the aforementioned organic-EL-device material according to the exemplary embodiment is usable as the triplet blocking layer in the TTF device structure described in International Publication WO2010/134350A1.

An electron mobility of a material for forming the triplet blocking layer is desirably $10^{-6}$ cm$^2$/(V·s) or more in an electric field intensity of 0.04 MV/cm to 0.5 MV/cm. As a measuring method of the electron mobility of the organic material, some methods such as Time of Flight method are known. Herein, the electron mobility is determined by the impedance spectroscopy.

An electron mobility of a material for forming the triplet blocking layer is desirably $10^{-6}$ cm$^2$/(V·s) or more in an electric field intensity of 0.04 MV/cm to 0.5 MV/cm. As a measuring method of the electron mobility of the organic material, some methods such as Time of Flight method are known. Herein, the electron mobility is determined by the impedance spectroscopy.

An electron mobility of a material for forming the triplet blocking layer is desirably $10^{-6}$ cm$^2$/(V·s) or more in an electric field intensity of 0.04 MV/cm to 0.5 MV/cm. As a measuring method of the electron mobility of the organic material, some methods such as Time of Flight method are known. Herein, the electron mobility is determined by the impedance spectroscopy.

An electron mobility of a material for forming the triplet blocking layer is desirably $10^{-6}$ cm$^2$/(V·s) or more in an electric field intensity of 0.04 MV/cm to 0.5 MV/cm. As a measuring method of the electron mobility of the organic material, some methods such as Time of Flight method are known. Herein, the electron mobility is determined by the impedance spectroscopy.

Film Thickness

The thickness of each organic layer of the organic EL device in the exemplary embodiment is subject to no limitation except for the thickness particularly described above. However, the thickness is typically preferably in a range of several nanometers to 1 μm because an excessively thin film is likely to entail defects such as a pin hole while an excessively thick film requires high applied voltage and deteriorates efficiency.

Electronic Device

The organic EL device according to the exemplary embodiment is suitably applicable to an electronic device such as: a display component of an organic EL panel module and the like, a display device of a television, a mobile phone, a personal computer and the like; and an emitting unit of an illuminator or a vehicle light.

Modifications of Embodiment(s)

It should be noted that the invention is not limited to the above exemplary embodiments but may include any modification and improvement as long as such modification and improvement are compatible with the invention.

In the above exemplary embodiment of the invention, the compound represented by the formula (1) and the like is not only used for the electron injecting layer 8 of the organic EL device 1 but also usable for other organic layers. For instance, the compound according to the above exemplary embodiment is also preferably usable for the electron transporting layer 7. It is also preferable that the electron transporting layer 7 contains at least one of the electron-donating dopant and the organic metal complex in addition to the compound according to the above exemplary embodiment.

The specific arrangement and disposition for practicing the invention may be altered to other arrangements and treatments as long as such other arrangements and dispositions are compatible with the invention.

EXAMPLES

Examples of the invention will be described below. However, the invention is not limited by these Examples.

[1] Synthesis Example 1

Synthesis of Compound (1)

A synthesis scheme of a compound (1) is shown below.

[Formula 74]

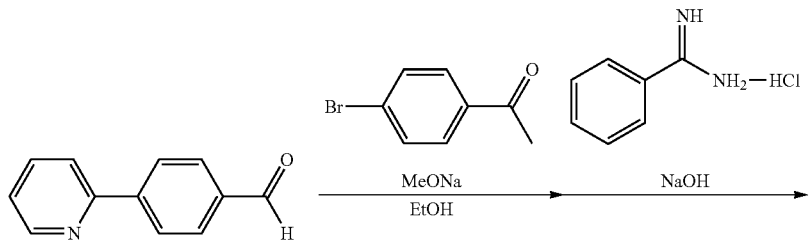

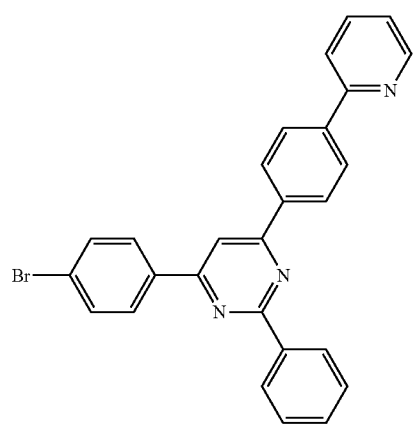 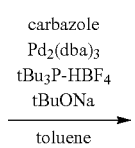 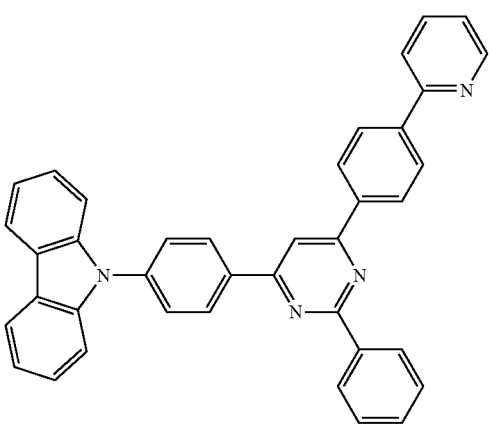

(A1) → (1)

[1-1] Synthesis of Intermediate (A1)

Under an argon gas atmosphere, ethanol (88 mL) was added to 4-(pyridine-2-yl)benzaldehyde (5.00 g, 27.3 mmol), 4-bromoacetophenone (5.43 g, 27.3 mmol), and sodium methoxide (147 mg, 0.273 mmol). The obtained solution was stirred at the room temperature for two hours and at the reflux temperature for three hours. Subsequently, benzamidine hydrochloride (4.40 g, 28.1 mmol) and sodium hydroxide (2.18 g, 54.6 mmol) were added to the reaction solution. The obtained solution was stirred at the reflux temperature for three hours. After the reaction was over, a deposit was separated by filtration. Then, the obtained solid was washed with water and methanol to obtain an intermediate (A1) (5.13 g, 11.0 mmol) (a yield of 40%).

[1-2] Synthesis of Compound (1)

Under an argon gas atmosphere, toluene (26 mL) was added to the intermediate (A1) (2.97 g, 6.40 mmol), carbazole (1.07 g, 6.40 mmol), tris(dibenzylidenacetone)dipalladium(0) (117 mg, 0.128 mmol), tetrafluoroborate of tert-butylphosphine (149 mg, 0.514 mmol), and sodium-tert-butoxide (861 mg, 8.96 mmol). The obtained solution was stirred at the reflux temperature for seven hours. After the reaction was over, the obtained mixture was separated by filtration and washed with water and methanol. The mixture was dissolved in toluene at the reflux temperature and was subjected to silica gel short column chromatography. The solution was heated to the reflux temperature of toluene. After methanol was added to the solution at 100 degrees C., the deposited solid was separated by filtration and dried to obtain a compound (1) (2.34 g, 4.25 mmol) (a yield of 66%). As a result of mass analysis, this compound was a target object and m/e was equal to 550 while a calculated molecular weight was 550.65.

[2] Synthesis Example 2

Synthesis of Compound (2)

A synthesis scheme of a compound (2) is shown below.

[Formula 75]

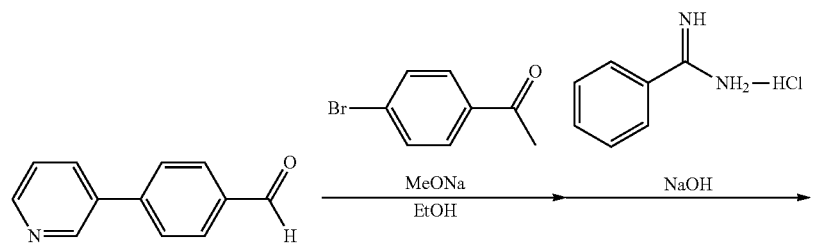

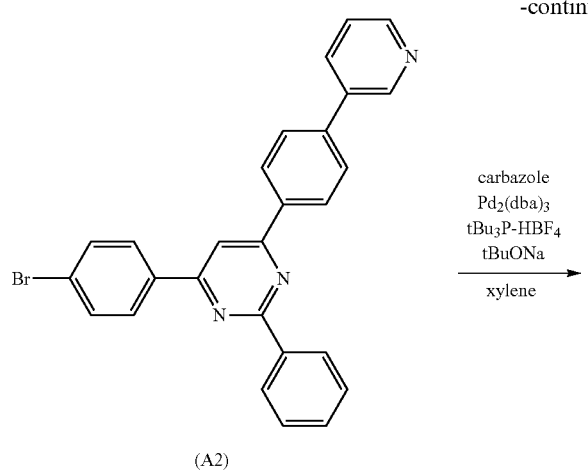

(A2)

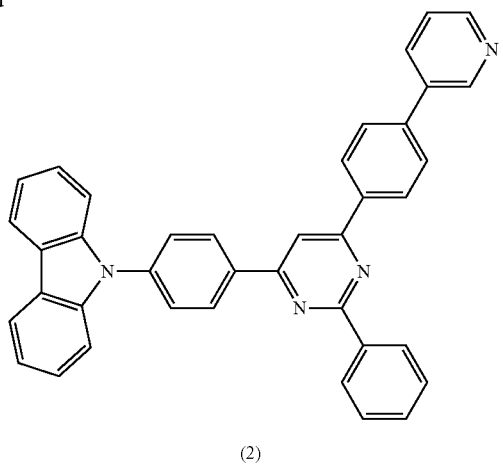

(2)

A compound (2) was obtained through an intermediate (A2) in the same manner as in the synthesis of the compound (1) except for using 4-(pyridine-3-yl)benzaldehyde in place of 4-(pyridine-2-yl)benzaldehyde. As a result of mass analysis, this compound was a target object and m/e was equal to 550 while a calculated molecular weight was 550.65.

[3] Synthesis Example 3

Synthesis of Compound (3)

A synthesis scheme of a compound (3) is shown below.

A compound (3) was obtained through an intermediate (A3) in the same manner as in the synthesis of the compound (1) except for using 4-(pyridine-4-yl)benzaldehyde in place of 4-(pyridine-2-yl)benzaldehyde. As a result of mass analysis, this compound was a target object and m/e was equal to 550 while a calculated molecular weight was 550.65.

[4] Synthesis Example 4

Synthesis of Compound (4)

A synthesis scheme of a compound (4) is shown below.

[Formula 76]

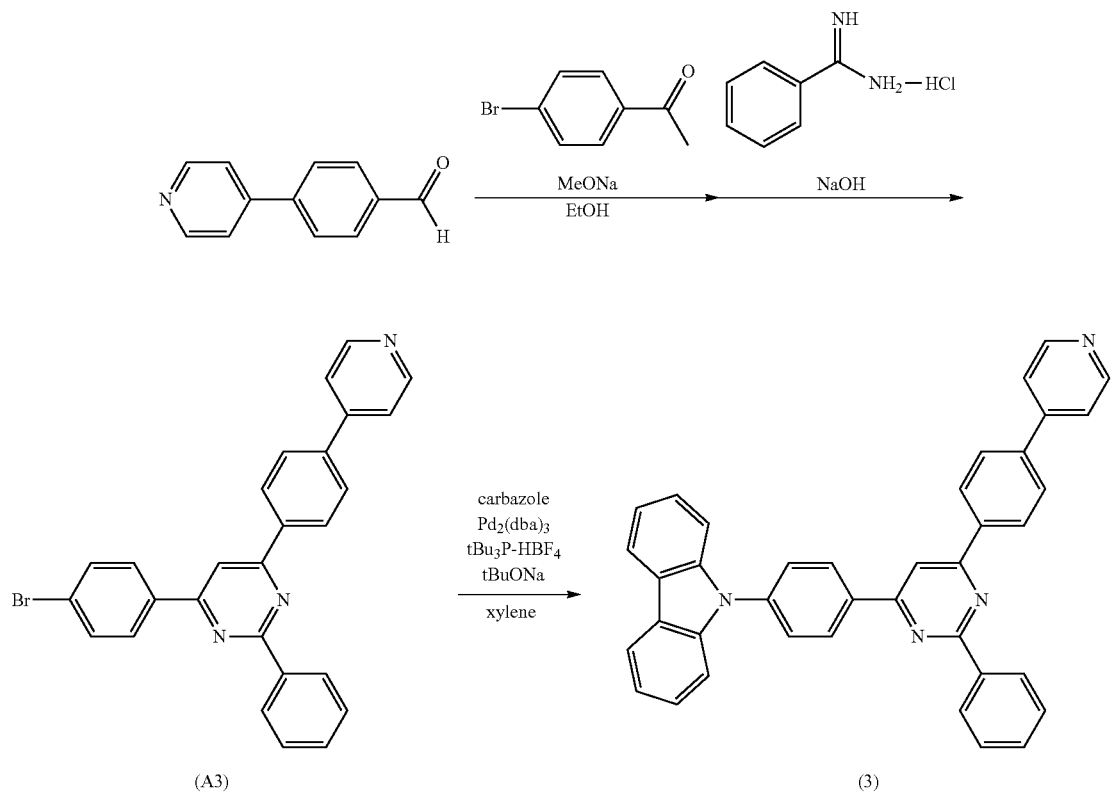

[Formula 77]

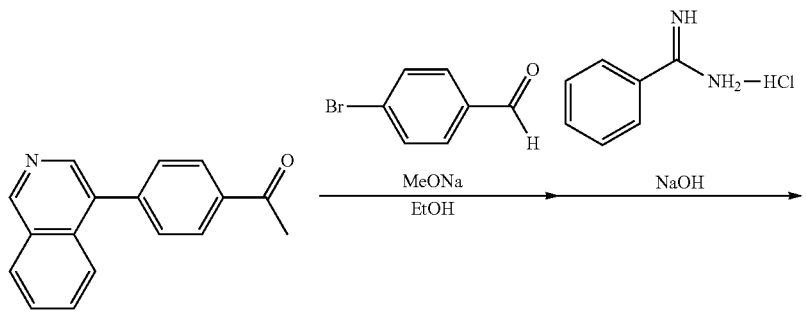

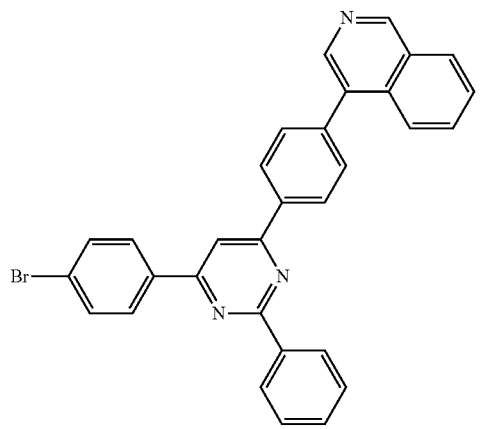

[Formula 78]

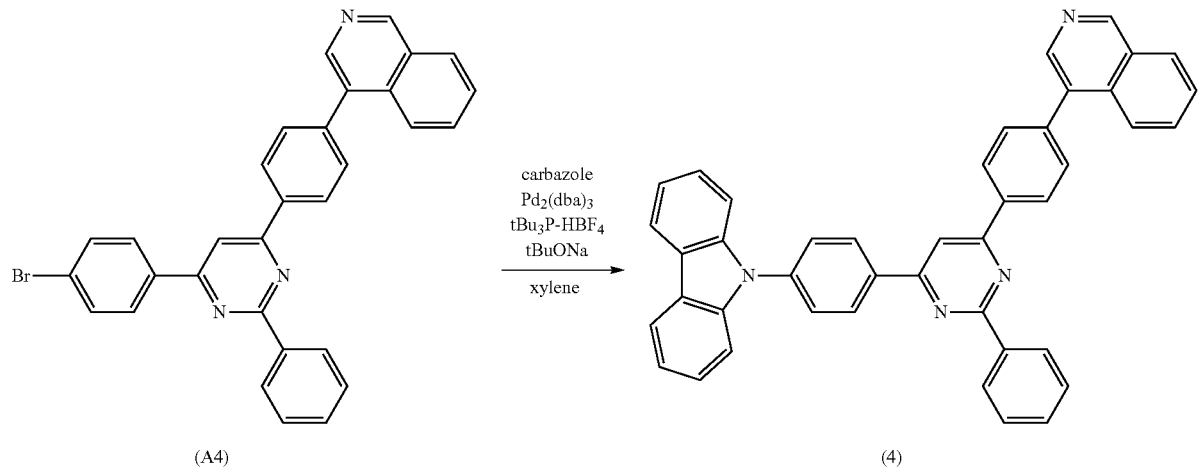

A compound (4) was obtained through an intermediate (A4) in the same manner as in the synthesis of the compound (1) except for using 4-bromobenzaldehyde in place of 4-(pyridine-2-yl)benzaldehyde and using 4-(isoquinoline-4-yl)acetophenone in place of 4-bromoacetophenone. As a result of mass analysis, this compound was a target object and m/e was equal to 600 while a calculated molecular weight was 600.73.

[5] Synthesis Example 5

Synthesis of Compound (5)

A synthesis scheme of a compound (5) is shown below.

[Formula 79]

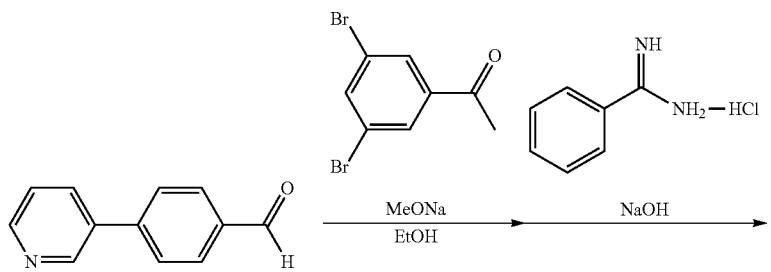

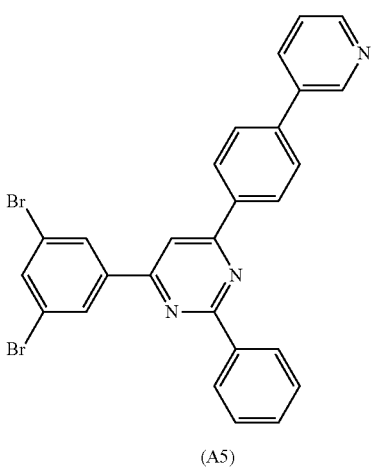

(A5)

[Formula 80]

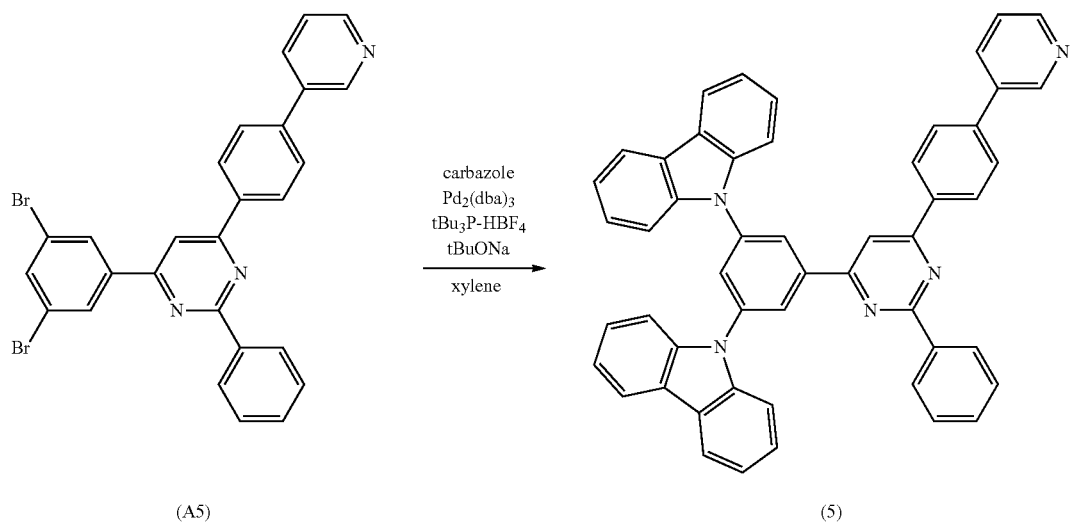

A compound (5) was obtained through an intermediate (A5) in the same manner as in the synthesis of the compound (2) except for using 3,5-dibromoacetophenone in place of 4-bromoacetophenone. As a result of mass analysis, this compound was a target object and m/e was equal to 715 while a calculated molecular weight was 715.86.

Manufacturing Example of Organic EL Device

Compounds used for manufacturing the organic EL device are shown below.

[Formula 81]

(HI-1)

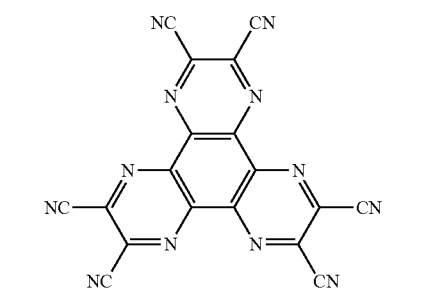

(HT-1)

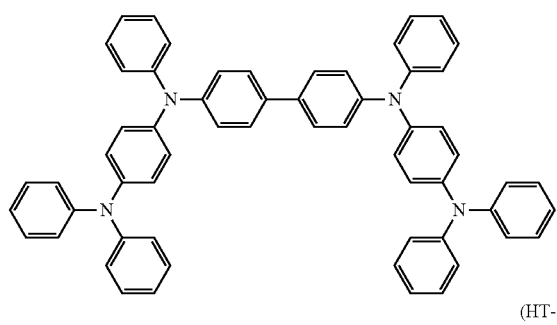

(HT-2)

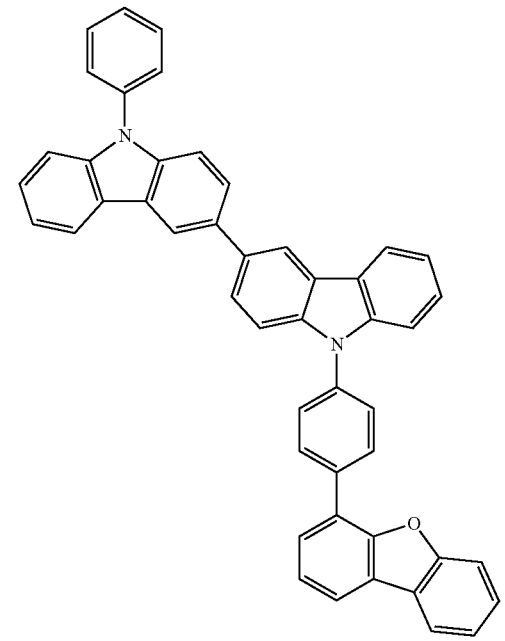

(BH-1)

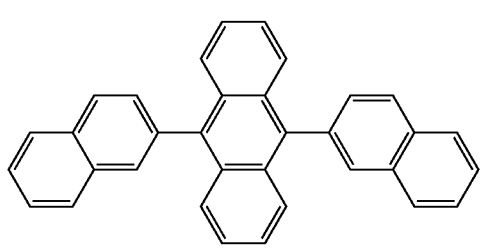

(BD-1)

(HB-1)

(E-1)

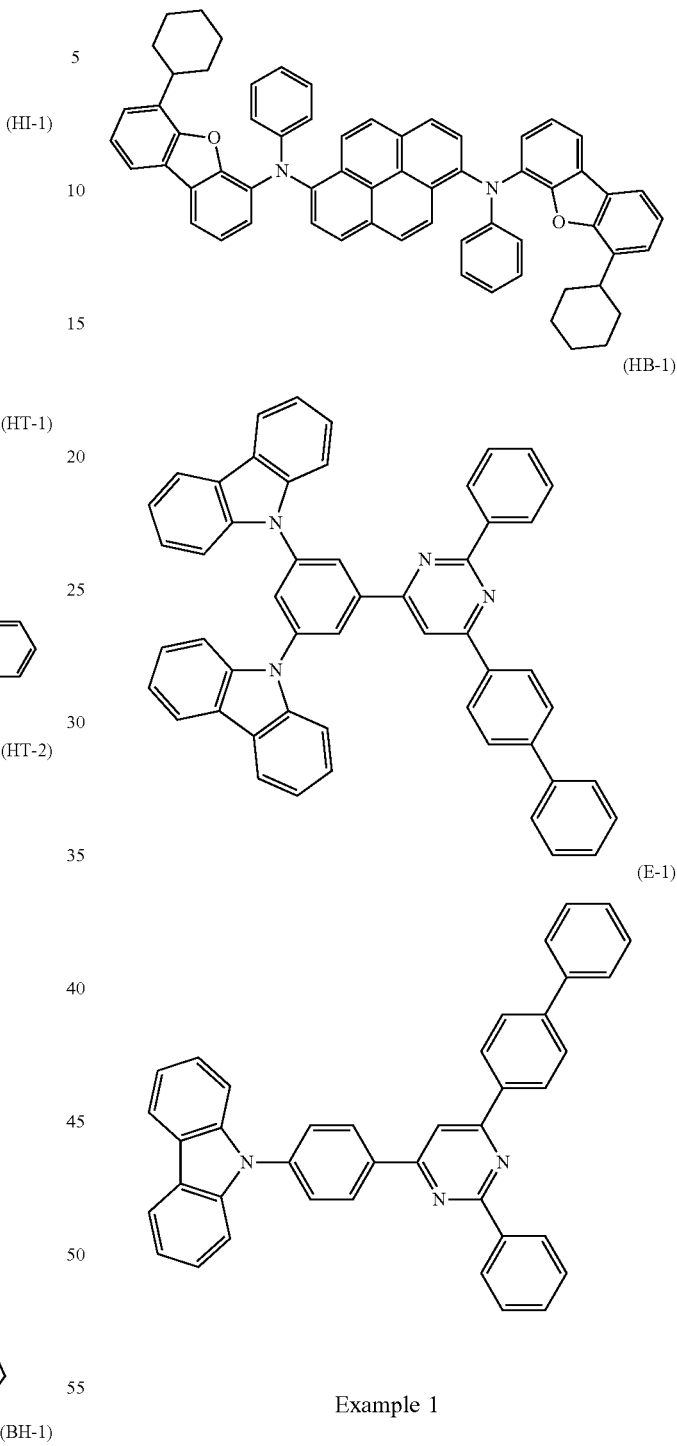

Example 1

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. After the glass substrate having the transparent electrode line was cleaned, the glass substrate was mounted on a substrate holder of a vacuum evaporation apparatus. Initially, a compound (HI-1) was deposited on a surface of the glass substrate where the transparent electrode line was provided in a manner to cover the transparent electrode, thereby forming a 10-nm thick HI-1 film of the compound HI-1 to prepare a hole injecting layer.

Next, on the hole injecting layer, the compound (HT-1) was deposited as a first hole transporting material to form a 80-nm thick HT-1 film to prepare a first hole transporting layer.

Next, on the first hole transporting layer, the compound (HT-2) was deposited to form a 10-nm thick HT-2 film to prepare a second hole transporting layer.

Further, the compound (BH-1) (host material) and the compound (BD-1) (dopant material) (weight ratio of BH-1 to BD-1 was 24:1) were co-deposited on the HT-2 film to form an emitting layer of 25 nm thickness.

The compound (HB-1) was deposited on the emitting layer to form a 25-nm thick HB-1 film to prepare a hole blocking layer and an electron transporting layer.

Further, the compound (1) synthesized in Synthesis Example 1 was deposited to form a 10-nm-thick electron injecting layer.

Subsequently, LiF was deposited to form a 1-nm thick film. Metal Al was deposited on the LiF film to form a 150-nm thick metal cathode, thereby providing the organic electroluminescence device.

Examples 2 to 3 and Comparative 1

The organic EL devices in Examples 2 to 3 and Comparative 1 were manufactured in the same manner as that in Example 1 except for using compounds shown in Table 1 in place of the compound (1).

Evaluation of Organic EL Devices

The organic EL devices manufactured in Examples 1 to 3 and Comparative 1 were evaluated as follows. The evaluation results are shown in Table 1.

Drive Voltage

Voltage was applied between the anode (ITO transparent electrode) and the metal cathode (metal Al) such that a current density was 10 mA/cm$^2$, where the voltage (unit: V) was measured.

External Quantum Efficiency EQE

Voltage was applied on each of the organic EL devices such that the current density was 10 mA/cm$^2$, where spectral radiance spectrum was measured by a spectroradiometer (CS-1000 manufactured by Konica Minolta, Inc.). The external quantum efficiency (unit: %) was calculated based on the obtained spectral-radiance spectra, assuming that the spectra was provided under a Lambertian radiation.

TABLE 1

| | Electron Injecting Layer | Voltage (V) (at 10 mA/cm$^2$) | External Quantum Efficiency (%) | Emission Color |
|---|---|---|---|---|
| Example 1 | Compound (1) | 5.1 | 9.2 | blue |
| Example 2 | Compound (2) | 4.0 | 11 | blue |
| Example 3 | Compound (3) | 4.8 | 9.9 | blue |
| Comparative 1 | Compound (E-1) | 8.3 | 4.4 | blue |

Table 1 shows that the lower voltage and higher efficiency of the organic EL device are achievable by using the compound of the exemplary embodiment of the invention. In comparison with the compound (E-1) used in Comparative 1, the organic EL devices of Examples 1 to 3 using the compound having the nitrogen-containing heterocyclic at a terminal end are found to be activated at a lower voltage with a higher efficiency.

This is because the electron injecting performance of the compounds (1) to (3) (i.e., the compound according to the exemplary embodiment of the invention) is improved by the nitrogen-containing heterocyclic group represented by Az at the terminal end in the formula (1). Thus, it is recognized that the performance of the compound E-1 of Comparative 1 as the electron transporting material is significantly improvable only by substituting the phenyl group at the terminal end of the compound E-1 with the nitrogen-containing heterocyclic group. In other words, it is recognized that the use of the compounds (1) to (3) improves the performance of the organic EL device in terms of the drive voltage and the luminous efficiency in comparison with the use of the compound (E-1).

Example 4

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. After the glass substrate having the transparent electrode line was cleaned, the glass substrate was mounted on a substrate holder of a vacuum evaporation apparatus. Initially, the compound (HI-1) was deposited on a surface of the glass substrate where the transparent electrode line was provided in a manner to cover the transparent electrode, thereby forming a 5-nm thick HI-1 film of the compound HI-1 to prepare a hole injecting layer.

Next, on the hole injecting layer, the compound (HT-1) was deposited as the first hole transporting material to form a 80-nm thick HT-1 film to prepare the first hole transporting layer.

Next, on the first hole transporting layer, the compound (HT-2) was deposited to form a 10-nm thick HT-2 film to prepare the second hole transporting layer.

Further, the compound (BH-2) (host material) and the compound (BD-2) (dopant material) (weight ratio of BH-2 to BD-2 was 24:1) were co-deposited on the HT-2 film to form an emitting layer of 25 nm thickness.

The compound (4) synthesized in Synthesis Example 4 was deposited on the emitting layer to form a 25-nm thick compound (4) film to prepare the electron transporting layer.

Subsequently, LiF was deposited to form a 1-nm thick film. Metal Al was deposited on the LiF film to form an 80-nm thick metal cathode, thereby providing the organic electroluminescence device.

Example 5

An organic EL device of Example 5 was prepared in the same manner as the organic EL device of Example 4 except for using the compound (5) synthesized in Synthesis Example 5 in place of the compound (4) in Example 4.

Comparative 2

An organic EL device of Comparative 2 was prepared in the same manner as the organic EL device of Example 4 except for using a compound (E-2) below in place of the compound (4) in Example 4.

[Formula 82]

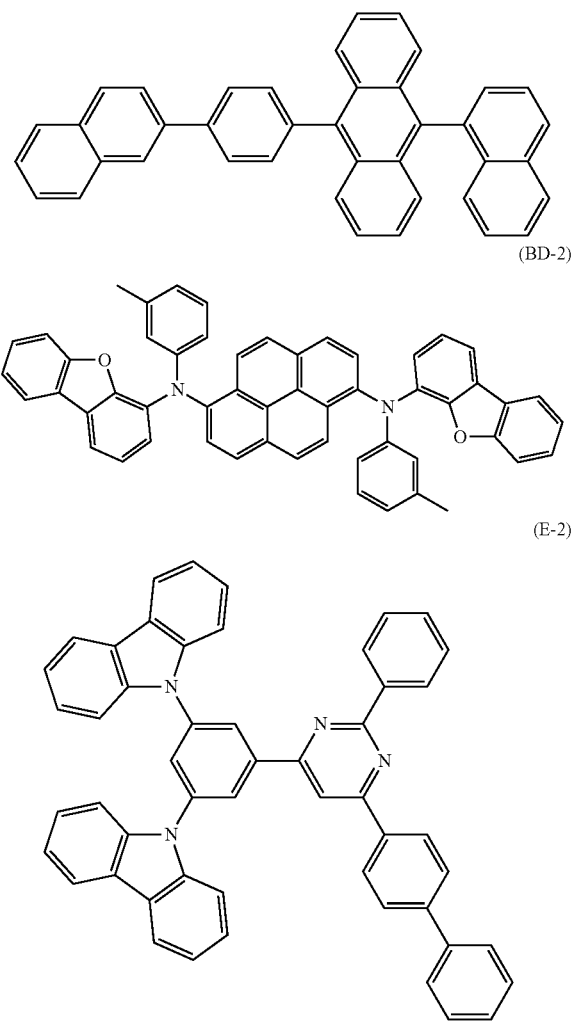

The manufactured organic EL devices of Examples 4, 5 and Comparative 2 were measured and evaluated in terms of the drive voltage and the external quantum efficiency in the same manner as described above. The results are shown in Table 2.

TABLE 2

|  | Electron Transporting Layer | Voltage (V) (at 10 mA/cm$^2$) | External Quantum Efficiency (%) |
|---|---|---|---|
| Example 4 | Compound (4) | 4.3 | 7.9 |
| Example 5 | Compound (5) | 4.7 | 7.7 |
| Comparative 2 | Compound (E-2) | 7.3 | 5.3 |

Table 2 shows that the lower voltage and higher efficiency of the organic EL device are achievable by using the compound of the exemplary embodiment of the invention. In comparison with the compound (E-2) used in Comparative 2, the organic EL devices of Examples 4 to 5 using the compound having the nitrogen-containing heterocyclic at a terminal end are found to be activated at a lower voltage with a higher efficiency. In other words, it is recognized that the use of the compound (4) or (5) improves the performance of the organic EL device in terms of the drive voltage and the luminous efficiency in comparison with the use of the compound (E-2).

Example 6

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. After the glass substrate having the transparent electrode line was cleaned, the glass substrate was mounted on a substrate holder of a vacuum evaporation apparatus. Initially, the compound HI-1 was deposited on a surface of the glass substrate where the transparent electrode line was provided in a manner to cover the transparent electrode, thereby forming a 5-nm thick HI-1 film of the compound HI-1 to prepare the hole injecting layer.

Next, on the hole injecting layer, the compound HT-1 was deposited as the first hole transporting material to form a 80-nm thick HT-1 film to prepare the first hole transporting layer.

Next, on the first hole transporting layer, the compound HT-2 was deposited to form a 10-nm thick HT-2 film to prepare a fourth hole transporting layer.

Further, the host (BH-2) and the dopant (BD-2) (mass ratio of BH-2 to BD-2 was 24:1) were co-deposited on the HT-2 film to form the emitting layer of 25 nm thickness.

Subsequent to the formation of the emitting layer, the compound (2) synthesized in Synthesis Example 2 and 8-quinolinato lithium (Liq) (mass ratio of the compound (2) to Liq was 50:50) were co-deposited on the emitting layer to form a 25-m thick electron transporting layer. Metal (Al) was deposited on the electron transporting layer to form an 80-nm thick metal cathode, thereby providing an organic electroluminescence device.

Comparative 3

An organic EL device of Comparative 3 was prepared in the same manner as the organic EL device of Example 6 except for using a compound (E-3) below in place of the compound (2) in Example 6.

[Formula 83]

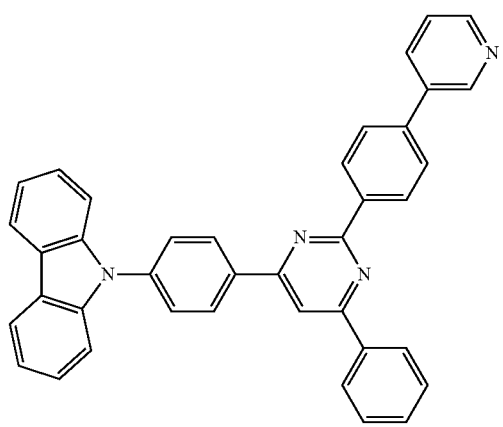

The manufactured organic EL devices of Example 6 and Comparative 3 were measured in terms of the drive voltage in the same manner as described above and in terms of a lifetime LT90 by the following method. The measured drive voltage and the lifetime LT90 were evaluated. The results are shown in Table 3.

TABLE 3

|  | Electron Transporting Layer | Voltage (V) (at 10 mA/cm²) | LT90 (hr) |
|---|---|---|---|
| Example 6 | Compound (2) | 3.9 | 365 |
| Comparative 3 | Compound (E-3) | 4.0 | 285 |

Table 3 shows that the longer lifetime of the organic EL device is achievable by using the compound of the exemplary embodiment of the invention. In comparison with the compound (E-3) used in Comparative 3, the organic EL device of Example 6 using the compound (2) having the nitrogen-containing heterocyclic chain at a carbon atom (carbon atom at a position 4) except for a carbon atom (carbon atom at a position 2) between two nitrogen atoms of pyrimidine is found to be activated for a longer period of time. In other words, it is recognized that the use of the compound (2) improves the performance of the organic EL device in terms of the lifetime in comparison with the use of the compound (E-3).

The invention claimed is:
1. A compound represented by a formula (1) below,

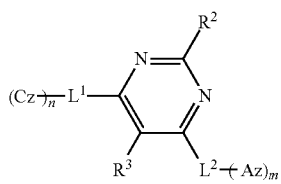

(1)

where: $R^3$ each independently represents a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, a substituted or unsubstituted arylthio group having 6 to 30 ring carbon atoms, a substituted or unsubstituted aromatic hydrocarbon group having 6 to 30 ring carbon atoms, or a substituted or unsubstituted heterocyclic group having 5 to 30 ring atoms;

$R^2$ is a substituted or unsubstituted aromatic hydrocarbon group having 6 to 30 ring carbon atoms;

when $R^2$ has a substituent, the substituent is a halogen atom, a hydroxyl group, a cyano group, a nitro group, a carboxy group, an unsubstituted alkyl group having 1 to 30 carbon atoms, an unsubstituted alkenyl group having 2 to 30 carbon atoms, an unsubstituted alkynyl group having 2 to 30 carbon atoms, an unsubstituted alkylsilyl group having 3 to 30 carbon atoms, an unsubstituted arylsilyl group having 6 to 60 ring carbon atoms, an unsubstituted alkoxy group having 1 to 30 carbon atoms, an unsubstituted aryloxy group having 6 to 30 ring carbon atoms, an unsubstituted arylthio group having 6 to 30 ring carbon atoms, an unsubstituted oxygen-containing heterocyclic group having 5 to 30 ring carbon atoms, an unsubstituted sulfur-containing heterocyclic group having 5 to 30 ring carbon atoms, or an unsubstituted aromatic hydrocarbon group having 6 to 30 ring carbon atoms;

when the aryloxy group and the arylthio group respectively have substituents, adjacent ones of the substituents are bonded to form a ring or are not bonded;

$L^1$ is a single bond or a linking group and the linking group in $L^1$ is an alkenylene group, an alkynylene group, a substituted or unsubstituted aromatic hydrocarbon group having 6 to 30 ring carbon atoms, a substituted or unsubstituted heterocyclic group having 5 to 30 ring atoms, a multiple linking group provided by bonding two to four groups selected from the above aromatic hydrocarbon group, a multiple linking group provided by bonding two to four groups selected from the above heterocyclic group, or a multiple linking group provided by bonding two to four groups selected from the above aromatic hydrocarbon group and the above heterocyclic group;

the above aromatic hydrocarbon group and the heterocyclic group forming the multiple linking group are mutually the same or different and adjacent ones thereof are bonded to further form a ring or are not bonded;

$L^2$ is a linking group and the linking group represents the same as the linking group in $L^1$ with the proviso that the heterocyclic group is selected from the group consisting of a pyridyl group, pyrimidinyl group, pyrazinyl group, pyridazynyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, imidazolyl group, pyrazolyl group, triazolyl group, tetrazolyl group, indolyl group, benzimidazolyl group, indazolyl group, imidazopyridinyl group, benzotriazolyl group, furyl group, thienyl group, oxazolyl group, thiazolyl group, isoxazolyl group, isothiazolyl group, oxadiazolyl group, thiadiazolyl group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, and phenoxazinyl group, and with the proviso that the above aromatic hydrocarbon group and the heterocyclic group forming the multiple linking group for $L^2$ are mutually the same or different and adjacent ones thereof are not bonded to further form a ring;

n and m are each independently an integer of 1 to 5;

when n is an integer of 2 to 5, a plurality of Cz are mutually the same or different;

when m is an integer of 2 to 5, Az are mutually the same or different;

Cz is represented by a formula (1a) below; and

Az is a group represented by a formula (11) below,

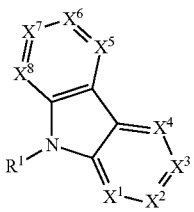

(1a)

where: $X^1$ to $X^8$ are each independently CR or a nitrogen atom;

R and $R^1$ each independently represent a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, a substituted or unsubstituted arylthio group having 6 to 30 ring carbon atoms, a substituted or unsubstituted aromatic hydrocarbon group having 6 to 30 ring carbon atoms, or a substituted or unsubstituted heterocyclic group having 5 to 30 ring atoms, provided that the heterocyclic group having 5 to 30 ring atoms for R is selected from the group consisting of a pyridyl group, pyrimidinyl group, pyrazinyl group, pyridazynyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, 9-carbazolyl group, furyl group, thienyl group, oxazolyl group, thiazolyl group, isoxazolyl group, isothiazolyl group, oxadiazolyl group, thiadiazolyl group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, and phenoxazinyl group;

adjacent ones of R are mutually bonded to form a ring or are not bonded;

when a plurality of R are present, the plurality of R are the same or different;

one of R and $R^1$ is a single bond to be bonded to $L^1$ in the formula (1); and $R^1$ and adjacent R are mutually bonded to form a ring or are not bonded,

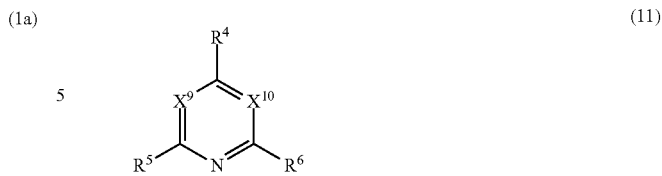

(11)

where: $X^9$ is $CR^9$ or a nitrogen atom;

$X^{10}$ is $CR^{10}$ or a nitrogen atom;

$R^4$ to $R^6$, $R^9$ and $R^{10}$ each independently represent a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms;

adjacent groups of $R^4$ to $R^6$, $R^9$ and $R^{10}$ are not bonded; and one of $R^4$ to $R^6$, $R^9$ and $R^{10}$ is a single bond to be bonded to $L^2$.

2. The compound according to claim 1, wherein the formula (1) is represented by a formula (1A) or (1B) below,

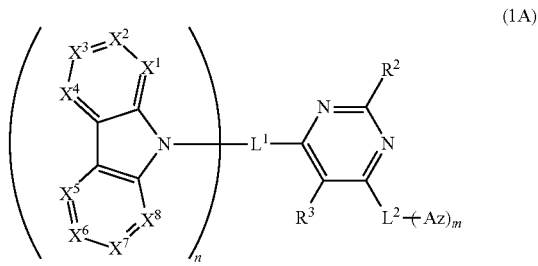

(1A)

where: $L^1$, $L^2$, $R^2$, $R^3$, Az, n and m respectively represent the same as $L^1$, $L^2$, $R^2$, $R^3$, Az, n and m in the formula (1); and $X^1$ to $X^8$ respectively represent the same as $X^1$ to $X^8$ in the formula (1a),

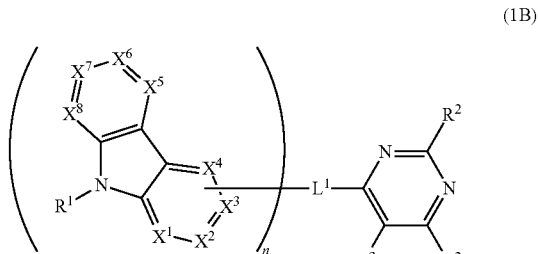

(1B)

where: $L^1$, $L^2$, $R^2$, $R^3$, Az, n and m respectively represent the same as $L^1$, $L^2$, $R^2$, $R^3$, Az, n and m in the formula (1);

$R^1$ and $X^1$ to $X^8$ respectively represent the same as $R^1$ and $X^1$ to $X^8$ in the formula (1a); and one of $X^1$ to $X^8$ of the formula (1B) is a carbon atom to be bonded to $L^1$.

3. The compound according to claim 1, wherein $X^1$ to $X^8$ are each independently CR.

4. The compound according to claim 1, wherein Az is selected from a substituted or unsubstituted pyridine ring, substituted or unsubstituted pyrimidine ring, and substituted or unsubstituted triazine ring.

5. The compound according to claim 4, wherein Az is selected from an unsubstituted pyridine ring, unsubstituted pyrimidine ring, and unsubstituted triazine ring.

6. The compound according to claim 1, wherein $X^9$ is $CR^9$ and $X^{10}$ is $CR^{10}$.

7. The compound according to claim 2, wherein the compound is represented by the formula (1A).

8. The compound according to claim 1, wherein $L^1$ is a substituted or unsubstituted aromatic hydrocarbon group having 6 to 30 ring carbon atoms.

9. The compound according to claim 1, wherein $L^1$ is a substituted or unsubstituted benzene ring.

10. The compound according to claim 1, wherein n is 1 or 2, and m is 1.

11. The compound according to claim 1, wherein the compound is represented by a formula (13A) below,

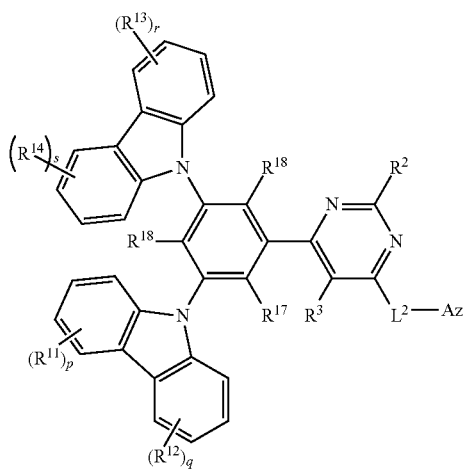

(13A)

where: $L^2$, $R^2$, $R^3$ and Az respectively represent the same as $L^2$, $R^2$, $R^3$ and Az in the formula (1);
each of $R^{11}$, $R^{12}$, $R^{13}$ and $R^{14}$ is bonded to any carbon atom of a carbazolyl group;
$R^{11}$, $R^{12}$, $R^{13}$, $R^{14}$, $R^{16}$, $R^{17}$ and $R^{18}$ represent the same as $R^3$ of the formula (1);
p, q, r and s are 4; and
a plurality of $R^{11}$, $R^{12}$, $R^{13}$ and $R^{14}$ are mutually the same or different.

12. The compound according to claim 1, wherein the compound is represented by a formula (15A) below,

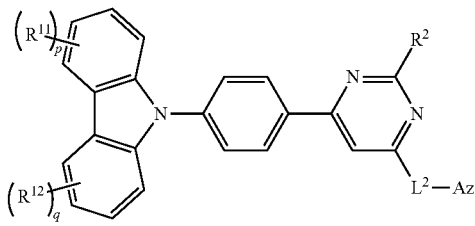

(15A)

where: $R^2$, $L^2$ and Az respectively represent the same as $R^2$, $L^2$ and Az in the formula (1);
$R^{11}$ and $R^{12}$ represent the same as $R^3$ of the formula (1); and
p and q are 4.

13. The compound according to claim 1, wherein $L^2$ is a substituted or unsubstituted aromatic hydrocarbon group having 6 to 30 ring carbon atoms.

14. The compound according to claim 1, wherein $L^2$ is a substituted or unsubstituted benzene ring.

15. An organic-EL-device material comprising: the compound according to claim 1.

16. An organic electroluminescence device comprising:
an anode;
a cathode opposite the anode; and
an organic layer provided between the anode and the cathode, the organic layer having one or more layers at least including an emitting layer, wherein
at least one layer of the organic layer comprises the compound according to claim 1.

17. The organic electroluminescence device according to claim 16, wherein
the organic layer comprises an electron transporting zone between the emitting layer and the cathode, and
the at least one layer containing the compound in the organic layer is the electron transporting zone.

18. The organic electroluminescence device according to claim 17, wherein the electron transporting zone further comprises at least one of an electron-donating dopant and an organic metal complex.

19. The organic electroluminescence device according to claim 18, wherein the at least one of the electron-donating dopant and the organic metal complex is at least one selected from the group consisting of an alkali metal, an alkali metal compound, an alkaline-earth metal, an alkaline-earth metal compound, a rare-earth metal, a rare-earth metal compound, an organic metal complex including an alkali metal, an organic metal complex including an alkaline-earth metal, and an organic metal complex including rare-earth metal.

20. An electronic device comprising the organic electroluminescence device according to claim 16.

21. The compound according to claim 2, wherein the compound is represented by formula (1B).

22. The compound according to claim 21, wherein $R^2$ is a group selected from the following formulae (R-2a) to (R-2d):

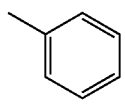

(R-2a)

-continued

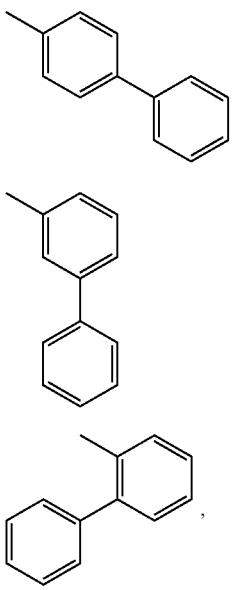

(R-2b)

(R-2c)

(R-2d)

wherein the formulae (R-2a) to (R-2d) are optionally substituted with an alkyl group having 1 to 6 carbon atoms.

23. The compound according to claim 21, wherein $L^2$ is a group selected from the following formulae (L-2a), (L-2b), (L-2c) and (L-2f):

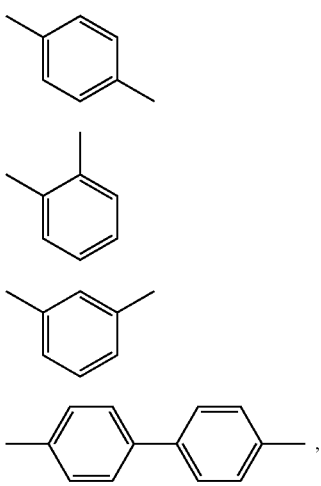

(L-2a)

(L-2b)

(L-2c)

(L-2f)

wherein the formulae (L-2a), (L-2b), (L-2c) and (L-2f) are optionally substituted with an alkyl group having 1 to 6 carbon atoms.

24. The compound according to claim 21, wherein Az is a group selected from a substituted or unsubstituted pyridyl group, a substituted or unsubstituted pyrimidinyl group, and a substituted or unsubstituted triazinyl group.

25. The compound according to claim 21, wherein $R^3$ is a hydrogen atom.

26. The compound according to claim 21, wherein $L^1$ is a group selected from the following formulae (L-1a), (L-1b), (L-1c) and (L-1f):

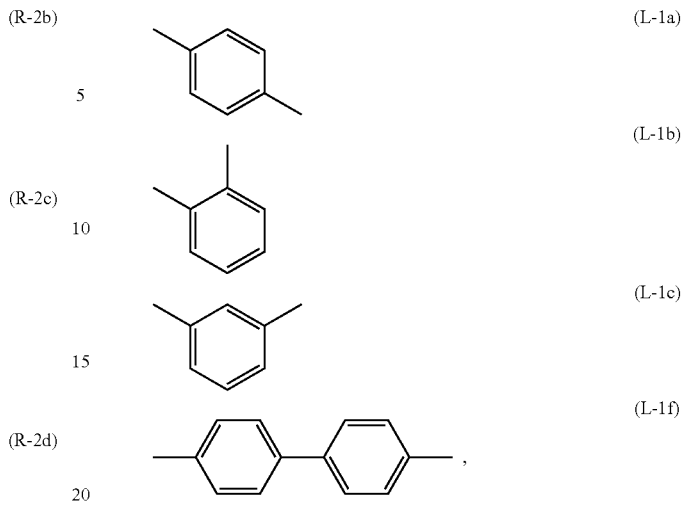

(L-1a)

(L-1b)

(L-1c)

(L-1f)

wherein the formulae (L-1a), (L-1b), (L-1c) and (L-1f) are optionally substituted with an alkyl group having 1 to 6 carbon atoms.

27. The compound according to claim 21, wherein one of $X^1$ to $X^8$ is a carbon atom bonded to $L^1$, and the others are CR.

28. The compound according to claim 21, wherein n is 1.

29. The compound according to claim 21, wherein $R^1$ is an unsubstituted phenyl group.

30. The compound according to claim 21, wherein $R^2$ is a group selected from the following formulae (R-2a) to (R-2d):

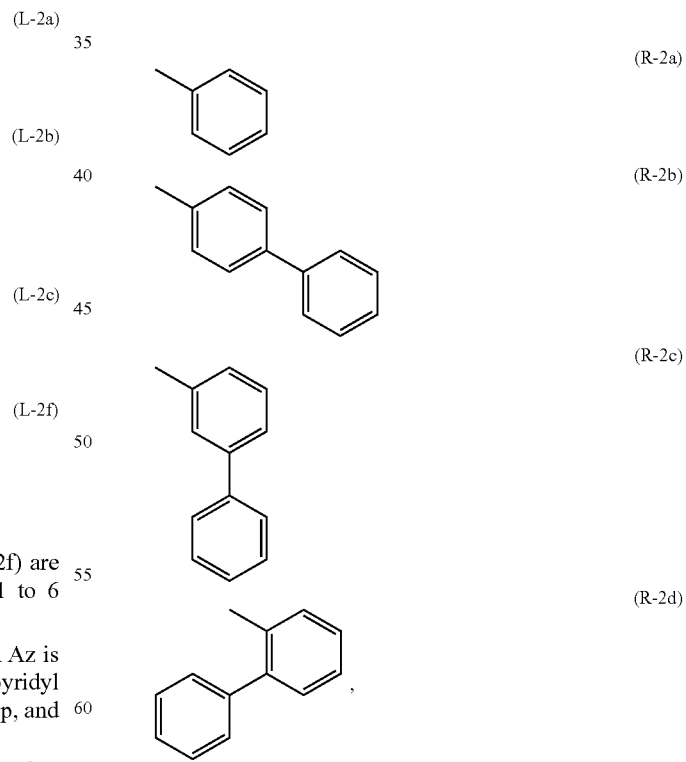

(R-2a)

(R-2b)

(R-2c)

(R-2d)

wherein the formulae (R-2a) to (R-2d) are optionally substituted with an alkyl group having 1 to 6 carbon atoms;

$L^2$ is a group selected from the following formulae (L-2a), (L-2b), (L-2c) and (L-2f):

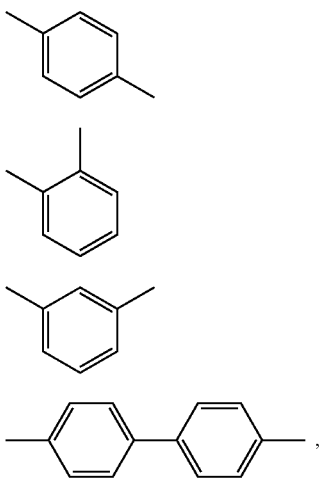

(L-2a)

(L-2b)

(L-2c)

(L-2f)

wherein the formulae (L-2a), (L-2b), (L-2c) and (L-2f) are optionally substituted with an alkyl group having 1 to 6 carbon atoms;
Az is a group selected from a substituted or unsubstituted pyridyl group, a substituted or unsubstituted pyrimidinyl group, or a substituted or unsubstituted triazinyl group;
$R^3$ is a hydrogen atom,
$L^1$ is a group selected from the following formulae (L-1a), (L-1b), (L-1c) and (L-1f):

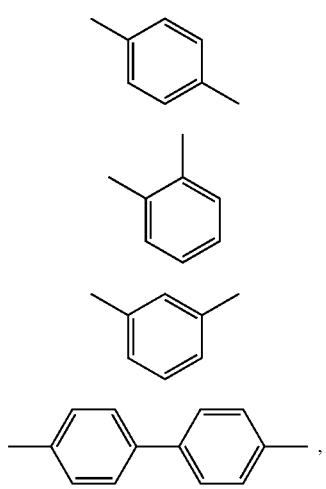

(L-1a)

(L-1b)

(L-1c)

(L-1f)

wherein the formulae (L-1a), (L-1b), (L-1c) and (L-1f) are optionally substituted with an alkyl group having 1 to 6 carbon atoms;
one of $X^1$ to $X^8$ is a carbon atom bonded to $L^1$, and the others are CR;
n is 1; and
$R^1$ is an unsubstituted phenyl group.

31. The compound according to claim 1, wherein in the formula (1), $L^1$ and $L^2$ are a substituted or unsubstituted aromatic hydrocarbon group having 6 to 30 ring carbon atoms.

32. The compound according to claim 1, wherein in the formula (1), $L^1$ and $L^2$ are a phenylene group.

33. The compound according to claim 31, wherein in the formula (1), $R^3$ is H.

34. The compound according to claim 33, wherein in the formula (1), Az is a pyridyl group.

35. The compound according to claim 34, wherein in the formula (1), $X^1$ to $X^8$ are each CH.

36. A compound represented by a formula (1) below,

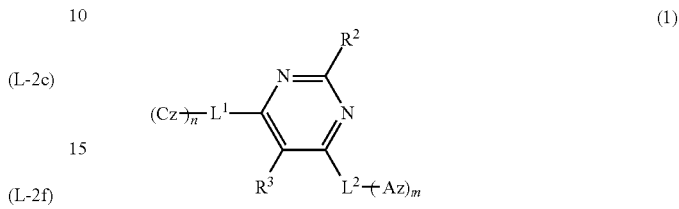

(1)

where: $R^3$ represents a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, a substituted or unsubstituted arylthio group having 6 to 30 ring carbon atoms, a substituted or unsubstituted aromatic hydrocarbon group having 6 to 30 ring carbon atoms, or a substituted or unsubstituted heterocyclic group having 5 to 30 ring atoms;
$R^2$ is a substituted or unsubstituted aromatic hydrocarbon group having 6 to 30 ring carbon atoms;
when $R^2$ has a substituent, the substituent is a halogen atom, a hydroxyl group, a cyano group, a nitro group, a carboxy group, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted oxygen-containing heterocyclic group having 5 to 30 ring carbon atoms, a substituted or unsubstituted sulfur-containing heterocyclic group having 5 to 30 ring carbon atoms, or a substituted or unsubstituted aromatic hydrocarbon group having 6 to 30 ring carbon atoms;
when the aryloxy group and the arylthio group respectively have substituents, adjacent ones of the substituents are bonded to form a ring or are not bonded;
$L^1$ is a single bond or a linking group and the linking group in $L^1$ is an alkenylene group, an alkynylene group, a substituted or unsubstituted aromatic hydrocarbon group having 6 to 30 ring carbon atoms, a substituted or unsubstituted heterocyclic group having 5 to 30 ring atoms, a multiple linking group provided by bonding two to four groups selected from the above aromatic hydrocarbon group, a multiple linking group provided by bonding two to four groups selected from the above heterocyclic group, or a multiple linking group provided by bonding two to four groups selected from the above aromatic hydrocarbon group and the above heterocyclic group;

the above aromatic hydrocarbon group and the heterocyclic group forming the multiple linking group are mutually the same or different and adjacent ones thereof are bonded to further form a ring or are not bonded;

$L^2$ is a linking group and the linking group represents the same as the linking group in $L^1$ with the proviso that the heterocyclic group is selected from the group consisting of a pyridyl group, pyrimidinyl group, pyrazinyl group, pyridazynyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, imidazolyl group, pyrazolyl group, triazolyl group, tetrazolyl group, indolyl group, benzimidazolyl group, indazolyl group, imidazopyridinyl group, benzotriazolyl group, furyl group, thienyl group, oxazolyl group, thiazolyl group, isoxazolyl group, isothiazolyl group, oxadiazolyl group, thiadiazolyl group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, and phenoxazinyl group, and with the proviso that the above aromatic hydrocarbon group and the heterocyclic group forming the multiple linking group for $L^2$ are mutually the same or different and adjacent ones thereof are not bonded to further form a ring;

n and m are each independently an integer of 1 to 5;

when n is an integer of 2 to 5, a plurality of Cz are mutually the same or different;

when m is an integer of 2 to 5, Az are mutually the same or different;

Cz is represented by a formula (1a) below; and

Az is a quinolyl group, an isoquinolinyl group, a phenanthrolinyl group,

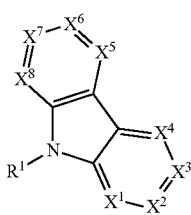

(1a)

where: $X^1$ to $X^8$ are each independently CR or a nitrogen atom;

R and $R^1$ each independently represent a hydrogen atom, a halogen atom, a hydroxyl group, a cyano group, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, a substituted or unsubstituted arylthio group having 6 to 30 ring carbon atoms, a substituted or unsubstituted aromatic hydrocarbon group having 6 to 30 ring carbon atoms, or a substituted or unsubstituted heterocyclic group having 5 to 30 ring atoms, provided that the heterocyclic group having 5 to 30 ring atoms for R is selected from the group consisting of a pyridyl group, pyrimidinyl group, pyrazinyl group, pyridazynyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, 9-carbazolyl group, furyl group, thienyl group, oxazolyl group, thiazolyl group, isoxazolyl group, isothiazolyl group, oxadiazolyl group, thiadiazolyl group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, and phenoxazinyl group;

adjacent ones of R are mutually bonded to form a ring or are not bonded;

when a plurality of R are present, the plurality of R are the same or different;

one of R and $R^1$ is a single bond to be bonded to $L^1$ in the formula (1); and $R^1$ and adjacent R are mutually bonded to form a ring or are not bonded.

37. The compound according to claim 36, wherein the formula (1) is represented by a formula (1A) or (1B) below,

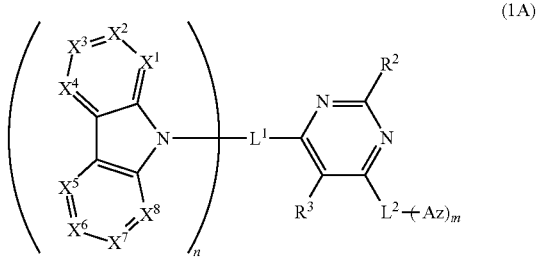

(1A)

where: $L^1$, $L^2$, $R^2$, $R^3$, Az, n and m respectively represent the same as $L^1$, $L^2$, $R^2$, $R^3$, Az, n and m in the formula (1); and $X^1$ to $X^8$ respectively represent the same as $X^1$ to $X^8$ in the formula (1a),

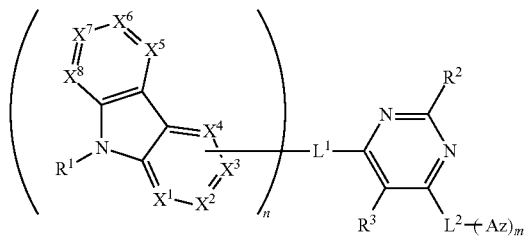

(1B)

where: $L^1$, $L^2$, $R^2$, $R^3$, Az, n and m respectively represent the same as $L^1$, $L^2$, $R^2$, $R^3$, Az, n and m in the formula (1);

$R^1$ and $X^1$ to $X^8$ respectively represent the same as $R^1$ and $X^1$ to $X^8$ in the formula (1a); and one of $X^1$ to $X^8$ of the formula (1B) is a carbon atom to be bonded to $L^1$.

38. The compound according to claim 36, wherein $X^1$ to $X^8$ are each independently CR.

39. The compound according to claim 37, wherein the compound is represented by the formula (1A).

40. The compound according to claim 36, wherein $L^1$ is a substituted or unsubstituted aromatic hydrocarbon group having 6 to 30 ring carbon atoms.

41. The compound according to claim 36, wherein $L^1$ is a substituted or unsubstituted benzene ring.

42. The compound according to claim 36, wherein n is 1 or 2, and m is 1.

43. The compound according to claim 36, wherein the compound is represented by a formula (15A) below,

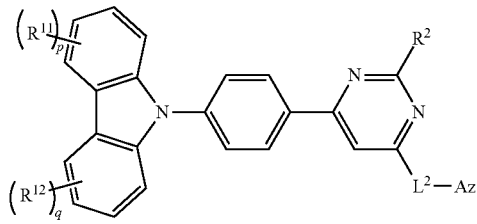

(15A)

where: $R^2$, $L^2$ and Az respectively represent the same as $R^2$, $L^2$ and Az in the formula (1);

$R^{11}$ and $R^{12}$ represent the same as $R^3$ of the formula (1); and p and q are 4.

44. The compound according to claim 36, wherein $L^2$ is a substituted or unsubstituted aromatic hydrocarbon group having 6 to 30 ring carbon atoms.

45. The compound according to claim 36, wherein $L^2$ is a substituted or unsubstituted benzene ring.

46. An organic-EL-device material comprising: the compound according to claim 36.

47. An organic electroluminescence device comprising:
an anode;
a cathode opposite the anode; and
an organic layer provided between the anode and the cathode, the organic layer having one or more layers at least including an emitting layer, wherein
at least one layer of the organic layer comprises the compound according to claim 36.

48. The organic electroluminescence device according to claim 47, wherein
the organic layer comprises an electron transporting zone between the emitting layer and the cathode, and
the at least one layer containing the compound in the organic layer is the electron transporting zone.

49. The organic electroluminescence device according to claim 48, wherein the electron transporting zone further comprises at least one of an electron-donating dopant and an organic metal complex.

50. The organic electroluminescence device according to claim 49, wherein the at least one of the electron-donating dopant and the organic metal complex is at least one selected from the group consisting of an alkali metal, an alkali metal compound, an alkaline-earth metal, an alkaline-earth metal compound, a rare-earth metal, a rare-earth metal compound, an organic metal complex including an alkali metal, an organic metal complex including an alkaline-earth metal, and an organic metal complex including rare-earth metal.

51. An electronic device comprising the organic electroluminescence device according to claim 47.

\* \* \* \* \*